US012576188B2

(12) United States Patent
Retting et al.

(10) Patent No.: US 12,576,188 B2
(45) Date of Patent: Mar. 17, 2026

(54) ENGINEERED THREE-DIMENSIONAL SKIN TISSUES, ARRAYS THEREOF, AND METHODS OF MAKING THE SAME

(71) Applicants: Organovo, Inc., San Diego, CA (US); L'Oreal, Paris (FR)

(72) Inventors: Kelsey Nicole Retting, San Diego, CA (US); Colin M. O'Neill, La Jolla, CA (US); Deborah Lynn Greene Nguyen, San Diego, CA (US); Sharon C. Presnell, Poway, CA (US); Jessica Langer, Teaneck, NJ (US); Guive Balooch, New York, NY (US); Elizabeth Wu, San Francisco, CA (US); Julien Demaude, Paris (FR)

(73) Assignee: Organovo, Inc., Sam Diego, CA (US)

( * ) Notice: Subject to any disclaimer, the term of this patent is extended or adjusted under 35 U.S.C. 154(b) by 497 days.

(21) Appl. No.: 18/068,137

(22) Filed: Dec. 19, 2022

(65) Prior Publication Data

US 2023/0201420 A1 Jun. 29, 2023

Related U.S. Application Data

(62) Division of application No. 15/524,578, filed as application No. PCT/US2015/059327 on Nov. 5, 2015, now Pat. No. 11,529,436.

(60) Provisional application No. 62/140,381, filed on Mar. 30, 2015, provisional application No. 62/075,703, filed on Nov. 5, 2014.

(51) Int. Cl.
| | |
|---|---|
| *A61L 27/36* | (2006.01) |
| *A61L 27/50* | (2006.01) |
| *A61L 27/60* | (2006.01) |
| *C12N 5/071* | (2010.01) |
| *G01N 33/50* | (2006.01) |

(52) U.S. Cl.
CPC .............. *A61L 27/362* (2013.01); *A61L 27/50* (2013.01); *A61L 27/60* (2013.01); *C12N 5/0698* (2013.01); *G01N 33/5044* (2013.01); *A61L 2300/64* (2013.01); *C12N 2502/091* (2013.01); *C12N 2502/094* (2013.01); *C12N 2502/1323* (2013.01); *C12N 2503/06* (2013.01); *C12N 2533/54* (2013.01); *C12N 2533/74* (2013.01); *C12N 2533/90* (2013.01); *C12N 2535/00* (2013.01)

(58) Field of Classification Search
None
See application file for complete search history.

(56) References Cited

U.S. PATENT DOCUMENTS

| | | | |
|---|---|---|---|
| 4,759,764 | A | 7/1988 | Fawcett et al. |
| 4,808,435 | A | 2/1989 | Cropp et al. |
| 5,099,090 | A | 3/1992 | Allan et al. |
| 6,315,469 | B1 | 11/2001 | Alvarez et al. |
| 6,401,795 | B1 | 6/2002 | Cesarano, III et al. |
| 6,454,972 | B1 | 9/2002 | Morisette et al. |
| 6,520,997 | B1 | 2/2003 | Pekkarinen et al. |
| 6,537,567 | B1 | 3/2003 | Niklason et al. |
| 6,561,607 | B1 | 5/2003 | Lubinsky et al. |
| 6,568,787 | B1 | 5/2003 | Girones et al. |
| 6,642,243 | B1 | 11/2003 | Imanzahrai |
| 6,713,772 | B2 | 3/2004 | Goodman et al. |
| 6,939,489 | B2 | 9/2005 | Moszner et al. |
| 6,942,830 | B2 | 9/2005 | Muelhaupt et al. |
| 6,979,670 | B1 | 12/2005 | Lyngstadaas et al. |
| 6,986,739 | B2 | 1/2006 | Warren et al. |
| 7,051,654 | B2 | 5/2006 | Boland et al. |
| 7,196,842 | B2 | 3/2007 | Weigl et al. |
| 7,484,837 | B2 | 2/2009 | Koga et al. |
| 7,625,198 | B2 | 12/2009 | Lipson et al. |
| 7,651,665 | B2 | 1/2010 | Gonzalez et al. |
| 7,680,555 | B2 | 3/2010 | Dunn et al. |
| 7,767,446 | B2 | 8/2010 | Robbins et al. |
| 7,887,843 | B2 | 2/2011 | Libera et al. |
| 7,980,645 | B2 | 7/2011 | Ohtsuka et al. |
| 8,143,055 | B2 | 3/2012 | Forgacs et al. |
| 8,241,905 | B2 | 8/2012 | Forgacs et al. |
| 8,343,740 | B2 | 1/2013 | Gonda et al. |
| 8,580,546 | B2 | 11/2013 | Gonda et al. |
| 8,728,807 | B2 | 5/2014 | Forgacs et al. |
| 8,747,880 | B2 | 6/2014 | Forgacs et al. |
| 8,852,932 | B2 | 10/2014 | Forgacs et al. |

(Continued)

FOREIGN PATENT DOCUMENTS

| | | |
|---|---|---|
| CA | 2306346 A1 | 1/1999 |
| EP | 2090584 A1 | 8/2009 |

(Continued)

OTHER PUBLICATIONS

Lee, V, et al., "Design and Fabrication of Human Skin by Three-Dimensional Bioprinting," *Tissue Engineering: Part C* 20(6):473-484, Mary Ann Liebert, Inc., United States (2014).

Michael, S., et al., "Tissue Engineered Skin Substitutes Created by Laser-Assisted Bioprinting Form Skin-Like Structures in the Dorsal Skin Fold Chamber in Mice," *PLOS One* 8(3):e57741, Scientific Research Publishing Inc., United States 12 pages (2013).

Velasquillo, C., et al., "Skin 3D Bioprinting. Applications in Cosmetology," *Journal of Cosmetics, Dermatological Sciences and Applications* 3:85-89, Scientific Research Publishing Inc., United States (2013).

International Search Report for International Application No. PCT/US2015/059327, Korean Intellectual Property Office, Republic of Korea, mailed on Feb. 11, 2016, 6 pages.

(Continued)

*Primary Examiner* — Blaine Lankford
(74) *Attorney, Agent, or Firm* — Sterne, Kessler, Goldstein & Fox P.L.L.C.

(57) ABSTRACT

Disclosed are bioprinted, three-dimensional, biological skin tissues comprising: a dermal layer comprising dermal fibroblasts; and an epidermal layer comprising keratinocytes, the epidermal layer in contact with the dermal layer to form the three-dimensional, engineered, biological skin tissue. Also disclosed are arrays of engineered skin tissues and methods of making engineered skin tissues.

20 Claims, 29 Drawing Sheets

(56) References Cited

U.S. PATENT DOCUMENTS

| | | | |
|---|---|---|---|
| 8,931,880 | B2 | 1/2015 | Murphy et al. |
| 9,149,952 | B2 | 10/2015 | Murphy et al. |
| 10,967,560 | B2 | 4/2021 | Murphy et al. |
| 11,529,436 | B2* | 12/2022 | Retting ................... A61L 27/50 |
| 2001/0042942 | A1 | 11/2001 | Hizumi et al. |
| 2002/0171178 | A1 | 11/2002 | Dean et al. |
| 2002/0182633 | A1 | 12/2002 | Chen et al. |
| 2002/0188349 | A1 | 12/2002 | McAllister et al. |
| 2003/0049839 | A1 | 3/2003 | Romero-Ortega et al. |
| 2003/0149505 | A1 | 8/2003 | Mogensen |
| 2003/0153078 | A1 | 8/2003 | Libera et al. |
| 2003/0175410 | A1 | 9/2003 | Campbell et al. |
| 2003/0236588 | A1 | 12/2003 | Jang et al. |
| 2004/0006405 | A1 | 1/2004 | Chen et al. |
| 2004/0132184 | A1 | 7/2004 | Dennis et al. |
| 2004/0197367 | A1 | 10/2004 | Rezania et al. |
| 2004/0219133 | A1 | 11/2004 | Lyles |
| 2004/0253365 | A1 | 12/2004 | Warren et al. |
| 2005/0009178 | A1 | 1/2005 | Yost et al. |
| 2005/0091576 | A1 | 4/2005 | Relyea et al. |
| 2005/0169962 | A1 | 8/2005 | Bhatia et al. |
| 2005/0226856 | A1 | 10/2005 | Ahlfors |
| 2005/0276791 | A1 | 12/2005 | Hansford et al. |
| 2006/0099287 | A1 | 5/2006 | Kim et al. |
| 2006/0198918 | A1 | 9/2006 | Koyagi et al. |
| 2006/0237880 | A1 | 10/2006 | Wicker et al. |
| 2006/0270032 | A1 | 11/2006 | Bhatia et al. |
| 2007/0142916 | A1 | 6/2007 | Olson, Jr. et al. |
| 2007/0200276 | A1 | 8/2007 | Mackey et al. |
| 2007/0231787 | A1 | 10/2007 | Voelker |
| 2007/0299508 | A1 | 12/2007 | Morrison et al. |
| 2008/0027114 | A1 | 1/2008 | Funke et al. |
| 2008/0070304 | A1 | 3/2008 | Forgacs et al. |
| 2008/0097575 | A1 | 4/2008 | Cottone |
| 2008/0192074 | A1 | 8/2008 | Dubois et al. |
| 2008/0193910 | A1 | 8/2008 | Larkin et al. |
| 2009/0076531 | A1 | 3/2009 | Richardson et al. |
| 2009/0117087 | A1 | 5/2009 | Carroll et al. |
| 2009/0142307 | A1 | 6/2009 | Athanasiou et al. |
| 2009/0206522 | A1 | 8/2009 | Hein et al. |
| 2009/0208466 | A1 | 8/2009 | Yoo et al. |
| 2009/0208577 | A1 | 8/2009 | Xu et al. |
| 2009/0239302 | A1 | 9/2009 | Decher et al. |
| 2009/0248145 | A1 | 10/2009 | Chan et al. |
| 2009/0267269 | A1 | 10/2009 | Lim et al. |
| 2010/0056390 | A1 | 3/2010 | Fischbach |
| 2010/0160183 | A1 | 6/2010 | Xu et al. |
| 2010/0191360 | A1 | 7/2010 | Napadensky et al. |
| 2010/0254900 | A1 | 10/2010 | Campbell et al. |
| 2011/0052693 | A1 | 3/2011 | Kao et al. |
| 2011/0064784 | A1 | 3/2011 | Mullens et al. |
| 2011/0172611 | A1 | 7/2011 | Yoo et al. |
| 2011/0180914 | A1 | 7/2011 | Do et al. |
| 2011/0212501 | A1 | 9/2011 | Yoo |
| 2011/0250688 | A1 | 10/2011 | Hasan |
| 2012/0045770 | A1 | 2/2012 | Pongracz et al. |
| 2012/0089238 | A1 | 4/2012 | Kang et al. |
| 2012/0276154 | A1 | 11/2012 | Mahjour et al. |
| 2013/0078666 | A1 | 3/2013 | Stark et al. |
| 2013/0108726 | A1 | 5/2013 | Uckelmann et al. |
| 2013/0164339 | A1 | 6/2013 | Murphy et al. |
| 2013/0190210 | A1 | 7/2013 | Murphy et al. |
| 2013/0193619 | A1 | 8/2013 | Church et al. |
| 2013/0236431 | A1 | 9/2013 | Gourdie et al. |
| 2013/0236879 | A1 | 9/2013 | Berry et al. |
| 2013/0345794 | A1 | 12/2013 | Khatiwala et al. |
| 2014/0012225 | A1 | 1/2014 | Yoo et al. |
| 2014/0044822 | A1 | 2/2014 | Mulliken |
| 2014/0093932 | A1 | 4/2014 | Murphy et al. |
| 2014/0099709 | A1 | 4/2014 | Presnell et al. |
| 2014/0131313 | A1 | 5/2014 | Wakamatsu et al. |
| 2014/0220685 | A1 | 8/2014 | Forgacs et al. |
| 2014/0265049 | A1 | 9/2014 | Burris et al. |
| 2014/0274802 | A1 | 9/2014 | Shepherd et al. |
| 2014/0287960 | A1 | 9/2014 | Shepherd et al. |
| 2014/0358273 | A1 | 12/2014 | Labossiere et al. |
| 2015/0004273 | A1 | 1/2015 | Forgacs et al. |
| 2015/0037445 | A1 | 2/2015 | Murphy et al. |
| 2015/0057786 | A1 | 2/2015 | Murphy et al. |
| 2015/0139960 | A1 | 5/2015 | Tumey et al. |
| 2015/0282885 | A1 | 10/2015 | King et al. |
| 2015/0314613 | A1 | 11/2015 | Murphy et al. |
| 2016/0122723 | A1 | 5/2016 | Retting et al. |

FOREIGN PATENT DOCUMENTS

| | | |
|---|---|---|
| JP | 2001038981 A | 2/2001 |
| JP | 2005031144 A | 2/2005 |
| JP | 2006159117 A | 6/2006 |
| JP | 2011-92179 A | 5/2011 |
| JP | 2013-542728 A | 11/2013 |
| JP | 2014-204711 A | 10/2014 |
| JP | 2014-531204 A | 11/2014 |
| KR | 20090087748 A | 8/2009 |
| RU | 2371758 C2 | 10/2009 |
| WO | WO-9901538 A1 | 1/1999 |
| WO | WO-0168811 A2 | 9/2001 |
| WO | WO-2004108418 A1 | 12/2004 |
| WO | WO-2005025493 A2 | 3/2005 |
| WO | WO-2005081970 A2 | 9/2005 |
| WO | WO-2007076272 A2 | 7/2007 |
| WO | WO-2007115336 A2 | 10/2007 |
| WO | WO-2007115337 A2 | 10/2007 |
| WO | WO-2007124023 A2 | 11/2007 |
| WO | WO-2007125893 A1 | 11/2007 |
| WO | WO-2007126411 A2 | 11/2007 |
| WO | WO-2007136936 A2 | 11/2007 |
| WO | WO-2009102484 A2 | 8/2009 |
| WO | WO 2009/107266 A1 | 9/2009 |
| WO | WO-2009154466 A1 | 12/2009 |
| WO | WO-2010008905 A2 | 1/2010 |
| WO | WO 2010/030964 A2 | 3/2010 |
| WO | WO-2011038373 A2 | 3/2011 |
| WO | WO-2011088213 | 7/2011 |
| WO | WO-2011097330 A2 | 8/2011 |
| WO | WO-2011107599 A1 | 9/2011 |
| WO | WO-2011119059 A1 | 9/2011 |
| WO | WO-2012003465 A2 | 1/2012 |
| WO | WO-2012054195 A2 | 4/2012 |
| WO | WO-2012131000 A1 | 10/2012 |
| WO | WO 2013/040078 A2 | 3/2013 |
| WO | WO 2013/123049 A1 | 8/2013 |
| WO | WO-2013130823 A1 | 9/2013 |
| WO | WO-2013192290 A1 | 12/2013 |
| WO | WO-2015066705 A1 | 5/2015 |

OTHER PUBLICATIONS

Written Opinion for International Application No. PCT/US2015/059327, Korean Intellectual Property Office, Republic of Korea, mailed on Feb. 11, 2016, 16 pages.

Koch, L., et al., "Laser printing of skin cells and human stem cells," *Tissue Engineering Part C Methods* 16(5):847-854, Mary Ann Liebert, Inc., United States (2010).

Malda, J., et al., "25th anniversary article: Engineering hydrogels for biofabrication," *Advanced Materials* 25(36):5011-5028, Wiley-VCH, Germay (2013).

Macneil, S., "Progress and opportunities for tissue-engineered skin," Nature 445(7130):874-880, Nature Publishing Group, England (2007).

Ponec, M., et al., "Endothelial network formed with human dermal microvascular endothelial cells in autologous multicellular skin substitutes," *Angiogenesis* 7(4):295-305, Springer, Germany (2004).

Pampaloni, F. and Stelzer, E.H.K., "Three-Dimensional Cell Cultures in Toxicology," *Biotechnology and Genetic Engineering Reviews* 26:117-138, Taylor & Francis, England (2009).

Office Action mailed Mar. 8, 2016, in U.S. Appl. No. 14/933,822, Retting, K.N et al., filed Nov. 5, 2015, 26 pages.

Office Action mailed Jul. 22, 2016, in U.S. Appl. No. 14/933,822, Retting, K.N et al., filed Nov. 5, 2015, 28 pages.

Dababneh, A.B., et al., "Bioprinting Technology: A Current State-of-the-Art Review," *Journal of Manufacturing Science and Engi-*

(56) References Cited

OTHER PUBLICATIONS neering 136(6):061016/1-061016/11, The American Society of Mechanical Engineers, United States (2014).

Koch, L. et al., "Skin Tissue Generation by Laser Cell Printing," Biotechnology and Bioengineering 109(7): 1855-1863, Wiley and Sons, United States (2012).

Rimann, et al., "Additive Verfahren mit biologischen Materialien," as Orthopaede vol. 46, Aug. 24, 2014.

Rimann, et al., "Skin bioprinting: an innovative approach to produce standardized skin models on demand," as CTI Medtech Event 2012, Luzern, Switzerland, Sep. 24, 2012, retrieved on Apr. 18, 2018 from https://www.zhaw.ch/storage/lsfm/institute-zentren/icbt/tedd/bioprinting-poster.pdf.

Young-Joon, S et al., "Bioprinting technology and its applications," Eur J of Cardio-Thoracic Surgery 46(3):342-348, Oxford University Press, England (2014).

Extended European Search Report for EP Application No. EP 15857287.5, Munich, Germany, mailed on May 3, 2018, 8 pages.

Auxenfans, C., et al., "Evolution of three dimensional skin equivalent models reconstructed in vitro by tissue engineering," *Eur. J. Dermatol.* 19(2): 107-113, John Libbey Eurotext, France (2009).

Tsuchida, Y., "Written Opposition" in Japanese Patent No. 7227211, dated Aug. 21, 2023, 289 pages.

Inoue, R., Email "RE: Japanese Patent Application No. 2020-202360, Applicants: Organovo, Inc et al., Country: Japan, Our Ref.: SK-A1710D1," dated Sep. 21, 2023, 4 pages.

Japanese Patent Office, "Decision on Opposition" in Japanese Patent No. 7227211, dated Nov. 27, 2023, 41 pages.

Fujimaru, Y. and Inoue, R., Email Japanese Patent Application No. 2020-202360, Applicants: Organovo, Inc et al., Country: Japan, Our Ref.: SK-A1710D1,: dated Nov. 27, 2023, 1 page.

Office Action mailed Jun. 8, 2021, in U.S. Appl. No. 15/524,578, Retting, K.N et al., filed May 4, 2017, 13 pages.

Office Action mailed Jan. 7, 2022, in U.S. Appl. No. 15/524,578, Retting, K.N et al., filed May 4, 2017, 23 pages.

ATCC Product Catalog MCF7 (ATCC® HTB-22TM) https://www.atcc.org/products/all/HTB-22.aspx?slp=1#generalinformation, retrieved Sep. 18, 2015.

ATCC Product catalog Primary Subcutaneous Pre-adipocytes; Normal, Human (ATCC® PCS-210-01OTM) https://www.atcc.org/Products/All/PCS-210-010.aspx?slp=1, retrieved Sep. 18, 2015.

Baltich et al. Development of a Scaffoldless Three-Dimensional Engineered Nerve Using a Nerve-Fibroblast Co-Culture. In Vitro Cell. Dev. Biol.—Animal 46:438-444 (2010).

Bioscaffolder 2008, www.syseng.de, SYSENG Dipl.-Ing. Hendrik John.

Boland et al. Application of inkjet printing to tissue engineering. Biotech J. 1:910-917 (2006).

Boland et al. Cell and Organ Printing 2: Fusion of Cell Aggregates in Three-Dimensional Gels. The Anatomical Record, Part A. 272A:497-502 (2003).

Bunnell et al. Adipose-derived Stem Cells: Isolation, Expansion and Differentiation. Methods 45(2):115-120 (2008).

Chaterji et al. Scaffold-Free In Vitro Arterial Mimetics: The Importance of Smooth Muscle-Endothelium Contact. Tissue Engineering Part A 16(8):1901-1912 (2010).

Sciperio, Inc. 2003 R&D 100 Award Winner. Sciperio, http://www.sciperio.com/news/20031016.asp, accessed on Feb. 1, 2005, 2 pages.

CONSTANS. Body by Science. The Scientist 17(19):34-37 http://www.the-scientist.com/article/display/141541 (2003).

Co-pending U.S. Appl. No. 14/827,152, filed Aug. 14, 2015.

Co-pending U.S. Appl. No. 14/876,659, filed Oct. 6, 2015.

Co-pending U.S. Appl. No. 14/936,580, filed Nov. 9, 2015.

Cui et al. Direct Human Cartilage Repair Using Three-Dimensional Bioprinting Technology. Tissue Engineering Part A 18(11-12):1304-1312 (2012).

Dai et al. Fibroblast Aggregation by Suspension with Conjugates of Poly(ethylene glycol) and RGD. Biotechnology and Bioengineering 50(4):349-356 (May 20, 1996).

Dirat et al. Cancer-associated adipocytes exhibit an activated phenotype and contribute to breast cancer invasion. Cancer Res. 71(7):2455-2465 (2011).

Dominici et al. Minimal criteria for defining multipotent mesenchymal stromal cells, International Society for Cellular Therapy position statement. Cytotherapy 8(4):315-317 (2006).

Edelman. Vascular Tissue Engineering: Designer Arteries. Circ Res 85(12):1115-1117 (1999).

Egebald et al. Tumors as organs: complex tissues that interface with the entire organism. Dev Cell. 18(6):884-901 (2010).

Eisenberg et al. Bone Marrow Cells Transdifferentiate to Cardiomyocytes When Introduced into the Embryonic Heart. Stem Cells 24:1236-1245 (2006).

Fedorovich et al. Distinct Tissue Formation by Heterogeneous Printing of Osteo- and Endothelial Progenitor Cells. Tissue Engineering: Part A 17(15-16):2113-2123 (2011).

Fedorovich et al. Three-Dimensional Fiber Deposition of Cell-Laden, Viable Patterned-Constructs for Bone Tissue Printing, Tissue Engineering: Part.A 14(1):127-135 (2008).

Forgacs et al. Biological Relevance of Tissue Liquidity and Viscoelasticity Eds. A. Deutsch, M. Falcke, J. Howard and W. Zimmermann. Birkhauser. pp. 269-277 (2004).

Forgacs et al. Viscoelastic Properties of Living Embryonic Tissues: A Quantitative Study, Biophysical Journal 74(5):2227-2234 (May 1998).

Foty et al. Surface Tensions of Embryonic Tissues Predict Their Mutual Envelopment Behavior. Development 122(5):1611-1620 (1996).

Foty et al. The Differential Adhesion Hypothesis: A Direct Evaluation. Developmental Biology 278(1):255-263 (2005).

Frisman et al. Nanostructuring of PEG-fibrinogen polymeric scaffolds. Acta Biomaterialia 6(7):2518-2524 (2009).

Fuellhase et al. 264 Generation Of Organized Bladder Tissue Constructs Using a Novel Hybrid Printing System. European Urology Supplements 8(4):186 (2009).

Furukawa et al. Formation of Human Fibroblast Aggregates (Spheroids) by Rotational Culture. Cell Transplantation 10(4-5):441-445 (2001).

Furukawa et al. Scaffold-free cartilage tissue by mechanical stress loading for tissue engineering. In Tissue Engineering, ed by Daniel Eberli. InTech p. 409-428 (2010).

Furukawa et al. Tissue-engineered Skin Using Aggregates of Normal Human Skin Fibroblasts and Biodegradable Material. J. MK Organs 4:353-356 (2001).

Ghorbanian et al. Microfluidic direct writer with integrated declogging mechanism for fabricating cell-laden hydrogel constructs. Biomed Microdevices (doi: 10.1007/s10544-014-9842-8), Springer Science+Business Media New York 2014 (Mar. 4, 2014).

Glazier et al. Simulation of the Differential Adhesion Driven Rearrangement of Biological Cells. Physical Review E 47(3):2128-2154 (Mar. 1993).

Glicklis et al. Modeling Mass Transfer in Hepatocyte Spheroids via Cell Viability, Spheroid Size, and Hepatocellular Functions. Biotechnology and Bioengineering 86(6):672-680 (Jun. 20, 2004).

Graner et al. Simulation of Biological Cell Sorting Using a Two-Dimensional Extended Potts Model. Physical Review Letters 69(13):2013-2016 (Sep. 28, 1992).

Grange et al. Isolation and characterization of human breast tumor-derived endothelial cells. Oncol Rep. 15(2):381-386 (2006).

Gruene et al. Laser Printing of Stem Cells for Biofabrication of Scaffold-Free Autologous Grafts. Tissue Engineering: Part C 17(1):79-89 (2011).

Gruene et al. Laser printing of three-dimensional multicellular arrays for studies of cell-cell and cell-environment interactions. Tissue Eng Part C Methods 17(10):973-82 (Oct. 2011).

Guenard et al. Syngeneic Schwann Cells Derived from Adult Nerves Seeded in Semipermeable Guidance Channels Enhance Peripheral Nerve Regeneration. The Journal of Neuroscience 12(9):3310-3320 (Sep. 1992).

Guillemot et al. High-throughput laser printing of cells and biomaterials for tissue engineering. Acta biomaterialia 6:2494-2500 (2010).

(56)          References Cited

OTHER PUBLICATIONS

Hadlock et al. A Polymer Foam Conduit Seeded with Schwann Cells Promotes Guided Peripheral Nerve Regeneration. Tissue Engineering 6(2):119-127 (2000).

Halley et al. Growing Organs In the Lab. Longevity. 1-7 (Jun. 2009).

Harvey et al. Schwann cells and fetal tectal tissue cografted to the midbrain of newborn rats: fate of Schwann cells and their influence on host retinal innervation of grafts. Exp Neurol. 134(2):179-91 (1995).

Hockaday et al. Rapid 3D printing of anatomically accurate and mechanically heterogeneous aortic valve hydrogel scaffolds. Biofabrication 4(3):1-12 (2012).

Hubbard et al. Bioengineered, Autologous, Scaffold-free Nerve Conduit for Peripheral Nerve Repair. Abstract. AAHS/ASPN/ASRM 2011, Annual Scientific Meetings Program Book. pp. 140 and 159 (Jan. 12-18, 2011).

Ito et al. Novel Methodology for Fabrication of Tissue-Engineered Tubular Constructs Using Magnetite Nanoparticles and Magnetic Force, Tissue Engineering, Larchmont, NY, US, 11(9-10):1553-1561 (2005).

Iwasaki et al. Bioengineered Three-Layered Robust and Elastic Artery Using Hemodynamically-Equivalent Pulsatile Bioreactor. Circulation 18(14 Suppl):S53-S57 (2008).

Izaguirre et al. CompuCell, a multi-model framework for simulation of morphogenesis. Bioinformatics 20(7):1129-1137 (2004).

Jakab et al. Engineering Biological Structures of Prescribed Shape Using Self-assembling Multicellular Systems. PNAS USA 101:2864-2869 (2004). 1.

Jakab et al. Organ printing: fiction or science. Biorheology 43(3-4):371-375 (2004).

Jakab et al. Relating Cell and Tissue Mechanics: Implications and Applications. Developmental Dynamics 237:2438-2449 (2008).

Jakab et al. Three-dimensional tissue constructs built by bioprinting. Biorheology 43(3-4):509-513 (2006).

Jakab et al. Tissue Engineering by Self- Assembly and Bio-printing of living cells. Biofabrication 2(2):022001 (14 pp) (Jun. 2, 2010).

Jakab et al. Tissue Engineering by Self-Assembly of Cells Printed into Topologically Defined Structures. Tissue Engineering: Part A. 14:413-421 (Nov. 3, 2008).

Kasko. Degradable Poly(ethylene glycol) Hydrogels for 2D and 3D Cell Culture. Aldrich Materials Science, pp. 67-75 (no date available).

Kelm et al. Design of Custom-Shaped Vascularized Tissues Using Microtissue Spheroids as Minimal Building Units. Tissue Engineering 12(8):2151-2160 (2006).

Kelm et al. Microscale Tissue Engineering Using Gravity-Enforced Cell Assembly. TRENDS in Biotechnology 22(4):195-202 (Apr. 2004).

Khatiwala et al. 3D Cell Bioprinting for Regenerative Medicine Research and Therapies. Gene Therapy and Regulation 7(1):1-19 (2012).

King et al. Development of 3D bioprinted human breast cancer for in vitro screening of therapeutics targeted against cancer progression. IEEE the American Society for Cell biology. 2013 ASCB annual meeting. New Orleans: IEEE Dec. 14-18, 2013.

Koibuchi et al. Behavior of Cells in Artificially Made Cell Aggregates and Tissue Fragments after Grafting to Developing Hind Limb Buds in Xenopus laevis. The International Journal of Developmental Biology 43(2):141-148 (1999).

Korff et al. Blood Vessel Maturation in a 3-Dimensional Spheroidal Coculture Model: Direct Contact with Smooth Muscle Cells Regulates Endothelial Cell Quiescence and Abrogates VEGF Responsiveness. The FASEB Journal 15:447-457 (Feb. 2001).

Larkin et al. Structure and Functional Evaluation of Tendon-Skeletal Muscle Constructs Engineered in Vitro. Tissue Eng. 12(11):3149-3158 (Nov. 2006).

Lee et al. Multi-layered Culture of Human Skin Fibroblasts and Keratinocytes Through Three-dimensional Freeform Fabrication. Biomaterials 30:1587-1595 (2009).

L'Heureux et al. A completely biological tissue-engineered human blood vessel. The FASEB Journal 12 (1):47-56 (1998).

L'Heureux et al. Human tissue-engineered blood vessels for adult arterial revascularization. Nature Medicine 12 (3):361-365 (2006).

L'Heureux et al. Sheet-Based Tissue Engineering From Bench Top to the First Clinical Use of a Completely Biological Tissue Engineered Vessel. The FASEB Journal 12(1):47-56 (Abstract) (2006).

Luo et al. Three-dimensional microtissue assay for high-throughput cytotoxicity of nanoparticles. Anal Chem. 84(15):6731-6738 (Aug. 7, 2012).

Marga et al. Bioprint Engineered Fully Biological Nerve Graft. Poster Presentation TERMIS Dec. 5-8, 2010, Orlando, Florida, 1 page.

Marga et al. Construction of a Bioprinted Fully Biological Nerve Graft. Biophysical Journal 96(3 supp 1):643a Abstract (Feb. 2009).

Marga et al. Developmental Biology and Tissue Engineering, Birth Defects Research (Part C) 81:320-328 (2007).

Marga et al. Engineered Fully Biological Nerve Graft. Oral Presentation, International Conference on Biofabrication, Oct. 3-6, 2010, Philadelphia, Pennsylvania, 1 page.

Marga et al. Engineered Fully Biological Nerve Graft. Poster Presentation Biophysical Society Meeting, Mar. 4, 2009, 1 page.

Marga et al. Toward Engineering Functional Organ Modules by Additive Manufacturing. Biofabrication 4:022001 (12 pp) (2012).

Martin et al. Computer-Based Technique for Cell Aggregation Analysis and Cell Aggregation in In Vitro Chondrogenesis. Cytometry 28(2):141-146 (1997).

Mcguigan et al. Vascularized organoid engineered by modular assembly enables blood perfusion. PNAS, 103(31):11461-11466 (2006).

Mehesz et al. Scalable robotic biofabrication of tissue spheroids. Biofabrication 3:1-8 (2011).

Mironov et al. Bioprinting Living Structures. J. Mat. Chem. 17:2054-2060 (2007).

Mironov et al. Organ Printing: Computer-Aided Jet-Based 3D Tissue Engineering. TRENDS in Biotechnology 21(4):157-161 (Apr. 2003).

Mironov et al. Organ Printing: Self-Assembling Cell Aggregates as 'Bioink'. Science & Medicine 9(2):69-71 (Apr. 2003).

Mironov et al. Organ Printing: Tissue Spheroids as Building Blocks. Biomaterials 30:2164-2174 (2009).

Mizumoto et al. Formation of Cylindrical Multicellular Aggregate (Cylindroid) and Express of Liver Specific Functions of Primary Rat Hepatocytes. Cytotechnology 31:69-75 (1999).

Mombach et al. Quantitative Comparison Between Differential Adhesion Models and Cell Sorting in the Presence and Absence of Fluctuations. Physical Review Letters 75(11):2244-2247 (Sep. 11, 1995).

Moon et al. Layer by Layer Three-dimensional Tissue Epitaxy by Cell-Laden Hydrogel Droplets. Tissue Engineering Part C: Methods 16(1):157-166 (2010).

Mroue et al. Three-dimensional cultures of mouse mammary epithelial cells. Methods Mol Biol. 945:221-250 (2013).

Neagu et al. Role of physical mechanisms in biological self-organization. Phys RevLett 95(17):178104 (2005).

Newman et al. Before programs: the physical origination of multicellular forms. Int J Dev Biol. 50(2-3):289-299 (2006).

Nickerson et al. Three-Dimensional Tissue Assemblies: Novel Models for the Study of Salmonella enterica Serovar Typhimurium Pathogenesis. Infection and Immunity 69(11):7106-7120 (Nov. 2001).

Niklason et al. Advances in Tissue Engineering of Blood Vessels and Other Tissues. Transpl. Immunol. 5(4):303-306 (1997).

Norotte et al. Scaffold-free vascular tissue engineering using bioprinting. Biomaterials 30:5910-5917 (2009).

Panagiotis et al. A unique aged human retinal pigmental epithelial cell line useful for studying lens differentiation in vitro. International Journal of Developmental Biology 45:753-758 (2001).

Pathology Outlines: Bladder. Normal Histology. pp. 1-4 (2011).

Paul et al. How to improve R&D productivity: the pharmaceutical industry's grand challenge. Nature Reviews Drug Discovery 9(3):203-214 (2010).

PCT/US2005/05735 International Search Report mailed Dec. 7, 2007.

(56)         References Cited

OTHER PUBLICATIONS

PCT/US2005/05735 International Preliminary Report on Patentability dated Mar. 3, 2009.
PCT/US2009/48530 International Preliminary Report on Patentability dated Jan. 13, 2011.
PCT/US2009/48530 International Search Report mailed Mar. 15, 2010.
PCT/US2011/023520 International Preliminary Report on Patentability dated Aug. 16, 2012.
PCT/US2011/023520 International Search Report dated Oct. 31, 2011.
PCT/US2011/028713 International Preliminary Report on Patentability dated Sep. 18, 2012.
PCT/US2011/028713 International Search Report dated Nov. 30, 2011.
PCT/US2011/053515 International Preliminary Report on Patentability dated May 3, 2013.
PCT/US2011/053515 International Search Report and Written Opinion dated May 1, 2012.
PCT/US2012/054923 International Preliminary Report on Patentability dated Mar. 20, 2014.
PCT/US2012/054923 International Search Report mailed Feb. 26, 2013.
PCT/US2012/054935 International Preliminary Report on Patentability Mar. 20, 2014.
PCT/US2012/054935 International Search Report mailed Feb. 28, 2013.
PCT/US2013/036479 International Preliminary Report on Patentability dated Oct. 21, 2014.
PCT/US2013/036479 International search report mailed Jul. 25, 2013.
PCT/US2013/046519 International Preliminary Report on Patentability dated Dec. 23, 2014.
PCT/US2013/046519 International Search Report mailed Sep. 5, 2013.
PCT/US2014/026679 International Preliminary Report on Patentability dated Sep. 24, 2015.
PCT/US2014/026679 International Search Report and Written Opinion dated Jul. 22, 2014.
PCT/US2014/041419 International Search Report and Written Opinion dated Jan. 2, 2015.
PCT/US2014/048962 International Search Report and Written Opinion dated Nov. 10, 2014.
Perez-Pomares et al. Tissue Fusion and Cell Sorting in Embryonic Development and Disease: Biomedical Implications. Bioessays 28:809-821 (2006).
Remuzzi et al. Vascular Smooth Muscle Cells on Hyaluronic Acid: Culture and Mechanical Characterization of an Engineered Vascular Construct. Tissue Engineering 10(516):699-710 (2004).
Riken. Self-healing hydrogels ease into production. Research Highlights: Materials. Downloaded from the Riken website: http://www.riken.jp/en/research/rikenresearch/highlights/7543/ (Nov. 1, 2013) [accessed Apr. 27, 2015].
Ryan et al. Tissue Spreading on Implantable Substrates is a Competitive Outcome of Cell-Cell vs. Cell-Substratum Adhesivity. PNAS 98(8):4323-4327 (Apr. 10, 2001).
Schuster et al. Why Drugs Fail—A Study on Side Effects in New Chemical Entities. Curr. Pharm. Des. 11:3545 (2005).
Shafrir et al. Mechanotransduction through the cytoskeleton. American Journal of Physiology 282:479-486 (2002).
Sheehan et al. Recent Patents and Trends in Bioprinting. Recent Patents on Biomedical Engineering 4:26-32 (2011).
Shim et al. Bioprinting of a mechanically enhanced three-dimensional dual cell-laden construct for osteochondral tissue engineering using a multi-head tissue/organ building system. J of Micromechanics and Microengineering. 22(Article No. 085014):1-11 (2012).
Siemionow et al. Current Techniques and Concepts in Peripheral Nerve Repair. Chapter 8, International Review of Neurobiology, 87:141-172 (2009).

Skardal et al. Bioprinting vessel-like constructs using hyaluronan hydrogels crosslinked with tetrahedral polyethylene glycol tetracrylates. Biomaterials 31:6173-6181 (2010).
Smith. A direct-write three-dimensional Bioassembly tool for regenerative medicine. The University of Arizona pp. 1-291 (Nov. 1, 2005).
Smith et al. Characterizing Environment Factors that Impact the Viability of Tissue-Engineered Constructs Fabricated by a Direct-Write Bioassembly Tool. Tissue Engineering, 13(2):373-385 (2007).
Smith et al. Three-Dimensional BioAssembly Tool for Generating Viable Tissue-Engineered Constructs. Tissue Engineering 10(9/10):1566-1576 (2004).
Steinberg. Does Differential Adhesion Govern Self-Assembly Processes in Histogenesis? Equilibrium Configurations and the Emergence of a Hierarchy Among Populations of Embryonic Cells. The Journal of Experimental Zoology 173(4):395-433 (Apr. 1970).
Steinberg et al. Liquid Behavior of Embryonic Tissues. Cell Behaviour pp. 583-697 (1982).
Stiles. UA Wins R & D 100 Award for Machine that Prints Tissue Cell-by-Cell. UANews Dec. 2, 2003, http://uanews.org/cgi-binfflebObjects/UANews.woa/wa/goPrint?ArticleID=8305, accessed on Feb. 1, 2005, 2 pages.
Tang et al. Molding of Three-Dimensional Microstructures of Gels. Journal of the American Chemical Society 125(43):12988-12989 (Oct. 29, 2003).
Tao et al. Bio-printing of living organized tissues using an inkjet technology. Database Accession No. PREV200700335042. FASEB Journal 23(5):A636 (2007).
Timmins et al. Hanging-Drop Multicellular Spheroids as a Model of Tumour Angiogenesis. Angiogenesis 7(2):97-103 (2004).
Tsang. Three-Dimensional Tissue Fabrication, Advanced drug delivery reviews 56(11):1635-1647 (2004).
U.S. Appl. No. 10/590,446 Office action dated Jan. 6, 2011.
U.S. Appl. No. 10/590,446 Office action dated Sep. 1, 2011.
U.S. Appl. No. 10/666,836 Office action dated Oct. 28, 2004.
U.S. Appl. No. 11/227,489 Office action dated Dec. 10, 2008.
U.S. Appl. No. 11/227,489 Office action dated Jul. 8, 2009.
U.S. Appl. No. 13/020,000 Office action dated Dec. 31, 2012.
U.S. Appl. No. 13/020,000 Office action dated Jul. 3, 2013.
U.S. Appl. No. 13/246,428 Office Action dated Aug. 26, 2014.
U.S. Appl. No. 13/246,428 Office Action dated Jan. 14, 2015.
U.S. Appl. No. 13/402,215 Office Action dated Mar. 19, 2013.
U.S. Appl. No. 13/529,172 Office action dated Sep. 24, 2013.
U.S. Appl. No. 13/612,768 Office Action dated Jul. 30, 2015.
U.S. Appl. No. 13/612,768 Office Action dated May 30, 2014.
U.S. Appl. No. 13/612,768 Office Action dated Nov. 17, 2014.
U.S. Appl. No. 13/612,768 Office Action dated Oct. 1, 2013.
U.S. Appl. No. 13/612,778 Office Action dated Apr. 28, 2014.
U.S. Appl. No. 13/612,778 Office Action dated Nov. 7, 2014.
U.S. Appl. No. 13/634,863 Office Action dated Jan. 28, 2015.
U.S. Appl. No. 13/634,863 Office Action dated Sep. 8, 2015.
U.S. Appl. No. 13/794,368 Office Action dated May 8, 2015.
U.S. Appl. No. 13/794,368 Office Action dated Nov. 26, 2014.
U.S. Appl. No. 13/794,368 Office Action dated Sep. 23, 2015.
U.S. Appl. No. 13/801,780 Office Action dated Jun. 5, 2015.
U.S. Appl. No. 13/801,780 Office Action dated Nov. 14, 2014.
U.S. Appl. No. 13/968,313 Office Action dated Jun. 26, 2014.
U.S. Appl. No. 14/244,679 Office Action dated Oct. 23, 2015.
U.S. Appl. No. 14/295,226 Office Action dated May 7, 2015.
U.S. Appl. No. 14/295,226 Office Action dated Oct. 8, 2014.
U.S. Appl. No. 14/295,226 Office Action dated Sep. 9, 2015.
U.S. Appl. No. 14/447,412 Office Action dated Jul. 15, 2015.
U.S. Appl. No. 14/447,412 Office Action dated Mar. 3, 2015.
U.S. Appl. No. 14/530,499 Office Action dated May 14, 2015.
U.S. Appl. No. 14/678,392 Office Action dated Oct. 8, 2015.
U.S. Appl. No. 14/678,392 Office Action dated Sep. 24, 2015.
U.S. Appl. No. 14/796,910 Office Action dated Sep. 25, 2015.
Wake Forest Baptist Medical Center (Wake Forest Physician Reports First Human Recipients of Laboratory-Grown Organs. 2006 pp. 1-2).
Wang et al. Bone marrow mesenchymal stem cells promote cell proliferation and neurotrophic function of Schwann cells in vitro and in vivo. Brain Research 1262:7-15 (2009).

(56)                    References Cited

OTHER PUBLICATIONS

Xu et al. A three-dimensional in vitro ovarian cancer coculture model using a high-throughput cell patterning platform. Biotechnology Journal 6(2):204-212 (2011).

Xu et al. In vivo generation of functional tissues using the inkjet printing technology. Tissue Engineering 13(7):1713-1714 (2007).

Yamauchi et al. A Three-Dimensional Cell Culture Model for Bovine Endometrium: Regeneration of a Multicellular Spheroid Using Ascorbate. Placenta 24:258-269 (2003).

Zhang et al. Characterization of printable cellular micro-fluidic channels for tissue engineering. Biofabrication 5:025004 (2013).

Co-pending U.S. Appl. No. 14/950,567, filed Nov. 24, 2015.

Fujita et al. Fabrication of scaffold-free contractile skeletal muscle tissue using magnetite-incorporated myogenic C2C12 cells. J Tissue Eng Regen Med. 4(6):437-443 (2010).

Hierlihy et al. The post-natal heart contains a myocardial stem cell population. FEBS Letters 530:239-243 (2002).

Liu et al. Design and Development of Three-Dimensional Scaffolds for Tissue Engineering. Chemical Engineering Research and Design 85(7):1051-1064 (2007).

Pearson Education. Human Heart Illustration (2004).

Tanaka et al. A Valved Hepatic Portoduodenal Instestinal Conduit for Biliary Atresia. Ann. Surg. 213(3):230-235 (1991).

Tsang et al. Fabrication of 3D hepatic tissues by additive photopatterning of cellular hydrogels. The FASEB Journal 21(3):790-801 (2007).

U.S. Appl. No. 13/612,778 Office Action dated Nov. 17, 2015.

Rimann, et al., "Additive Verfahren mit biologischen Materialien," cited in NPL18 as Orthopaede vol. 46, Aug. 24, 2014.

Rimann, et al., "Skin bioprinting: an innovative approach to produce standardized skin models on demand," cited in NPL18 as CTI Medtech Event 2012, Luzern, Switzerland, Sep. 24, 2012, retrieved on Apr. 18, 2018 from https://www.zhaw.ch/storage/lsfm/institute-zentren/icbt/tedd/bioprinting-poster.pdf.

Inoue, R., Email "RE: Japanese Patent Application No. 2020-202360, Applicants: Organovo, Inc et al., Country: Japan, Your Ref.: 3731.021JP12, Our Ref.: SK-A1710D1," dated Sep. 21, 2023, 4 pages.

Fujimaru, Y. and Inoue, R., Email Japanese Patent Application No. 2020-202360, Applicants: Organovo, Inc et al., Country: Japan, Your Ref.: 3731.021JP12, Our Ref.: SK-A1710D1,: dated Nov. 27, 2023, 1 page.

* cited by examiner

Bioprinting dermal and epidermal layers with continuous deposition method

Skin tissue design containing dermal and epidermal layers bioprinted with continuous deposition method at 48 hours post print Embedding cellular material into printing surface by aerosol method Fig. 8
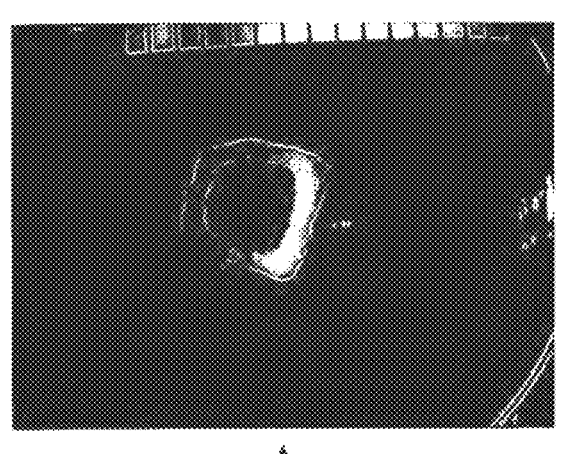
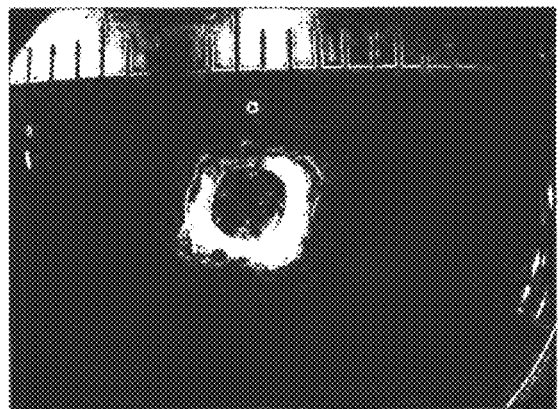
A
B Transwell surface          A          Keratinocytes          B

A                                        B

A          B          E          F

C          D          G          H

A                                          B

*all expression relative to day2

Fig. 21
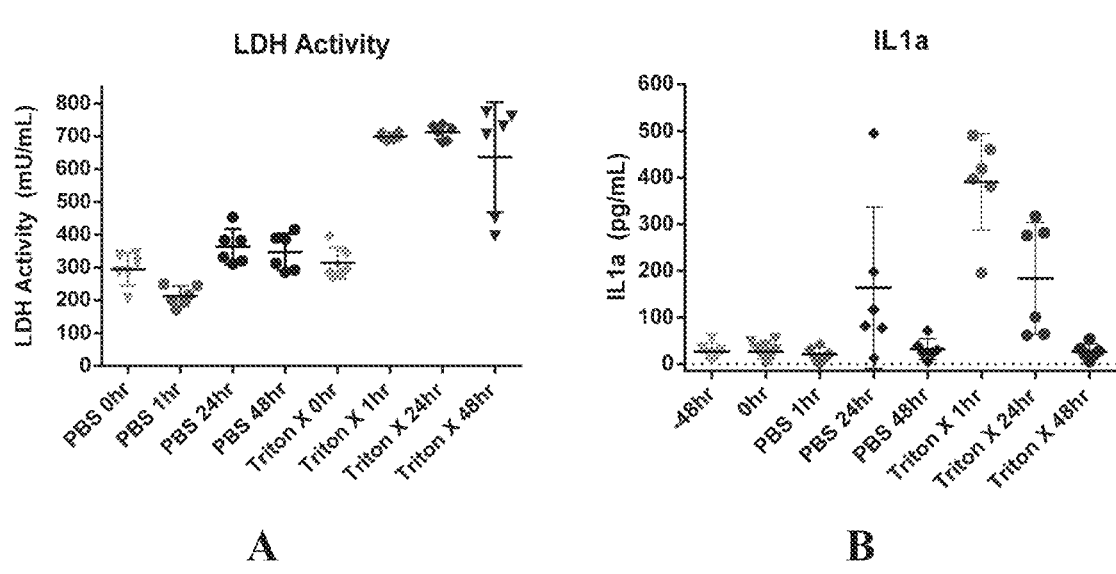
A
B
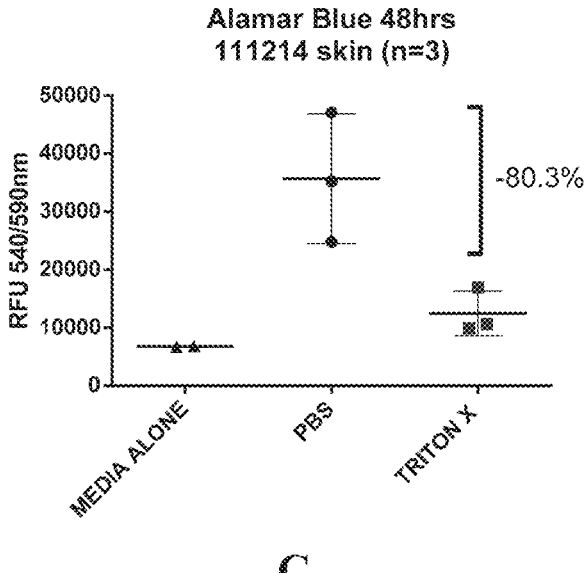
C

Fig. 25
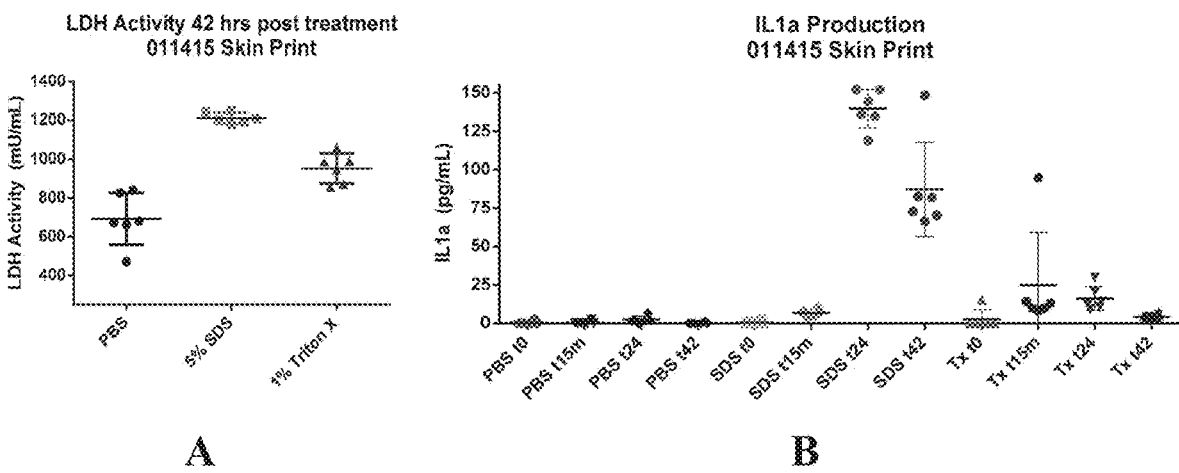
A                                                    B
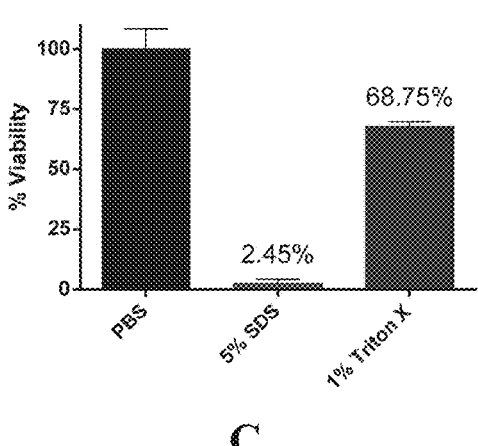
C

Fig. 26

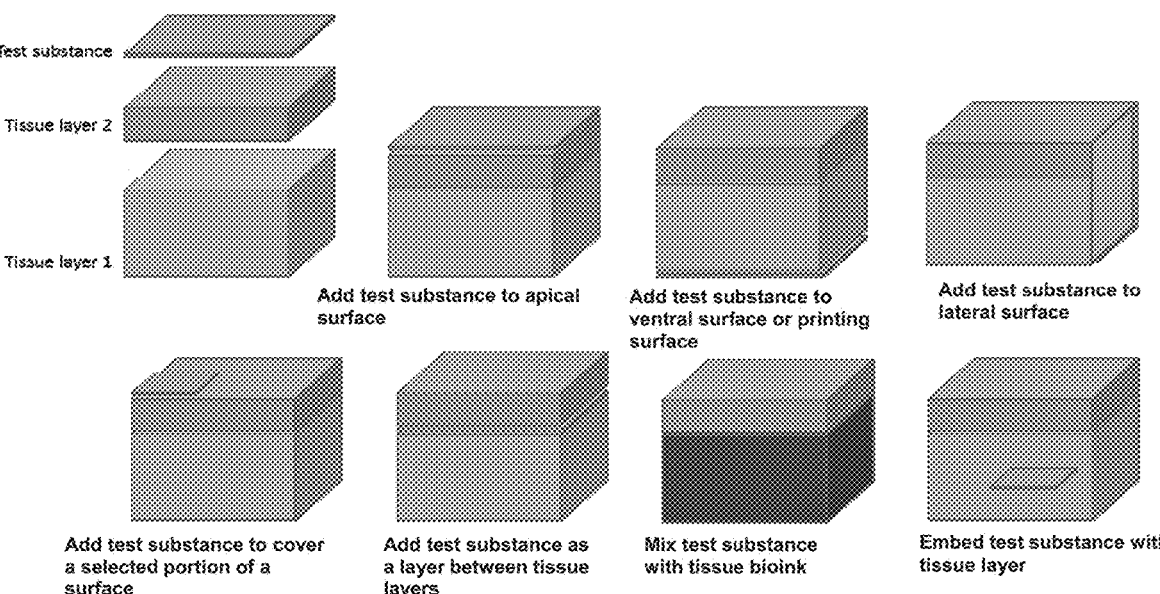

Test substance

Tissue layer 2

Tissue layer 1

Add test substance to apical surface

Add test substance to ventral surface or printing surface

Add test substance to lateral surface

Add test substance to cover a selected portion of a surface

Add test substance as a layer between tissue layers

Mix test substance with tissue bioink

Embed test substance with tissue layer

Fig. 27

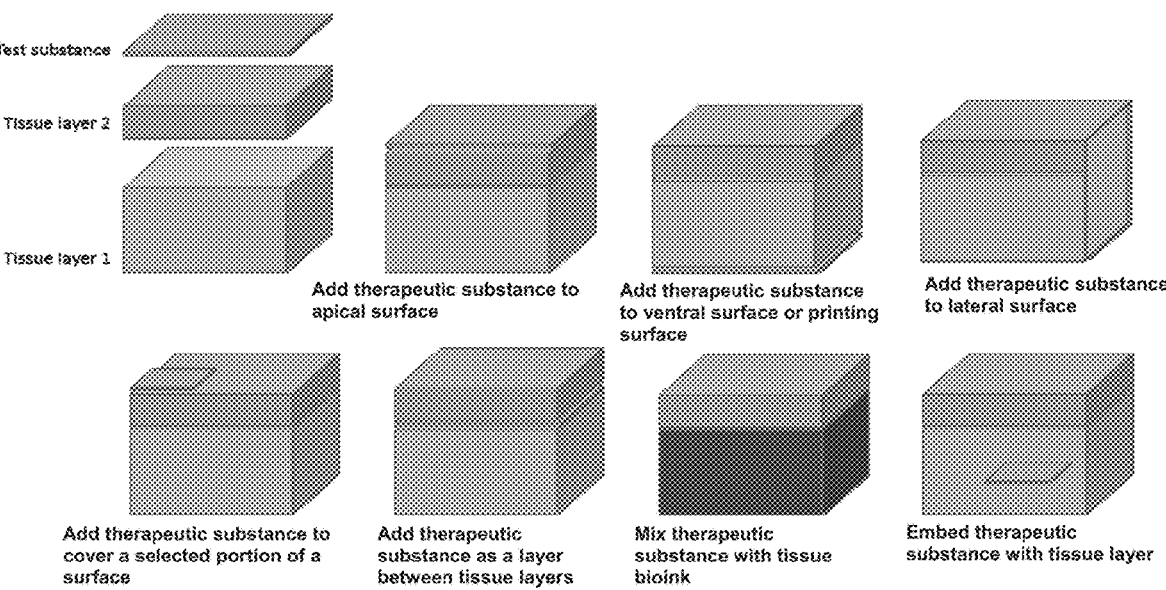

Test substance

Tissue layer 2

Tissue layer 1

Add therapeutic substance to apical surface

Add therapeutic substance to ventral surface or printing surface

Add therapeutic substance to lateral surface

Add therapeutic substance to cover a selected portion of a surface

Add therapeutic substance as a layer between tissue layers

Mix therapeutic substance with tissue bioink

Embed therapeutic substance with tissue layer

A

B

C

D

E

F

G

H

Fig. 29
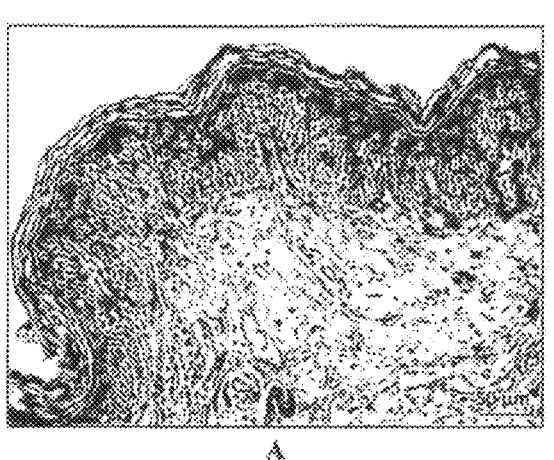
A
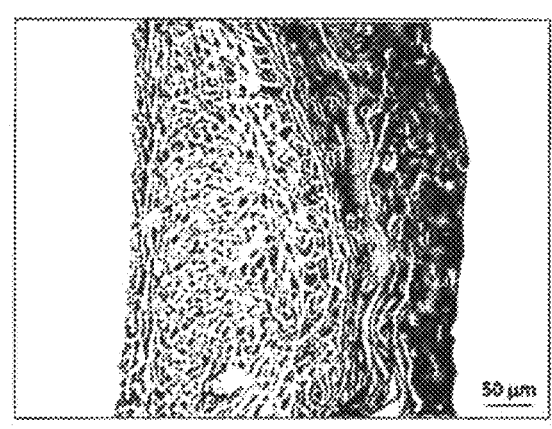
B

ENGINEERED THREE-DIMENSIONAL SKIN TISSUES, ARRAYS THEREOF, AND METHODS OF MAKING THE SAME

CROSS-REFERENCE TO RELATED APPLICATIONS

This application claims the benefit of U.S. Application Ser. No. 62/075,703, filed Nov. 5, 2014 and U.S. Application Ser. No. 62/140,381, filed Mar. 30, 2015, the entire disclosures of which are hereby incorporated herein by reference.

BACKGROUND OF THE INVENTION

The pharmaceutical and cosmetic industries utilize skin models for toxicology screening, barrier function analysis, pigmentation studies, and models for corrosion, irritation, inflammation, and infection.

SUMMARY Of THE INVENTION

Three-dimensional (3D) tissue models for human skin are valuable as an alternative to animal models in both the pharmaceutical and cosmetic industries, and clinically as a therapeutic tissue engraftment. The full thickness human skin models described herein contain a dermal compartment including fibroblasts and connective tissue and an epidermal compartment including stratified keratinocytes. Complexity of the model is optionally increased by incorporating additional specialized cell types, for example, melanocytes can be added into the epidermal layer to model pigmentation. Further, complexity is added by the addition of a hypodermal compartment comprising endothelial cells. An advantage of utilizing skin equivalents developed in a three-dimensional environment is that they are more physiologically relevant than a two-dimensional environment. Cells in a three-dimensional conformation may subsequently differentiate in a different manner than cells cultured in a two-dimensional monolayer, such as an alternative signaling pathway or through different extracellular matrix interactions.

The engineered tissues described herein combine bio-ink formulation technology with continuous deposition printing methods and aerosol spray printing methods (such as ink-jet) to create a novel 3D tissue system to model skin. One major advantage of bioprinting skin compared to existing skin models is the reproducibility of an automated process. Another major advantage of printing skin is the time frame in which a layered structure can be generated. Current skin models often requite a minimum of 3 weeks to obtain a mature, layered structure. The bioprinting approaches described herein overlay sheets of cells simultaneously to create dermal and epidermal layers which are then allowed to mature and differentiate for a defined period of time. The novel skin tissue method presented in this disclosure exhibits a layered architecture within a 12-day period.

In certain embodiments, described herein, is a three-dimensional, engineered, biological skin tissue comprising, a dermal layer comprising a dermal bio-ink, the dermal bio-ink comprising fibroblasts; and an epidermal layer comprising epidermal bio-ink, the epidermal bio-ink comprising keratinocytes, provided the epidermal layer is in contact with the dermal layer to form the three-dimensional engineered, biological skin tissue. In certain embodiments, the dermal layer consists essentially of dermal fibroblasts. In certain embodiments, the epidermal layer consists essentially of keratinocytes. In certain embodiments, the epidermal layer consists essentially of primary keratinocytes. In certain embodiments, the epidermal layer comprises primary keratinocytes. In certain embodiments, the epidermal layer is substantially a monolayer. In certain embodiments, the epidermal layer is multilayered and comprises a plurality of layers of keratinocytes. In certain embodiments, the epidermal layer was bioprinted onto the dermal layer by aerosol spray deposition from a biopinter. In certain embodiments, the epidermal layer was bioprinted onto the dermal layer immediately after bioprinting of the dermal layer. In certain embodiments, the epidermal layer was bioprinted onto the dermal layer after bioprinting and subsequent fusion of the dermal layer. In certain embodiments, the epidermal layer is in continuous contact with the dermal layer. In certain embodiments, greater than 90% of the epidermal layer is in contact with the dermal layer. In certain embodiments, greater than 70% of the epidermal layer is in contact with the dermal layer. In certain embodiments, greater than 50% of the epidermal layer is in contact with the dermal layer. In certain embodiments, the epidermal layer is 20-500 μm thick. In certain embodiments, the epidermal layer is about 150 μm thick. In certain embodiments, the dermal layer is 10-1000 μm thick. In certain embodiments, the dermal layer is about 500 μm thick. In certain embodiments, the epidermal layer comprises an extrusion compound. In certain embodiments, the dermal layer comprises an extrusion compound. In certain embodiments, the epidermal layer comprises melanocytes. In certain embodiments, the epidermal layer consists essentially of keratinocytes and melanocytes. In certain embodiments, the keratinocytes and melanocytes are present in the epidermal layer at a ratio of about 99:1 to about 75:25 keratinocytes to melanocytes. In certain embodiments, the keratinocytes and melanocytes are present in the epidermal layer at a ratio of about 90:10 to about 99:1 keratinocytes to melanocytes. In certain embodiments, the skin tissue comprises secretory cells. In certain embodiments, the secretory cells comprise sebocytes. In certain embodiments, the skin tissue comprises immune cells. In certain embodiments, the immune cells comprise Langerhans cells. In certain embodiments, the skin tissue comprises hair follicle stem cells. In certain embodiment, the skin tissue comprises cancer cells. In certain embodiments, the skin tissue comprises cells derived from induced pluripotent stem cells or embryonic stem cells. In certain embodiments, the skin tissue comprises a basal layer in contact with the dermal layer and the epidermal layer, wherein the basal layer comprises basal keratinocytes. In certain embodiments, cells of the basal layer stain positive for KRT14 (CK14). In certain embodiments, the tissue is substantially free of pre-formed scaffold. In certain embodiments, the fibroblasts and keratinocytes are human cells. In certain embodiments, the dermal layer comprises at least 30% live cells by volume. In certain embodiments, the dermal layer comprises at least 70% live cells by volume. In certain embodiments, the skin tissue comprises a hypodermal layer ventral to the dermal layer, the hypodermal layer comprising a hypodermal bio-ink, the hypodermal bio-ink comprising endothelial cells. In certain embodiments, at least one bio-ink comprises a plurality of organoids, the organoids comprising glandular cells or follicle cells. In certain embodiments, the epidermal bio-ink comprises 0.05 to 50 million cells per ml. In certain embodiments, the epidermal bio-ink comprises 5 to 500 million cells per ml. In certain embodiments, the epidermal bio-ink comprises about 150 million cells per ml. In certain embodiments, the dermal bio-ink comprises 0.05 to 50 million cells per ml. In certain embodiments, the dermal bio-ink comprises 5 to 500 million cells per ml. In certain embodiments, the dermal bio-ink comprises about 150 million cells per ml. In certain embodiments, the skin tissue comprises a test substance, wherein a test substance is a substance under evaluation for its ability to elicit a change in said skin tissue compared to skin tissue not treated with said substance In certain embodiments, the test substance is homogenously present throughout the dermal layer, the epidermal layer or both the dermal and epidermal layer. In certain embodiments, the test substance is heterogeneously present throughout the dermal layer, the epidermal layer or both the dermal and epidermal layer. In certain embodiments, the test substance is in contact with the apical side of the epidermal layer. In certain embodiments, the test substance is between the epidermal and dermal layers, hi certain embodiments, the test substance is between the dermal layer and the printing surface. In certain embodiments, the test substance is in contact with the lateral surface. In certain embodiments, the test substance is within a discreet compartment embedded within the dermal layer, the epidermal layer or both the dermal and epidermal layer. In certain embodiments, the skin tissue comprises a therapeutic substance. In certain embodiments, the therapeutic substance is homogenously present throughout the dermal layer, the epidermal layer or both the dermal and epidermal layer. In certain embodiments, the therapeutic substance is heterogeneously present throughout the dermal layer, the epidermal layer or both the dermal and epidermal layer. In certain embodiments, the therapeutic substance is in contact with the apical side of the epidermal layer. In certain embodiments, the therapeutic substance is between the epidermal and dermal layers. In certain embodiments, the therapeutic substance is between the dermal layer and the printing surface. In certain embodiments, the therapeutic substance is in contact with the lateral surface. In certain embodiments, the therapeutic substance Is within a discreet compartment embedded within the dermal layer, the epidermal layer or both the dermal and epidermal layer. In certain embodiments, the deposition of at least one layer was temporally delayed after the deposition of the previous layer. In certain embodiments, the temporal delay is greater than 10 milliseconds. In certain embodiments, the skin tissue is a genetic chimera. In certain embodiments, the skin tissue is a species chimera. In certain embodiments, the skin tissue is configured in an array to facilitate an in vitro assay, drug-screening assay, or a cosmetic assay. In certain embodiments, the array is configured to allow at least 20 μm of space between each tissue.

In certain embodiments, described herein, is a method of fabricating a three-dimensional, engineered, biological skin tissue, the method comprising: preparing a dermal bio-ink comprising dermal fibroblasts; preparing an epidermal bio-ink comprising keratinocytes; depositing the dermal bio-ink on a surface, depositing the epidermal bio-ink such that the epidermal bio-ink forms a layer on at least one surface of the dermal bio-ink. and maturing the deposited bio-ink in a cell culture media to allow the cells to cohere to form the three-dimensional, engineered, biological skin tissue. In certain embodiments, the dermal bio-ink is deposited by extrusion bioprinting. In certain embodiments, the epidermal bio-ink is deposited by aerosol spray bioprinting. In certain embodiments, the dermal bio-ink is deposited by aerosol spray bioprinting. In certain embodiments, a support material is deposited by aerosol spray bioprinting. In certain embodiments, the dermal bio-ink is at least 30% live cells by volume. In certain embodiments, the epidermal bio-ink is at least 30% live cells by volume. In certain embodiments, the epidermal bio-ink comprises primary keratinocytes. In certain embodiments, the epidermal bio-ink consists essentially of primary keratinocytes. In certain embodiments, the epidermal bio-ink comprises melanocytes. In certain embodiments, the epidermal bio-ink consists essentially of keratinocytes and melanocytes. In certain embodiments, the dermal bio-ink or the epidermal bio-ink comprises cancer cells. In certain embodiments, the dermal bio-ink or the epidermal bio-ink comprises cells derived from induced pluripotent stem cells or embryonic stem cells. In certain embodiments, the method comprises depositing a plurality of organoids into the deposited bio-ink, the organoids comprising glandular cells or follicle cells. In certain embodiments, the method composes preparing a hypodermal bio-ink, the hypodermal bio-ink comprising endothelial cells. In certain embodiments, the hypodermal bio-ink is deposited on the surface on at least one surface followed by deposition of the dermal bio-ink. In certain embodiments, the epidermal bio-ink comprises 0.05 to 50 million cells per ml. In certain embodiments, the epidermal bio-ink comprises 5 to 500 million cells per ml. In certain embodiments, the epidermal bio-ink comprises about 150 million cells per ml. In certain embodiments, the dermal bio ink composes 0.05 to 50 million cells per ml. In certain embodiments, the dermal bio-ink comprises 5 to 500 million cells per ml. In certain embodiments, the dermal bio-ink comprises about 150 million cells per ml. In certain embodiments, the dermal bio-ink comprises an extrusion compound. In certain embodiments, the epidermal bio-ink comprises an extrusion compound. In certain embodiments, the keratinocytes and melanocytes are present in the epidermal bio-ink at a ratio of about 99:1 to about 75:25 keratinocytes to melanocytes. In certain embodiments, the keratinocytes and melanocytes are present in the epidermal bio-ink at a ratio of about 90:10 to about 99:1 keratinocytes to melanocytes. In certain embodiments, either bio-ink comprises secretory cells. In certain embodiments, the secretory cells comprise sebocytes. In certain embodiments, either bio-ink comprises immune cells. In certain embodiments, the immune cells comprise Langerhans cells. In certain embodiments, either bio-ink comprises hair follicle stem cells. In certain embodiments, either bio-ink comprises cancer cells. In certain embodiments, either bio-ink comprises cells derived from induced pluripotent stem cells or embryonic stem cells. In certain embodiments, the method comprises depositing a basal layer in contact with the dermal layer and the epidermal layer, wherein the basal layer comprises a bio-ink comprising basal keratinocytes. In certain embodiments, the tissue is not deposited on a scaffold. In certain embodiments, the fibroblasts and keratinocytes are human cells. In certain embodiments, the method comprises depositing a test substance, wherein a test substance is a substance under evaluation for its ability to elicit a change in skin tissue compared to skin tissue not treated with said substance. In certain embodiments, the test substance is homogenously deposited throughout the dermal layer, the epidermal layer or both the dermal and epidermal layer. In certain embodiments, the rest substance is heterogeneously deposited throughout the dermal layer, the epidermal layer or both the dermal and epidermal layer. In certain embodiments, the test substance is deposited in contact with the apical side of the epidermal layer. In certain embodiments, the test substance is deposited between the epidermal and dermal layers. In certain embodiments, the rest substance is deposited between the dermal layer and the printing surface. In certain embodiments, the test substance is deposited in contact with the lateral surface. In certain embodiments, the test substance is deposited within a discreet compartment embedded within the dermal layer, the epidermal layer or both the dermal and epidermal layer. In certain embodiments, the method comprises depositing a therapeutic substance. In certain embodiments, the therapeutic substance is homogenously deposited throughout the dermal layer, the epidermal layer or both the dermal and epidermal layer. In certain embodiments, the therapeutic substance is heterogeneously deposited throughout the dermal layer, the epidermal layer or both the dermal and epidermal layer. In certain embodiments, the therapeutic substance is deposited in contact with the apical side of the epidermal layer. In certain embodiments, the therapeutic substance is deposited between the epidermal and dermal layers. In certain embodiments, the therapeutic substance is deposited between the dermal layer and the printing surface. In certain embodiments, the therapeutic substance is deposited in contact with the lateral surface. In certain embodiments, the therapeutic substance is deposited within a discreet compartment embedded within the dermal layer, the epidermal layer or both the dermal and epidermal layer. In certain embodiments, the method comprises a temporal delay in the deposition of the epidermal bio-ink onto the dermal bio-ink. In certain embodiments, the delay is greater than 10 milliseconds.

In another aspect described herein, is a three-dimensional, engineered, biological multi-tissue system comprising: a first engineered tissue, the first engineered tissue an engineered skin tissue comprising: a dermal layer comprising a dermal bio-ink, the dermal bio-ink comprising dermal fibroblasts; and an epidermal layer comprising an epidermal bio-ink, the epidermal bio-ink comprising keratinocytes, the epidermal layer in contact with the dermal layer to form the engineered skin tissue; and a second engineered tissue, the second engineered tissue not a skin tissue, the second engineered tissue in physical or fluidic contact with the engineered skin tissue to form the multi-tissue system, wherein at least one component of the second t issue was bioprinted. In certain embodiments, at least one component of the first engineered tissue was bioprinted. In certain embodiments, at least one component of the second engineered tissue was bioprinted. In certain embodiments, the second engineered tissue is a liver tissue, a kidney tissue, a bone tissue, a lung tissue, a vascular tissue, a brain tissue, an intestinal tissue, a stomach tissue, or an esophageal tissue. In certain embodiments, the engineered skin tissue is substantially free of pre-formed scaffold at the time of use In certain embodiments, the second engineered tissue is substantially free of pre-formed scaffold at the time of use.

In certain embodiments, described herein, is a three-dimensional, engineered, biological skin tissue comprising a dermis, the dermis comprising dermal fibroblasts; provided that the dermis was bioprinted from a dermal bio-ink and fused to form the three-dimensional, engineered, biological skin tissue.

In another aspect described herein, is a three-dimensional, engineered, biological skin tissue comprising an epidermis, the epidermis comprising keratinocytes; provided that the epidermis was bioprinted from an epidermal bio-ink and fused to form the three-dimensional, engineered, biological skin tissue.

In another aspect described herein, is a method of fabricating a three-dimensional, engineered, biological skin tissue, the method comprising: preparing a dermal bio-ink comprising dermal fibroblasts; preparing an epidermal bio-ink comprising keratinocytes; depositing the dermal bio-ink on a surface; depositing the epidermal bio-ink such that the epidermal bio-ink forms a layer on at least one surface of the dermal bio-ink, wherein the deposition of the epidermal bio-ink occurs greater than 10 milliseconds and less than 21 days after the after deposition of the dermal bio-ink.

In another aspect, disclosed herein are three-dimensional, engineered, biological skin tissues comprising a dermis, the dermis comprising dermal fibroblasts; provided that the dermis was bioprinted from a dermal bio-ink and fused to form the three-dimensional, engineered, biological skin tissue.

In another aspect, disclosed herein are three-dimensional, engineered, biological skin tissues comprising an epidermis, the epidermis comprising keratinocytes; provided that the epidermis was bioprinted from an epidermal bio-ink and fused to form the three-dimensional, engineered, biological skin tissue.

In another aspect, disclosed herein are three-dimensional, engineered, biological skin tissues comprising a test substance, wherein a test substance is a substance under evaluation for its ability to elicit a change in said skin tissue compared to skin tissue not treated with said substance. The test substance can be homogenously or heterogeneously present throughout the dermal layer, the epidermal layer or both the dermal and epidermal layer. The test substance can be in contact with the apical side of the epidermal layer, between the epidermal and dermal layers, between the dermal layer and the printing surface, within a discreet compartment embedded within the dermal layer, the epidermal layer or both the dermal and epidermal layer, or in contact with any lateral surface of the tissue.

In another aspect, disclosed herein are three-dimensional, engineered, biological skin tissues comprising a therapeutic substance. The therapeutic substance can be homogenously or heterogeneously present throughout the dermal layer, the epidermal layer or both the dermal and epidermal layer The therapeutic substance can be in contact with the apical side of the epidermal layer, between the epidermal and dermal layers, between the dermal layer and the printing surface, within a discreet compartment embedded within the dermal layer, the epidermal layer or both the dermal and epidermal layer, or in contact with any lateral surface of the tissue.

In another aspect, disclosed herein are three-dimensional, engineered, biological skin tissues constructed with a temporal delay in deposition between the dermal and epidermal layers.

In another aspect disclosed herein are methods of fabricating a three-dimensional, engineered, biological skin tissue, the method comprising: preparing a dermal bio-ink comprising dermal fibroblasts; preparing an epidermal bio-ink comprising keratinocytes; depositing the dermal bio-ink onto a surface; depositing the epidermal bio-ink such that the epidermal bio-ink forms a layer on at least one surface of the dermal bio-ink, and maturing the deposited bio-ink in a cell culture media to allow the cells to cohere to form the three-dimensional engineered, biological skin tissue. In certain embodiments, the dermal bio-ink is deposited by bioprinting, the bioprinting comprising extrusion of a semi-solid or solid dermal bio-ink. In certain embodiments, the concentration of the dermal bio-ink is between 5 and 500 million cells per mL. In certain embodiments, the dermal bio-ink is deposited by bioprinting, the bioprinting comprising ink-jetting or spraying a liquid dermal bio-ink. In certain embodiments, the concentration of the dermal bio-ink is between 0.05 million and 50 million cells per ml. In certain embodiments, the epidermal bio-ink is deposited by bioprinting, the bioprinting comprising extrusion of a semi-solid or solid epidermal bio-ink. In certain embodiments, the concentration of the epidermal bio-ink is between 5 and 500 million cells per mL. In certain embodiments, the epidermal bio-ink is deposited by bioprinting, the bioprinting comprising ink-jetting or spraying a liquid epidermal bio-ink. In certain embodiments, the concentration of the epidermal bio-ink is between 0.05 million and 50 million cells per mL. In certain embodiments, the dermal bio-ink comprises primary human fibroblasts. In certain embodiments, the dermal bio-ink consists essentially of primary human fibroblasts. In certain embodiments, the epidermal bio-ink comprises primary human keratinocytes. In certain embodiments, the epidermal bio-ink consists essentially of primary human keratinocytes. In certain embodiments, the epidermal bio-ink comprises melanocytes. In certain embodiments, the epidermal bio-ink consists essentially of keratinocytes and melanocytes. In certain embodiments, the keratinocytes and melanocytes are present in the epidermal bio-ink at a ratio of about 90:10 to about 99:1 keratinocytes to melanocytes. In certain embodiments, the method comprises depositing a plurality of organoids into the deposited bio-ink, the organoids comprising sebocytes, glandular cells, or follicle cells. In certain embodiments, the method comprises preparing a hypodermal bio-ink, the hypodermal bio-ink comprising endothelial cells. In certain embodiments, the hypodermal bio-ink is deposited on the surface prior to deposition of the dermal bio-ink. In certain embodiments, either bio-ink comprises cancer cells. In certain embodiments, the method comprises depositing a test substance, wherein a test substance is a substance under evaluation for its ability to elicit a change in skin tissue compared to skin tissue not treated with said substance. In certain embodiments, the test substance is deposited on the apical surface of the epidermal layer. In certain embodiments, the epidermal bio-ink is deposited on the at least one surface of the dermal bio-ink before the dermal bio-ink is matured. In certain embodiments, the epidermal bio-ink is deposited after the dermal bio-ink, and there is greater than 100 ms of delay between depositing the dermal and the epidermal bio-ink. In certain embodiments, the deposited bio-inks are matured for at least 24 hours. In certain embodiments, any of the deposited bio-inks contain at least 70% live cells by volume at least 7 days post deposition or any of the bio-inks, provided that the cells were not treated with a test substance. In certain embodiments, the tissue comprises cells that originated from two different donors. In certain embodiments, mature tissue innervation, perfusable lymphatic tissue, and/or perfusable vasculature were not formed during fabrication or maturation and are absent from tire engineered tissue.

In another aspect, disclosed herein are methods of fabricating a three-dimensional, engineered, biological skin tissue, the method comprising preparing a dermal bio-ink comprising dermal fibroblasts, wherein the bio-ink is a semi-solid or solid; wherein the concentration of the dermal bio-ink is between 5 and 500 million cells per mL; preparing an epidermal bio-ink comprising keratinocytes, wherein the concentration of the epidermal bio-ink is between 0.05 million and 50 million cells per mL; depositing the dermal bio-ink onto a surface by extrusion of the dermal bio-ink; depositing the epidermal bio-ink by ink-jetting or spraying the epidermal bio-ink such that the epidermal bio-ink forms a layer on at least one surface of the dermal bio-ink; and maturing the deposited bio-ink in a cell culture media to allow the cells to cohere to form the three-dimensional, engineered, biological skin tissue.

In another aspect, disclosed herein are methods of fabricating a three-dimensional, engineered, biological skin tissue, the method comprising: preparing a dermal bio-ink comprising dermal fibroblasts, wherein the bio-ink is a semi-solid or solid; wherein the concentration of the dermal bio-ink is between 5 and 500 million cells per mL; preparing an epidermal bio-ink comprising keratinocytes; wherein the bio-ink is a semi-solid or solid; wherein the concentration of the epidermal bio-ink is between 5 and 500 million cells per mL; depositing the dermal bio-ink onto a surface by extrusion of the dermal bio-ink: depositing the epidermal bio-ink by extrusion of the epidermal bio-ink such that the epidermal bio-ink forms a layer on at least one surface of the dermal bio-ink; and maturing the deposited bio-ink in a cell culture media to allow the cells to cohere to form the three-dimensional, engineered, biological skin tissue.

BRIEF DESCRI PTION OF THE DRAWINGS

Figure 3:
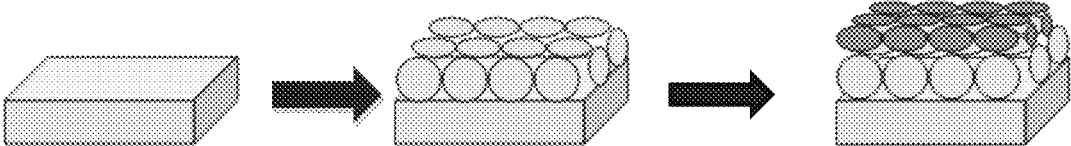

FIG. 3 shows a non-limiting example of a schematic flow diagram depicting a method of fabricating a skin tissue; in this ease, a method of fabricating a layered engineered skin tissue including depositing, using continuous deposition techniques, a layer of dermal cells onto a surface arid depositing, using continuous deposition bioprinting techniques, a layer of epidermal cells onto the layer of dermal cells.

Figure 4:
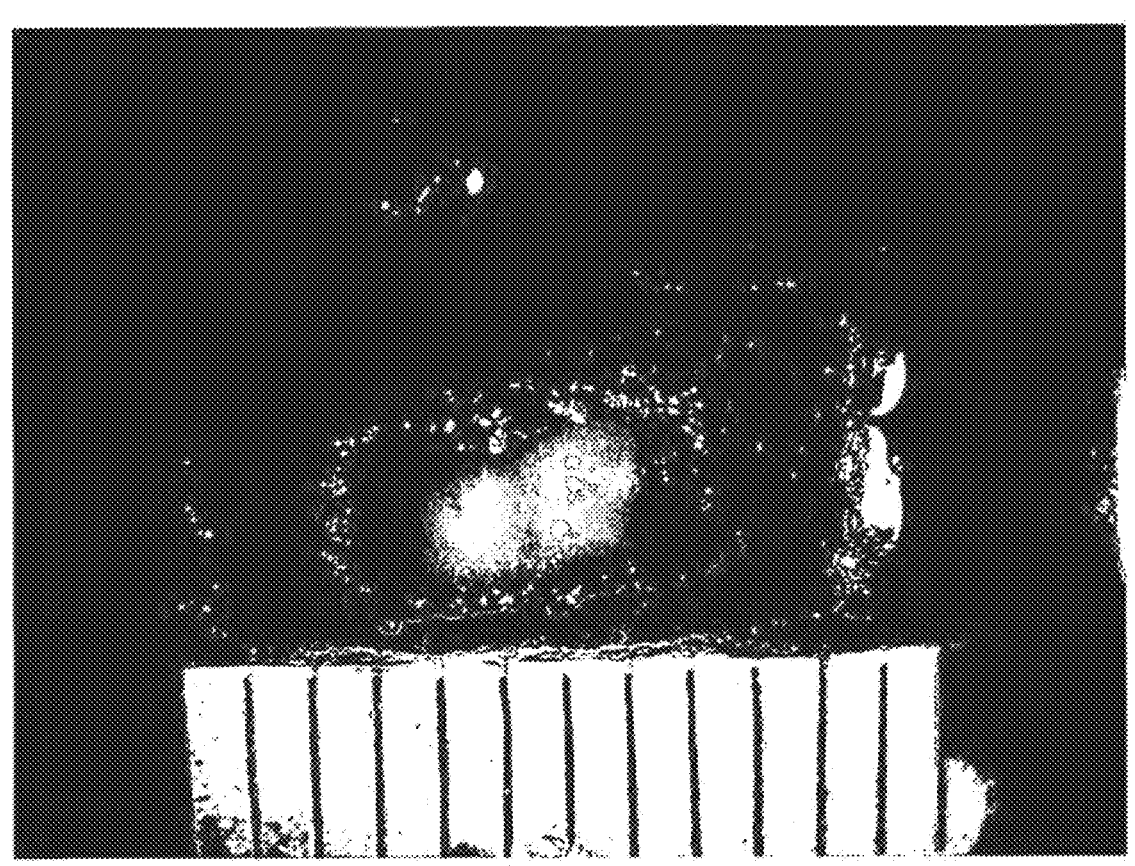
Figure 5:
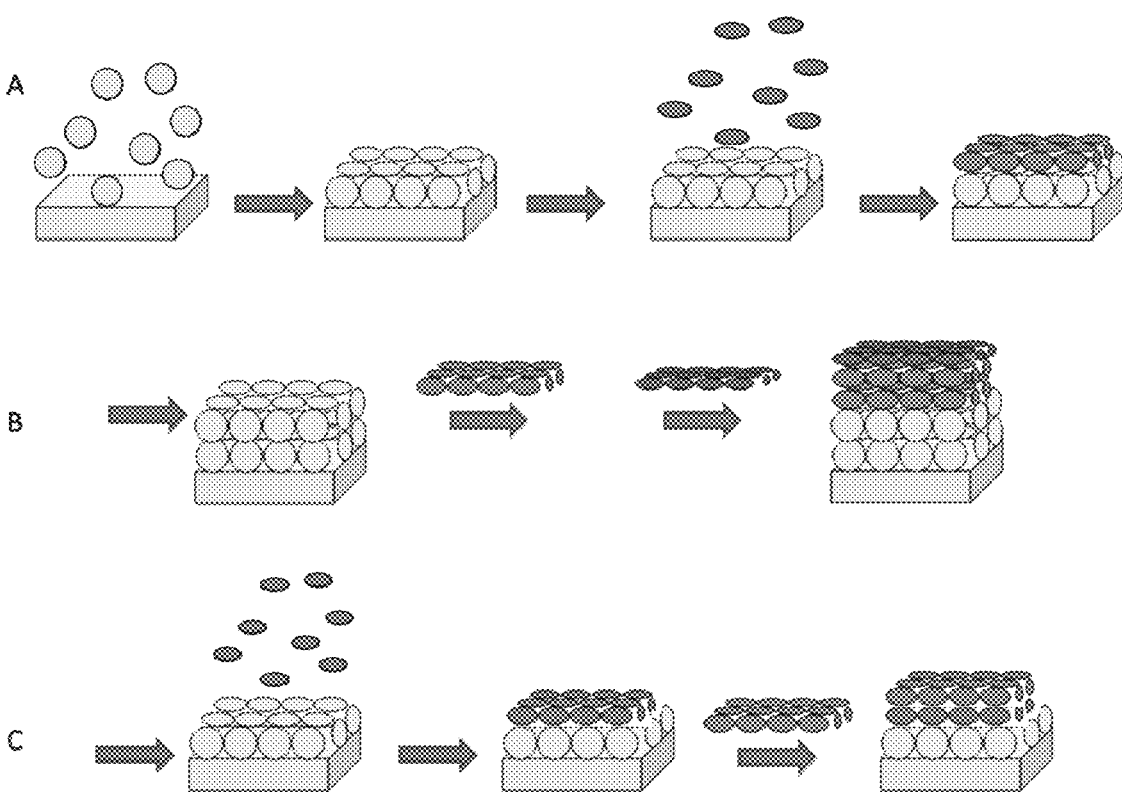

FIG. 4 shows a non-limiting example of a macroscale photograph of an engineered skin tissue; in this ease, an engineered skin tissue including dermal and epidermal layers, deposited by continuous deposition bioprinting techniques, at 48 hours post printing, FIG. 5 shows a non-limiting example of a schematic flow diagram depicting a method of fabricating a skin tissue; in this case, a method of fabricating a layered engineered skin tissue including depositing, using continuous deposition bioprinting techniques, a layer of dermal cells onto a surface and depositing, using aerosol spray bioprinting techniques, using a monolayer (A), or a plurality of layers of epidermal cells (B) onto the layer of dermal cells. In (C) another embodiment is shown, a layer of dermal cells is bioprinted onto a surface using continuous deposition bioprinting techniques followed by addition of a layer of extracellular matrix, followed by addition of a monolayer or a plurality of layers of epidermal cells.

Figure 6:
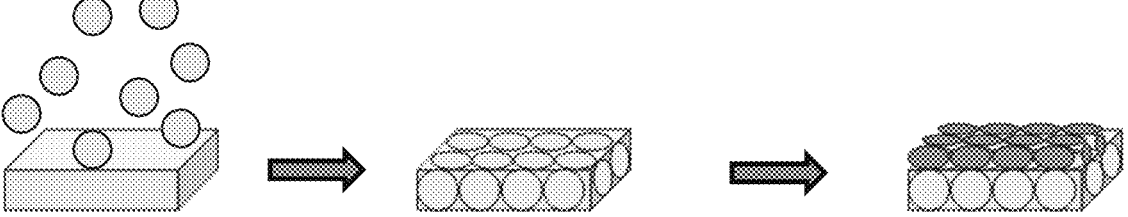

FIG. 6 shows a non-limiting example of a schematic flow diagram depicting a method of fabricating a skin tissue: in this case, a method of fabricating a layered engineered skin tissue including depositing, using ink jet deposition bioprinting techniques, to embed a layer of dermal cells into a surface and depositing, using aerosol spray bioprinting or continuous deposition techniques, epidermal cells onto the layer of dermal cells.

Figure 7:
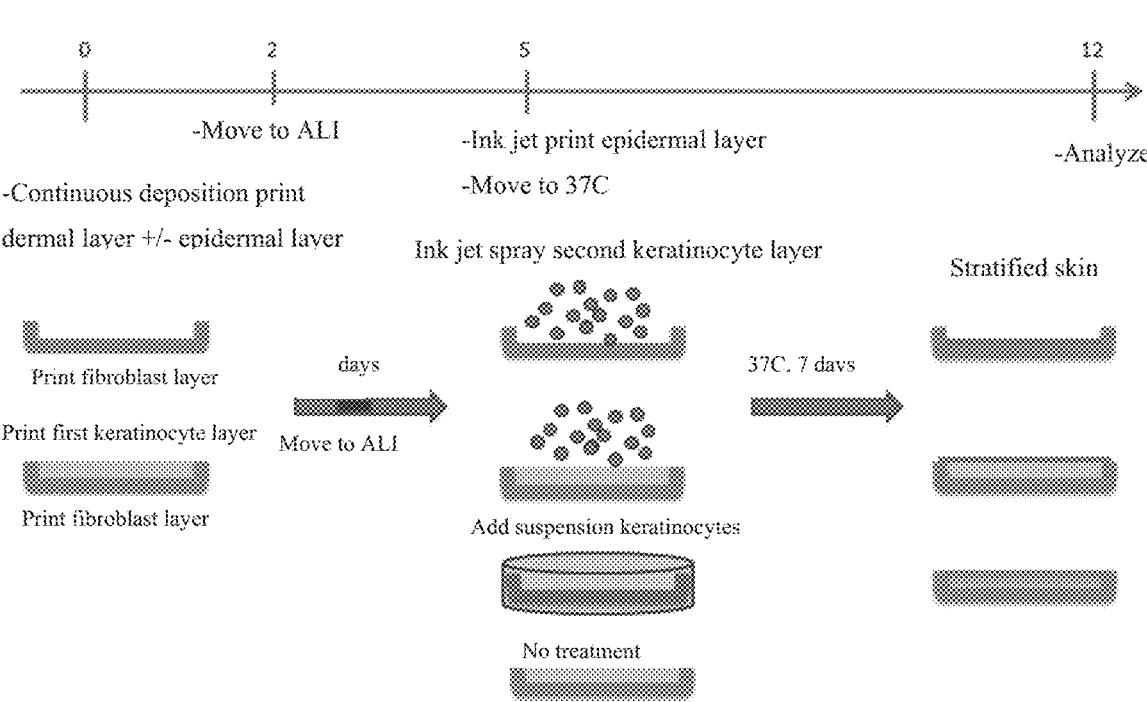

FIG. 7 shows a non-limiting example of an experimental design; in this case, an experimental design depicting a variety of bioprinting techniques used to achieve the engineered skin tissues described herein.

FIG. 8 shows non-limning examples of macroscale photographs of an engineered skin tissue; in this case, an engineered skin tissue including a dermal layer, immediately post printing (A) and 1 day post printing (B).

Figure 9:
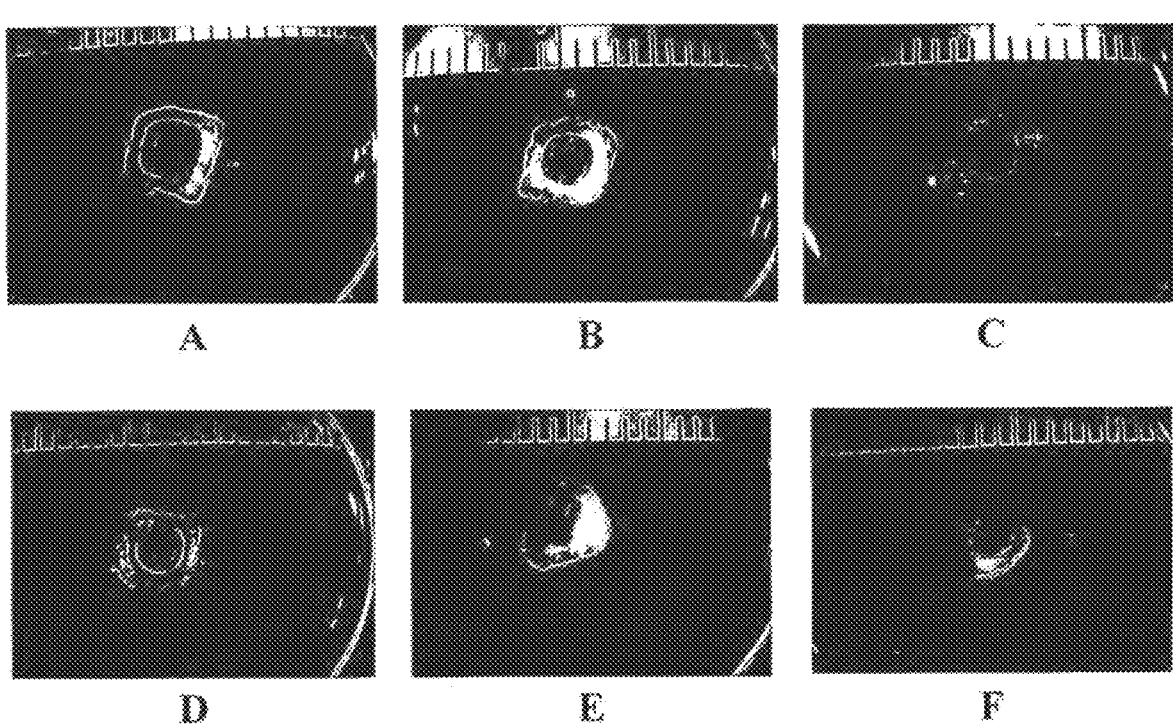

FIG. 9 shows non-limiting examples of macroscale photographs of an engineered skin tissue; in this case, an engineered full-thickness skin tissue, immediately post printing of the dermal layer (A), 24 hours post printing of the dermal layer (B), immediately post printing of the epidermal layer (C), 24 hours post printing of the epidermal layer (D), 96 hours post exposure of the tissue to the air-liquid interface (E), and 216 hours post exposure of the tissue to the air-liquid interface (F).

Figure 10:
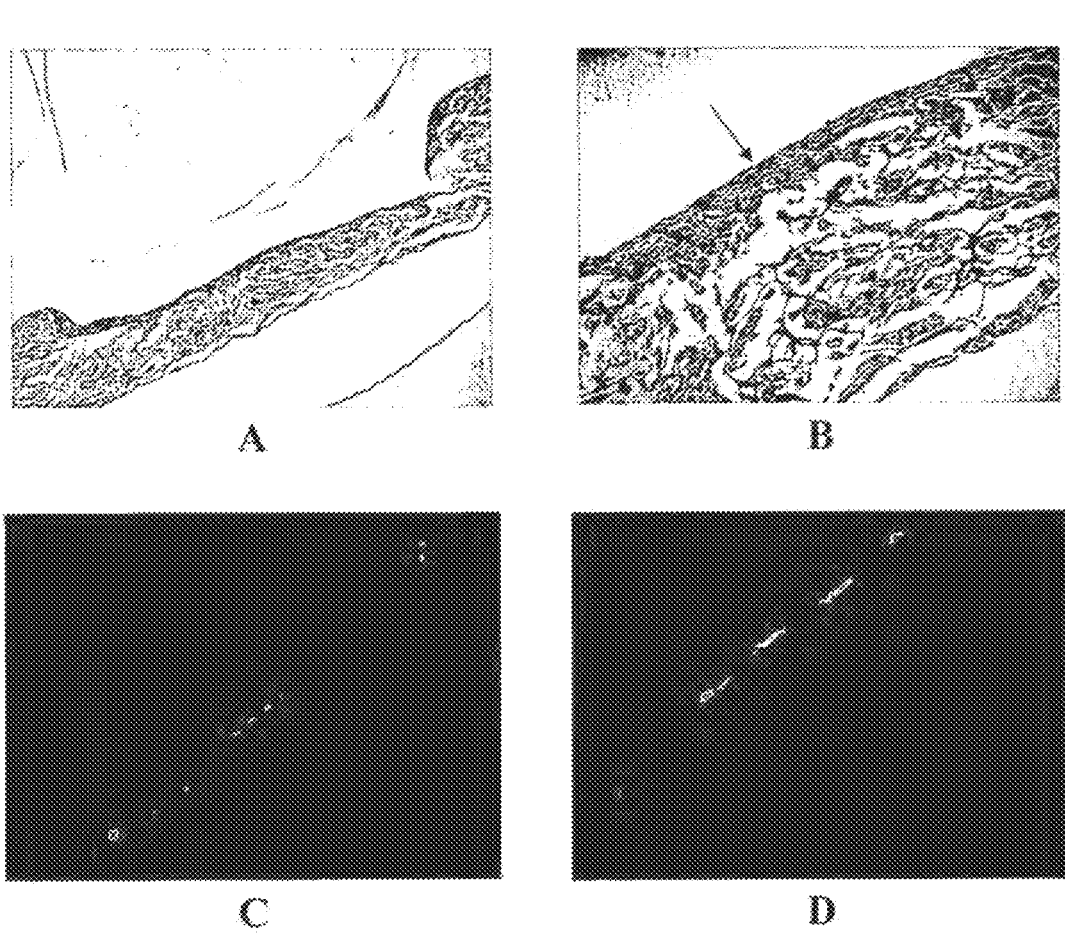

FIG. 10 shows non-limiting examples of photomicrographs of engineered skin tissues; in this case, photomicrographs depicting H&E staining (A and B) and immunohistochemistry for visualization of CK14 (C and D) of the tissues of Example 1 at day 2 post printing.

Figure 11:
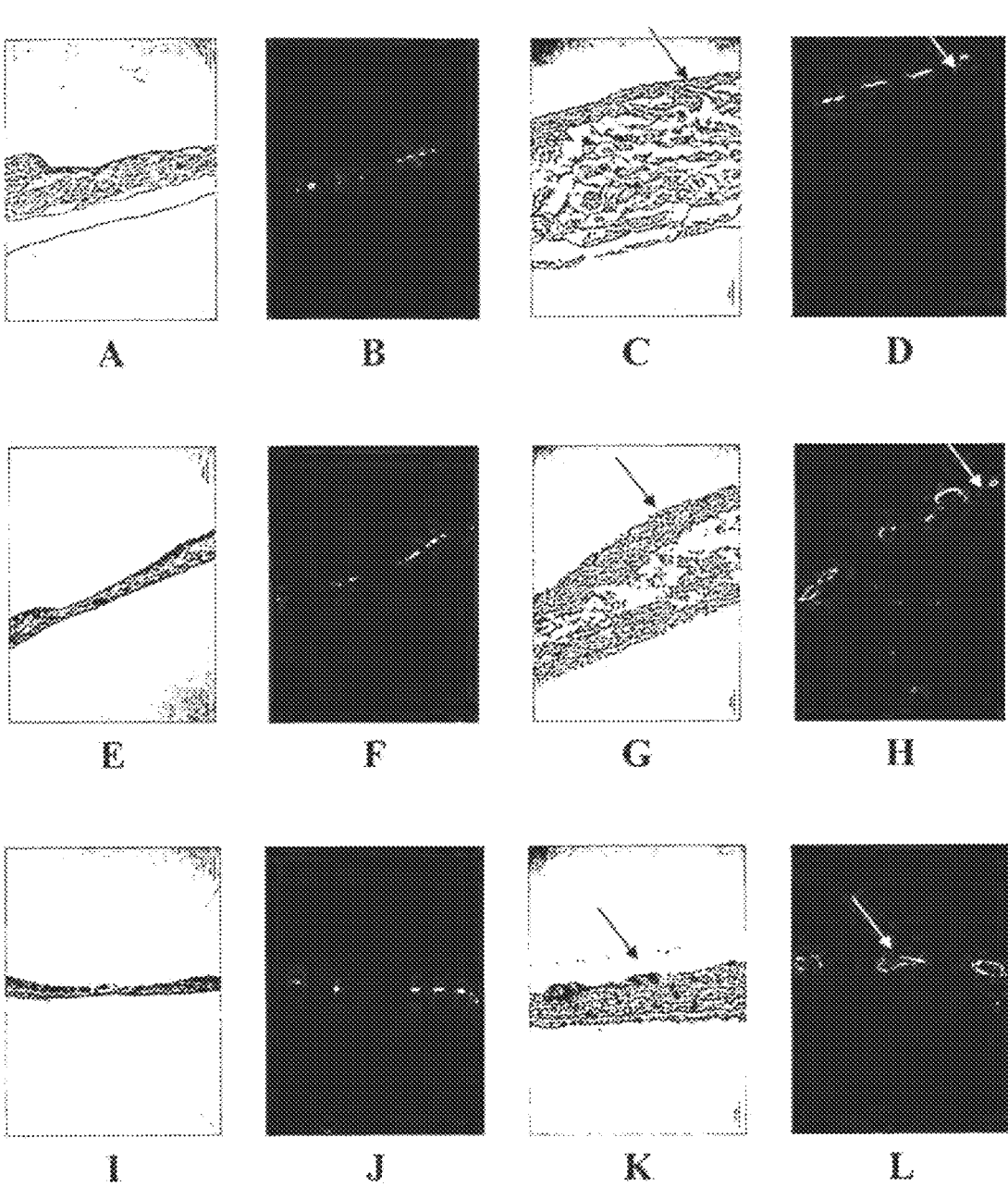

FIG. 11 shows non-limiting examples of photomicrographs of engineered skin tissues; in this case, photomicrographs depicting H&E staining (A, C, E, G, I, and K) and immunohistochemistry for visualization of CK14 (B, D, F, H, J, and L) of the tissues of Example 1 at day 2 post printing (A-D), day 4 post printing (E-H), and day 8 post printing (I-L).

Figure 12:
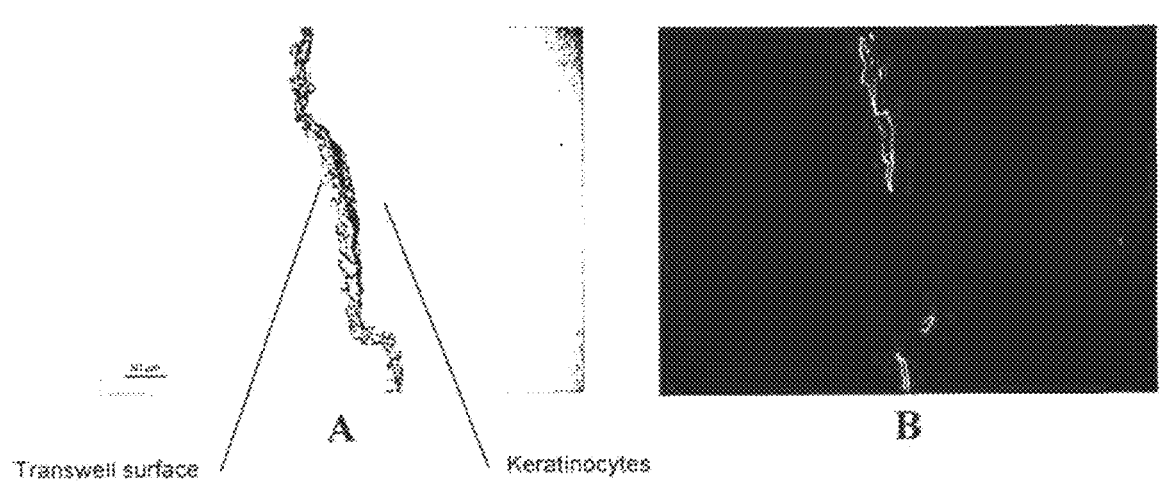

FIG. 12 shows non-limiting examples of photomicrographs of engineered skin tissues; in this case, photomicrographs depicting H&E staining (A) and immunohistochemistry for visualization of CK14 (B) of epithelial layers deposited by aerosol spray bioprinting directly only a surface.

Figure 13:
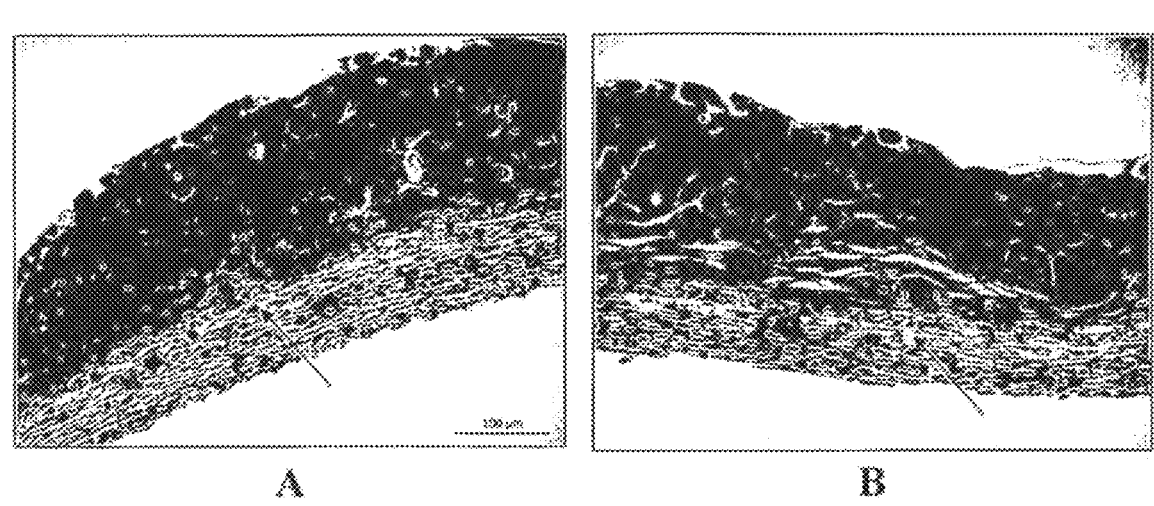

FIG. 13 shows non-limiting examples of photomicrographs of engineered skin tissues; in this case, photomicrographs depicting H&E staining of two of the tissues of Example 2 at day 12 post printing (first tissue: A; second tissue B) (arrows indicate distinct basal layer).

Figure 14:
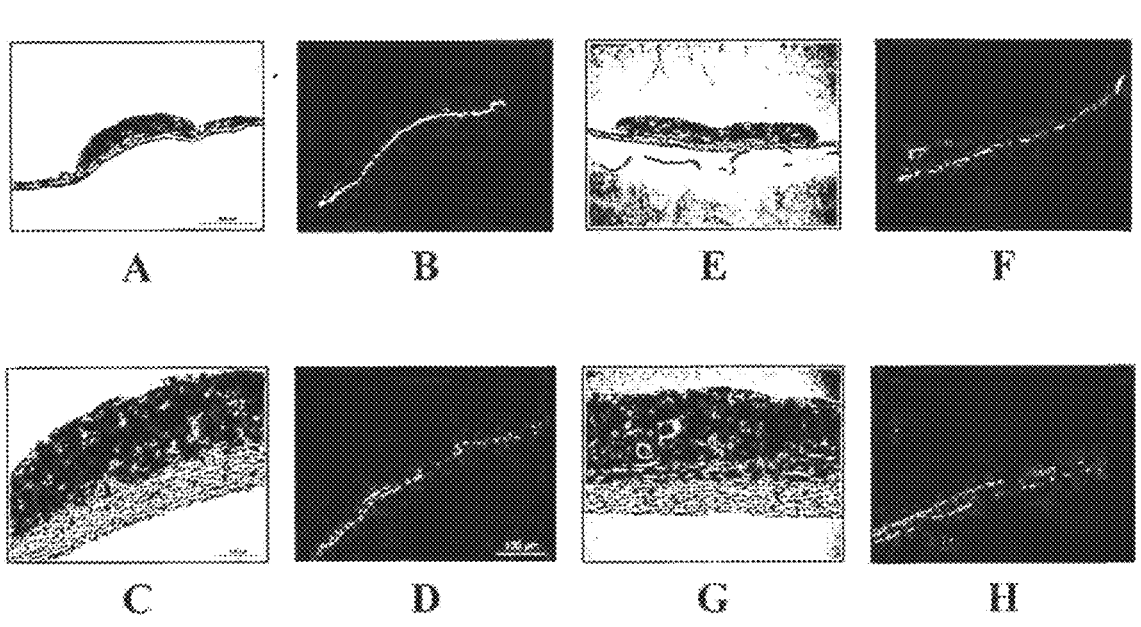

FIG. 14 shows non-limiting examples of photomicrographs of engineered skin tissues; in this case, photomicrographs depicting H&E staining (A. C, E, and G) and immunohistochemistry for visualization of CK14 (B, D, F, and H) of two of the tissues of Example 2 at day 12 post printing (first tissue: A-D; second tissue E-H).

Figure 15:
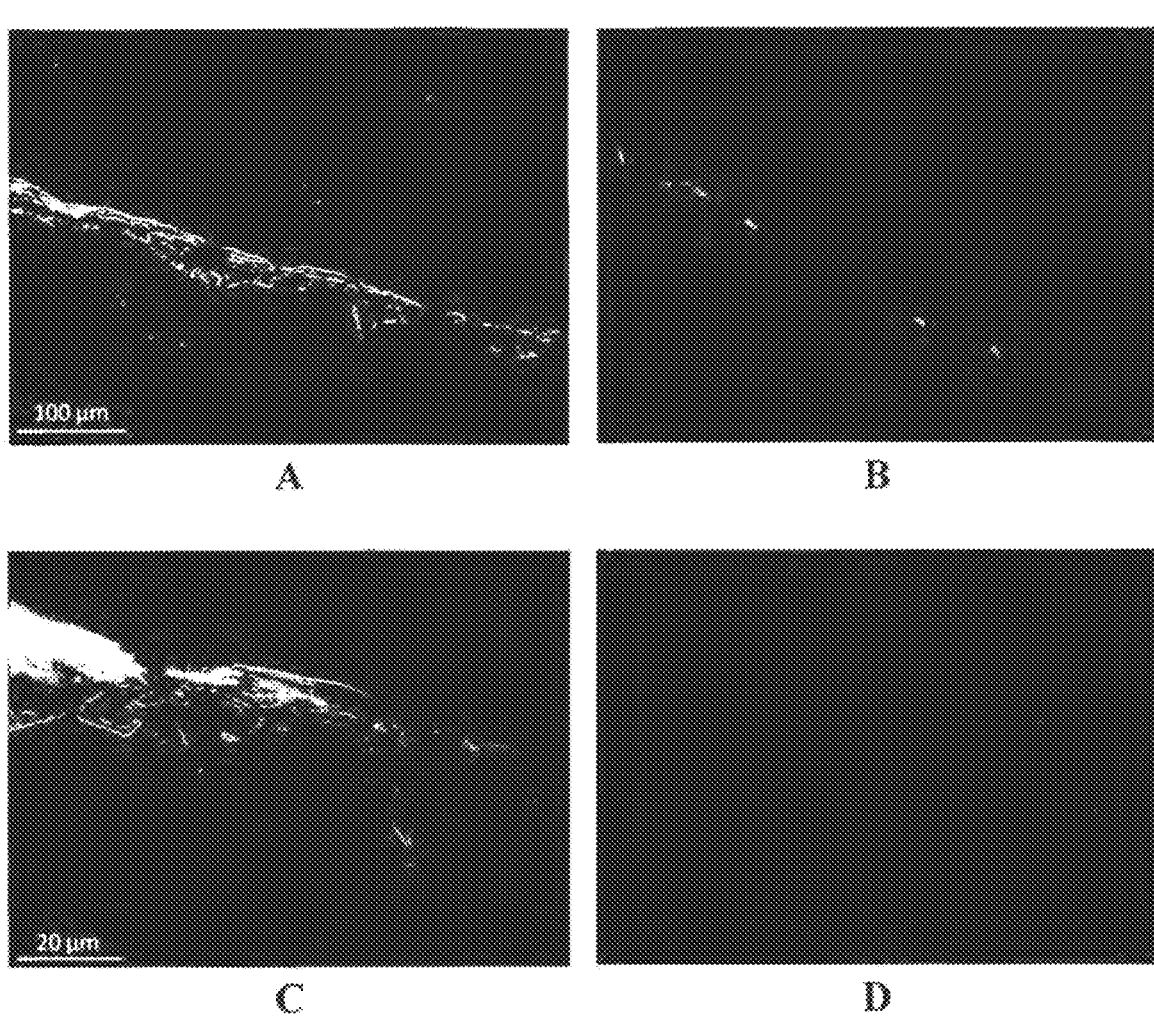

FIG. 15 shows non-limiting examples of photomicrographs of engineered skin tissues; in this case, photomicrographs depicting immunohistochemistry for visualization of CK5/IVL/Dapi (A and C) and CK10/Dapi (B and D) of a third tissue of Example 2 at day 12 post printing.

Figure 16:
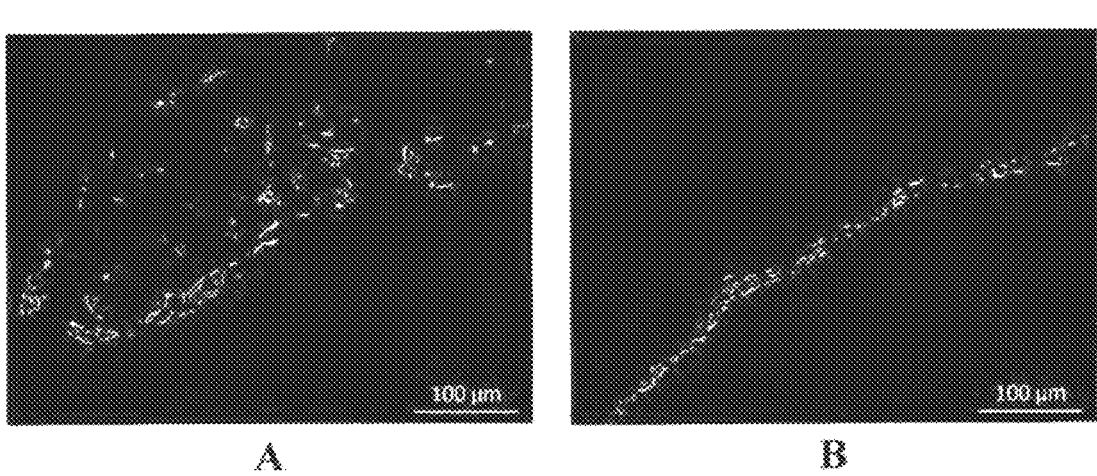

FIG. 16 shows non-limiting examples of photomicrographs of engineered skin tissues; in this case, photomicrographs depicting a comparison of tissues bioprinted using different methodologies (first tissue at day 10 (A); second tissue at day 12 ( B)).

Figure 17:
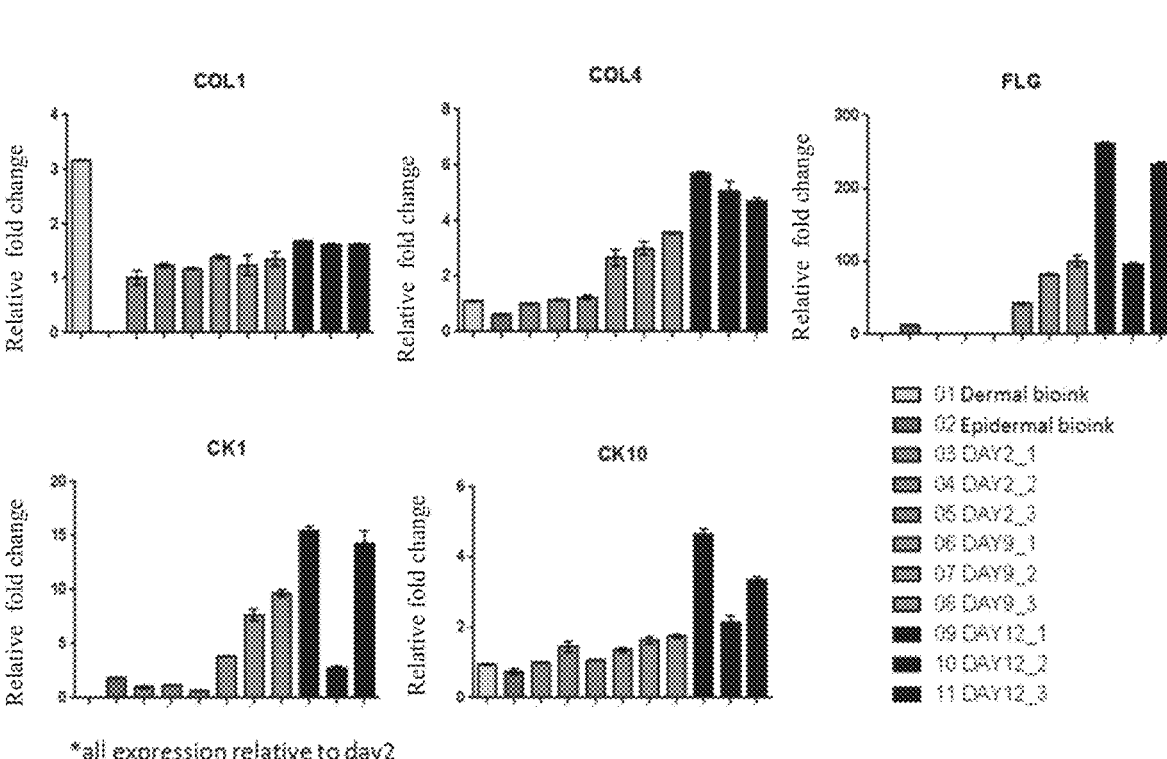

FIG. 17 shows exemplary experimental data on gene expression within the engineered skin tissues described herein; in this case, a gene expression data for collagen (COL1 and COL4), filaggrin (FLG), and cytokeratin (CK1 and CK10).

Figure 18:
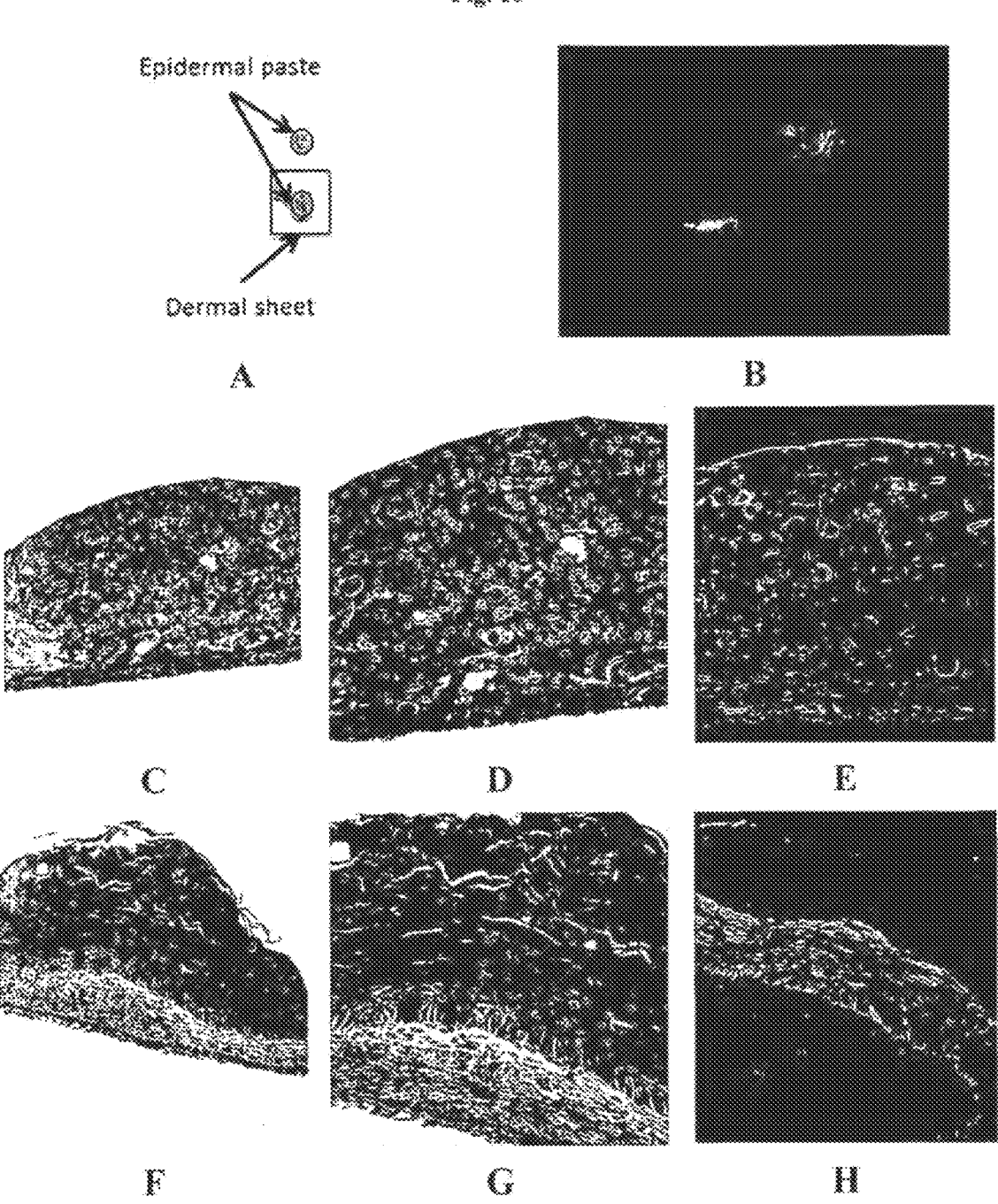

FIG. 18 shows the effect that dermal tissue has on epidermal organization and differentiation. (A) Is a schematic of the experiment. (B) shows a macroscopic view of the printed tissue. (C and F) low magnification of H&E stained cells printed without (C) or with (F) dermal paste (bio-ink), (D and G) higher magnification of H&E stained cells printed without (D) or with (G) dermal paste (bio-ink). Distinct layers of differentiated keratinocytes are visualized by simultaneously staining for a basal cell marker CK5 (green) and involucrin (IVL, red), a later stage differentiation marker of granular and cornified keratinocytes in cells printed without (E) or with dermal paste (bio-ink) (H).

Figure 19:
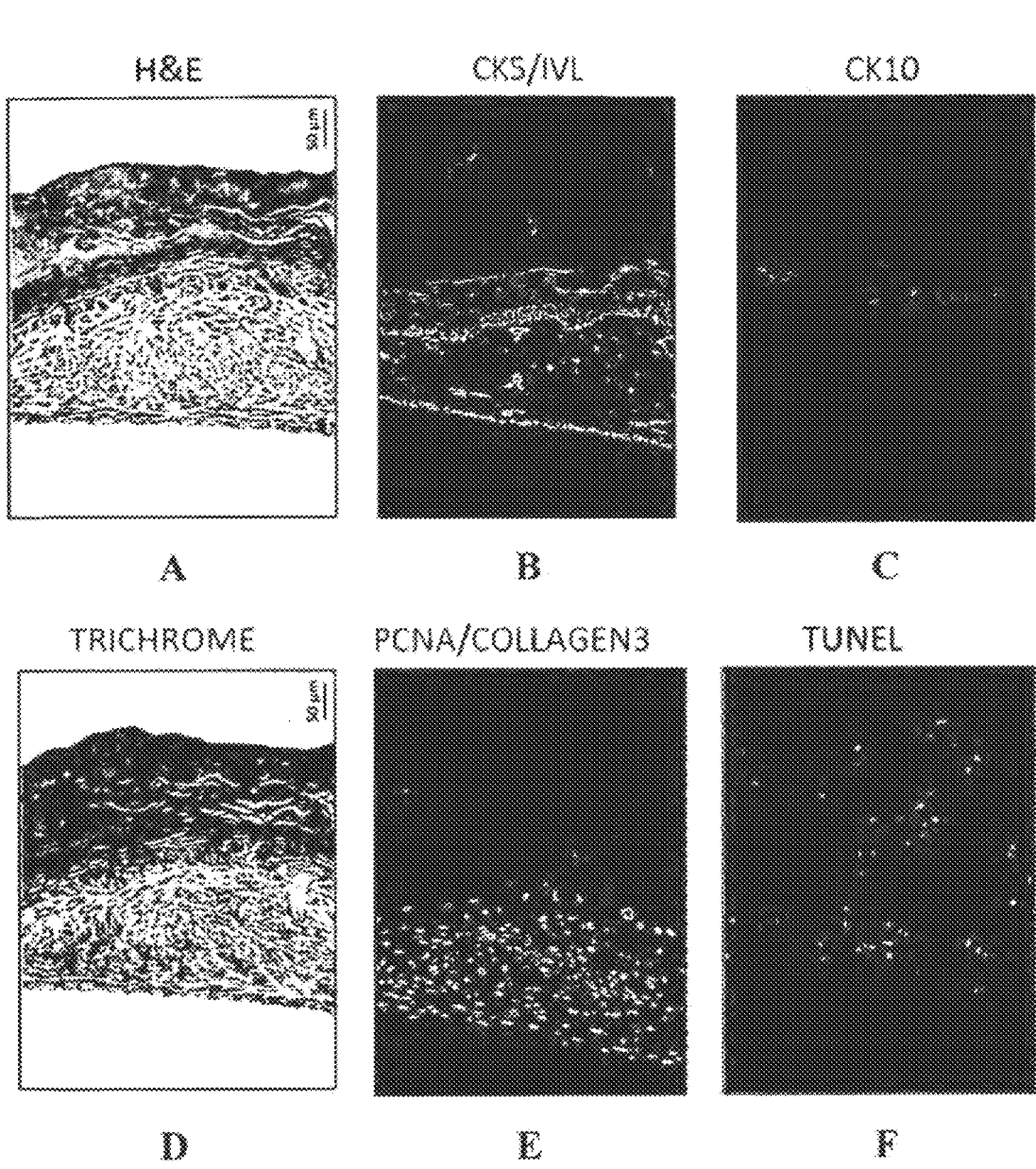

FIG. 19 histological analysis of bioprinted skin tissue at day 12. Shown is H&E staining (A), staining for CK5/IVL (B), CK10 (C), Trichrome stain (D), PCNA and Collagen (E) and TUNEL staining (F).

Figure 20:
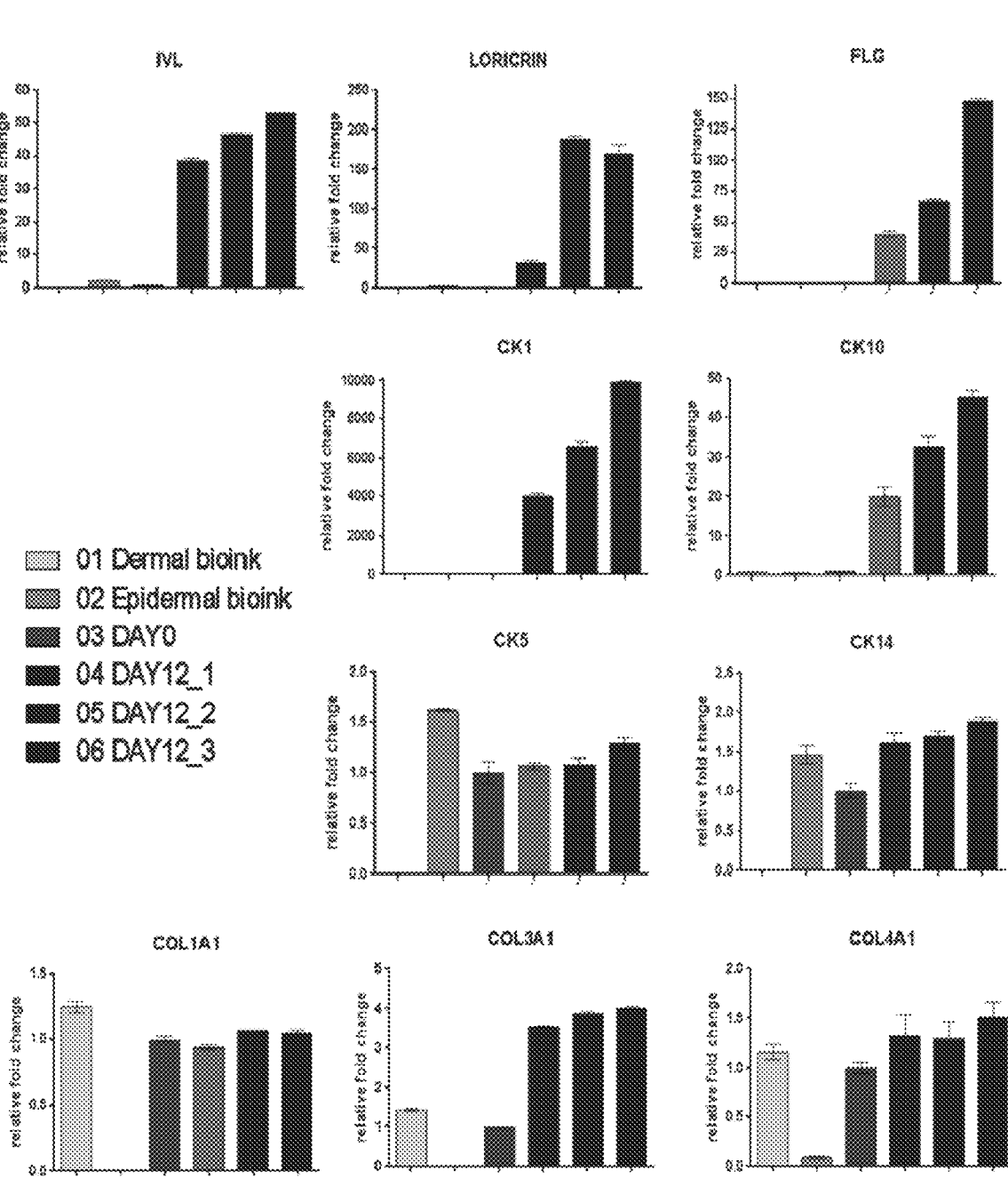

FIG. 20 shows gene expression analysis of bioprinted skin tissue at day 12.

FIG. 21 Shows LDH activity (A), IL-1α production (B) and alamar blue assay (C) of bioprinted skin tissues treated with 1% Triton X-100™.

Figure 22:
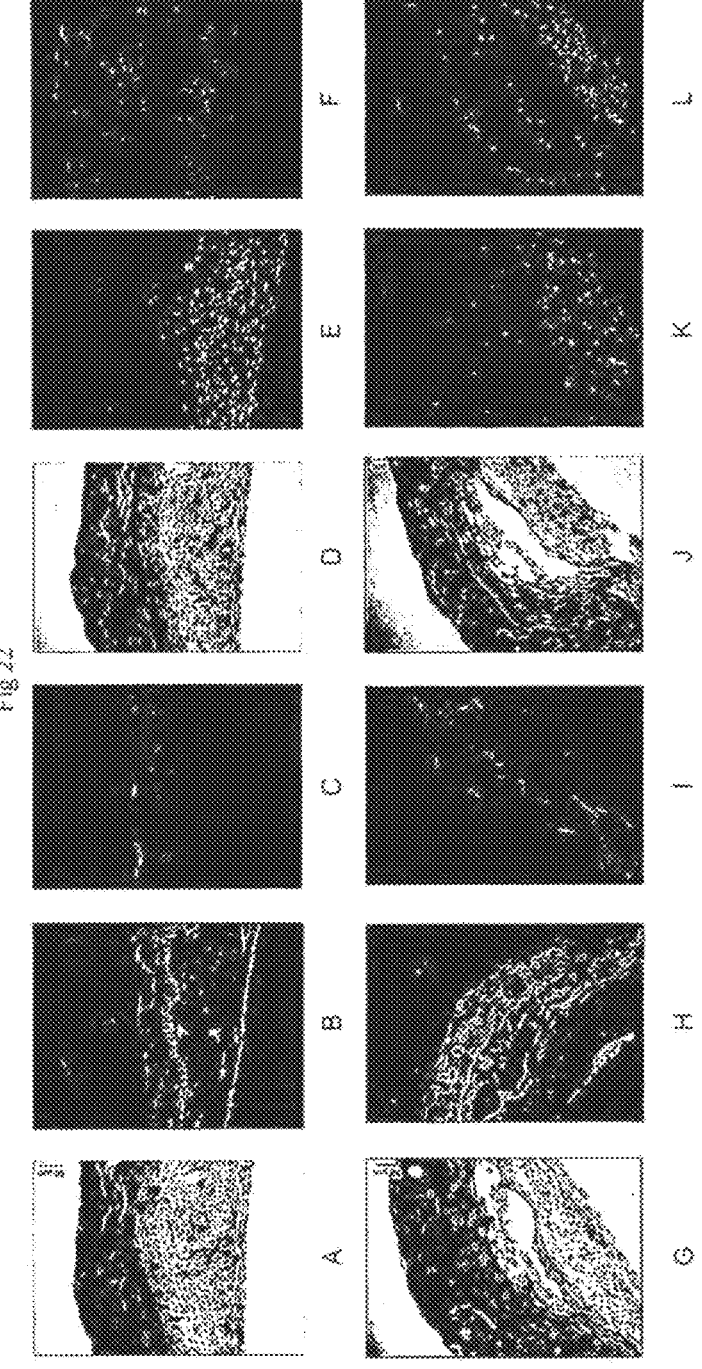

FIG. 22 shows histological analysis of bioprinted skin tissues treated with 1% Triton X-100™ (G, H, I, J, K, L) compared to PBS treated controls (A, B, C, D, E, F). Cells were stained for H&E (A and G), CK5 (green) and IVL (red) (B and H), CK10 (C and I), Trichrome (D and J), PCNA (green) and Collagen (red) (E and K) and TUNEL (F and L).

Figure 23:
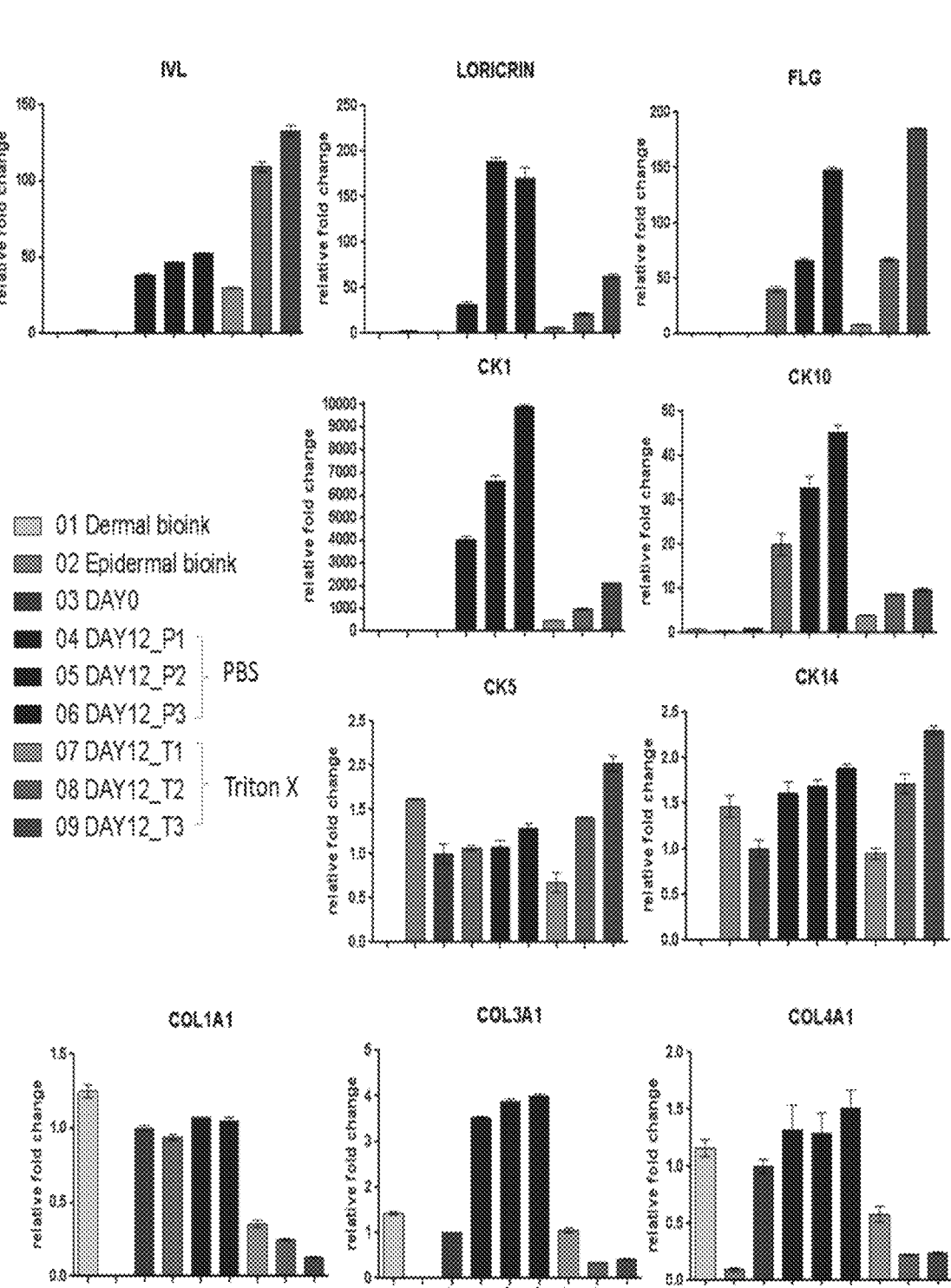

FIG. 23 shows gene expression analysis of dermal markers from bioprinted skin tissue after treatment with 1% Triton X-100™ and PBS for 48 hours.

Figure 24:
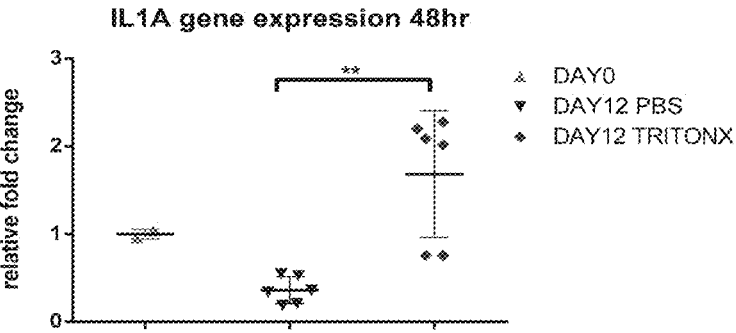

FIG. 24 shows ILIA gene expression from bioprinted skin tissue after 48 hours after treatment with 1% Triton X-100™ or PBS.

FIG. 25 shows LDH activity (A), IL-1α production (B) and alamar bloc assay (C) of bioprinted skin tissues treated with 1% Triton X-100™ or 5% SDS.

FIG. 26 shows non-limiting examples of printing configurations to apply a test substance to printed tissue.

FIG. 27 shows non-limiting examples of printing configurations to apply a therapeutic substance to printed tissue.

Figure 28:
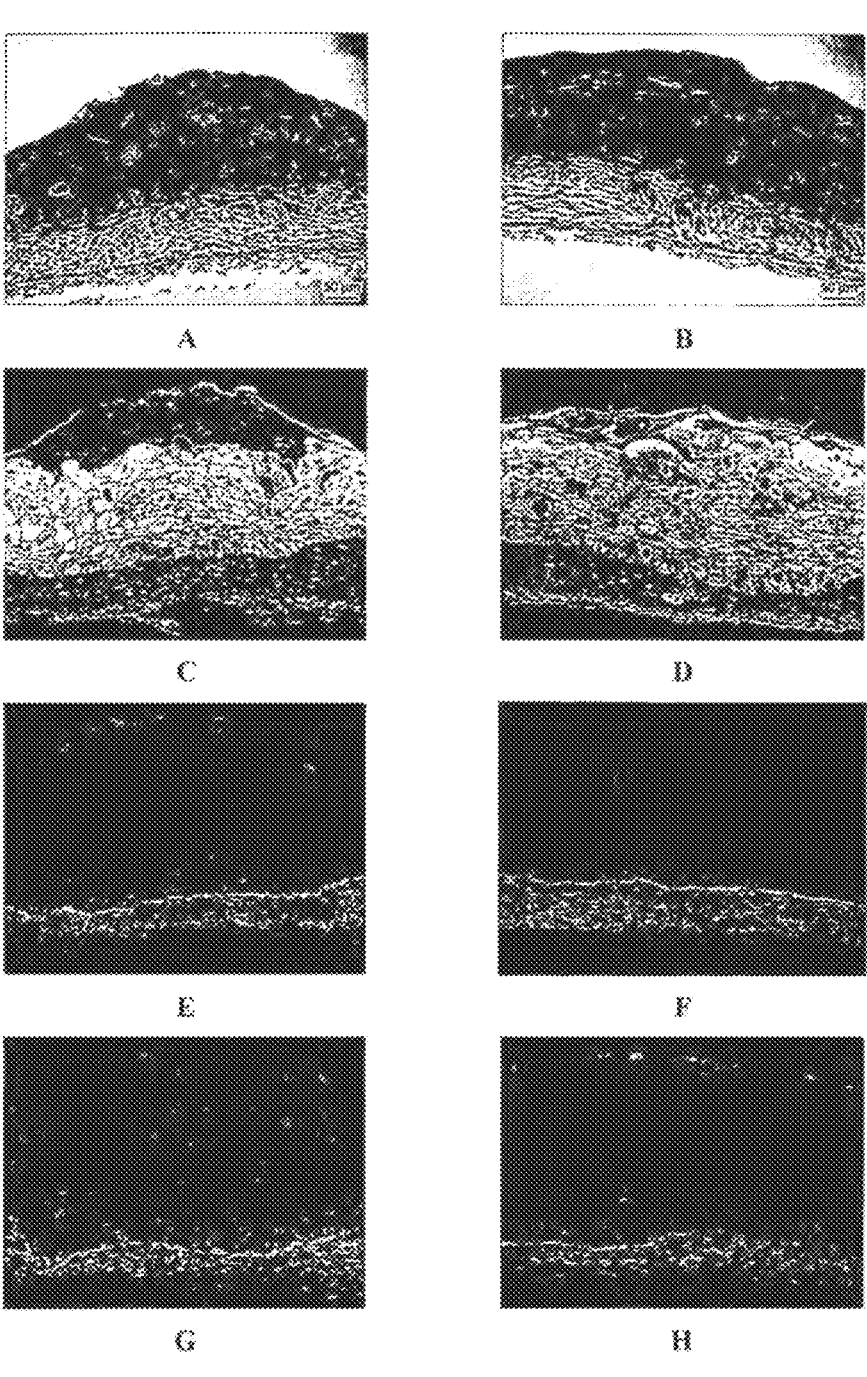

FIG. 28 shows two non-limiting examples of three-dimensional, engineered, biological skin tissues printed in Example 6. Tissue example 1 (A, C, E, G) and Tissue example 2 (B, D, F, H). The tissue were stained for H&E (A and B); B (CK5), (green), and Involucrin (IVL) (red) (C and D); Collagen 4 (COL4) (E and F); and Collagen 7 (COL7) (G and H).

FIG. 29 shows H&E staining of a natural tissue (A), and a non-limiting example of three-dimensional engineered, biological skin tissue (B).

DETAILED DESCRIPTION OF THE INVENTION

Described herein, in certain embodiments, are three-dimensional engineered, biological skin tissues comprising: a dermal layer comprising dermal fibroblasts; and an epidermal layer comprising keratinocytes, the epidermal layer in contact with the dermal layer to form the three-dimensional engineered, biological skin tissue, provided that the dermal layer was bioprinted from a dermal bio-ink, the epidermal layer was bioprinted from an epidermal bio-ink, or both the dermal layer and the epidermal layer were bioprinted from their respective bio-inks.

Also described herein, in certain embodiments, are arrays of three-dimensional, engineered, biological skin tissues, each skin tissue comprising: a dermal layer comprising dermal fibroblasts; and an epidermal layer comprising keratinocytes, the epidermal layer in contact with the dermal layer to form the three-dimensional. engineered, biological skin tissue; provided that the dermal layer, the epidermal layer, or both the dermal layer and the epidermal layer were bioprinted; provided that the array is adapted for use in screening assays.

Also described herein, in certain embodiments, are methods of fabricating a three-dimensional, engineered, biological skin tissue, the method comprising: preparing a dermal bio-ink comprising dermal fibroblasts; preparing an epidermal bio-ink comprising keratinocytes; depositing the dermal bio-ink on a surface: depositing the epidermal bio-ink such that the epidermal bio-ink forms a layer on at least one surface of the dermal bio-ink, and maturing the deposited bio-ink in a cell culture media to allow the tells to cohere to form the three-dimensional, engineered, biological skin tissue.

Also described herein, in certain embodiments, are three-dimensional, engineered, biological multi-tissue systems comprising: a first engineered tissue, the first engineered tissue an engineered skin tissue comprising: a dermal layer comprising dermal fibroblasts; and an epidermal layer comprising keratinocytes, the epidermal layer in contact with the dermal layer to form the engineered skin tissue; wherein at least one component of the skin tissue was bioprinted; and a second engineered tissue, the second engineered tissue not a skin tissue, the second engineered tissue in physical or fluidic contact with the engineered skin tissue to form the multi-tissue system, wherein at least one component of the second tissue was bioprinted.

Also described herein, in certain embodiments, are three-dimensional, engineered, biological skin tissues comprising a dermis, the dermis comprising dermal fibroblasts; provided that the dermis was bioprinted from a dermal bio-ink and fused to form the three-dimensional, engineered, biological skin tissue.

Also described herein, in certain embodiments, are three-dimensional, engineered, biological skin tissues comprising an epidermis, the epidermis comprising keratinocytes; provided that the epidermis was bioprinted from an epidermal bio-ink and fused to form the three-dimensional, engineered, biological skin tissue.

Also described herein, in certain embodiments. are methods of fabricating a three-dimensional, engineered, biological skin tissues, the methods comprising: preparing a dermal bio-ink comprising dermal fibroblasts; preparing an epidermal bio-ink comprising keratinocytes; depositing the dermal bio-ink on a surface; depositing the epidermal bio-ink such that the epidermal bio-ink forms a layer on at least one surface of the dermal bio-ink, wherein the deposition of the epidermal bio-ink occurs greater than 10 milliseconds after deposition of the dermal bio-ink.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein, "tissue" means an aggregate of cells.

As used herein, "array" means a scientific tool including an association of multiple elements spatially arranged to allow a plurality of tests to be performed on a sample, one or mote tests to be performed on a plurality of samples, or both.

As used herein, "assay" means a procedure for testing or measuring the presence or activity of a substance (e.g., a chemical, molecule, biochemical, protein, hormone, or drug, etc.) in an organic or biologic sample (e.g., cell aggregate, tissue, organ, organism, etc.).

As used herein, "compartment" means an association of cells or extracellular matrix components cohered to create a distinct type or sub-type of a tissue such as epidermal, dermal, hypodermal or basal; or a specialized organoid such as a follicle. An organoid is an association of cells that perform a dedicated function (a hair follicle for example ). A compartment can comprise a layered geometry, but also cell conglomerates with any geometric or irregular shape.

As used herein, "layer" means an association of cells or extracellular matrix components in X and Y planes that is multiple cells thick. In some embodiments, the engineered skin tissues describe herein include one layer. In other embodiments, the engineered skin tissues describe herein include a plurality of layers. In various embodiments, a layer forms a contiguous, substantially contiguous, or non-contiguous sheet of cells and/or extracellular matrix components. In some embodiments, each layer of an engineered skin tissue described herein comprises multiple cells in the X, Y, and Z axes. In some embodiments, an engineered skin tissue described herein comprises only of layers of cells. In other embodiments, a layer of extracellular matrix components can be printed between layers of cells.

As used herein, "bio-ink" means a liquid, semi-solid, or solid composition for use in bioprinting. In some embodiments, bio-ink comprises cell solutions, cell aggregates, cell-comprising gels, multicellular bodies, or tissues. In some embodiments, the bio-ink can be a solid or semi-solid. In some embodiments, the bio-ink additionally comprises non-cellular materials that provide specific biomechanical properties that enable bioprinting. In some embodiments, the bio-ink comprises an extrusion compound. In some cases, the extrusion compound is engineered to be removed after the bioprinting process, hi other embodiments, at least some portion of the extrusion compound remains entrained with the cells post-printing and is not removed.

As used herein, "bioprinting" means utilizing three-dimensional, precise deposition of cells (e.g., cell solutions, cell-containing gels, cell suspensions, cell pastes, cell concentrations, multicellular aggregates, multicellular bodies, etc.) via methodology that is compatible with an automated or semi-automated, computer-aided, three-dimensional prototyping device (e.g., a bioprinter) Bioprinting encompasses methods compatible with printing living cells such as extrusion in continuous and/or discontinuous fashion. Extrusion in this context means forcing a semi-solid or solid bio-ink through an orifice, wherein the bio-ink retains its shape to a degree and for a time period after being forced through the orifice. Bioprinting also encompasses aerosol spray methods where cells are applied by ejecting a substantially low viscosity liquid in a mist, spray, or droplets onto a surface. Suitable bioprinters include Novogen Bioprinters® from Organovo, Inc. (San Diego, CA).

As used herein, "scaffold" refers to synthetic scaffolds such as polymer scaffolds and porous hydrogels, non-synthetic scaffolds such as pre-formed extracellular matrix layers, dead cell layers, and decellularized tissues, and any oilier type of pre-formed scaffold that is integral to the physical structure of the engineered tissue and not able to be removed from the tissue without damage/destruction of said tissue. In further embodiments, decellularized tissue scaffolds include decellulariaed native tissues or decellularized cellular material generated by cultured cells in any manner: for example, cell layers that are allowed to die or are decellularized, leaving behind the ECM they produced while living. The term "scaffoldless," therefore, is intended to imply that pre-formed scaffold is not an integral part of the engineered tissue at the time of use, either having been removed or remaining as an inert component of the engineered tissue. "Scaffoldless" is used interchangeably with "scaffold-free" and "free of pre-formed scaffold."

As used herein, "subject" means any individual, which is a human, a non-human animal, any mammal, or any vertebrate. The term is interchangeable with "patient," "recipient" and "donor."

As used herein, "test substance" refers to any biological, chemical or physical substance under evaluation for its ability to elicit a change in said skin tissue compared to skin tissue not treated with said substance. A non-limiting example of a change in skin tissue could be an allergic reaction, a toxic reaction, an irritation reaction; a change that is measured by a defined molecular state such as a change in mRNA levels or activity, changes in protein levels, changes in protein modification or epigenetic changes; or a change that results in a measurable cellular outcome such as a change in proliferation, apoptosis, cell viability, cell division, cell motility, cytoskeletal rearrangements, chromosomal number or composition. Test substances include, but are not limited to; chemical compositions containing an active or inactive ingredient, either in whole, in part, isolated, or purified; physical stressors such as light, UV light, mechanical stress, heat, or cold; biological agents such as bacteria, viruses, parasites, or fungi. "Test substance" also refers to a plurality of substances mixed or applied separately.

As used herein, "therapeutic substance" refers to any composition containing an active ingredient, which can be used to treat a condition in a subject. Examples of active ingredients include but are not limited to antibiotics, antivirals, antifungals, anti-inflammatories, immunosuppressants, analgesics, opiates, vasoconstrictors, vasodilators, steroids, vitamin mixtures or supplement mixtures. "Therapeutic substance" also refers to a plurality of substances mixed or applied separately. A therapeutic substance can also be any substance used to protect skin or promote its attachment and ability to thrive at a site of engraftment. These include but are not limited to skin protectants, moisturizers, adhesives (biodegradable or non-biodegradable), physical barriers (biodegradable o r non-biodegradable), porous membranes, or non-porous membranes.

As used herein, "toxicology" refers to the assessment of any, biological, chemical or physical agent for harm when contacted with a tissue. The dosage amounts of agents for toxicology testing can include dosage ranges that are greater than or less than what would be considered a recommended, physiological or therapeutic dose.

As used herein, "use" encompasses a variety of possible uses of the tissue which will be appreciated by one skilled in the art. These uses include by way of non-limiting example; implantation or engraftment of the engineered tissue into or onto a subject; inclusion of the tissue in a biological assay for the purposes of biological, biotechnological or pharmacological discovery; toxicology testing, including teratogen testing; pharmacology testing, including testing to determine pharmacokinetics and drug metabolism and absorption and skin penetration, cosmetic testing, including testing to determine sensitization, potential to cause irritation or corrosion of any layer of the dermis, to any test chemical or non-chemical agent including ultraviolet light. "Use" can also refer to the process of maturation, or tissue cohesion, in vitro after bioprinting.

As used herein, "substantially free" means less than 2.0%, less than 1.0%, less than 0.1%, only trace amounts, or entirely free of the indicated substance, tissue-type, cell-type, or structure.

Engineered, Three-Dimensional Skin Tissues

Three-dimensional skin tissues disclosed herein represent an improvement to the state of the art. Tissue models for human skin are valuable in both the cosmetic and pharmaceutical industries as an alternative to in vivo models to determine toxic potential, toxic potency, and for hazard identification of chemicals. Skin models have been developed for toxicology assessment as an alternative to in vivo models. These skin models generally follow methods detailed in Organization for Economic Co-operation and Development (OECD) test guidelines (TG) 439 and 431 for reconstructed human epidermis skin irritation and corrosion, respectively. Skin irritation refers to the production of reversible damage to the skin following the application of a test chemical for up to 4 hours [as defined by the United Nations (UN) Globally Harmonized System of Classification and Labelling of Chemicals (GHS)]. Skin corrosion refers to the production of irreversible damage to the skin manifested as visible necrosis through the epidermis and into the dermis, following the application of a test material (UN GHS). Provided herein, are non-limiting examples of usage for engineered 3D skin tissue as an in vitro system to model toxicology. In addition to prediction and classification of test substances as irritating or corrosive, provided herein are in vitro human skin models that are sufficiently complex to mimic morphology, cell reactivity and barrier function of native skin can be used to predict phototoxicity, genotoxicity, sensitization, penetration, absorption, adsorption, and to model transdermal drug delivery.

Fabricating skin with the bioprinting platform disclosed herein compared to current skin models and natural skin is that the process is automated. This allows for greater reproducibility and scalability. For example, it is possible to miniaturize the tissue geometry in order to print bio-ink into well plate formats such as 6, 12, 24, 48, 96, 384 or 1536-well plates for use in screening abdications including high-throughput screening applications. Another major advantage of an automated platform is that it can be utilized to administer substances for toxicity testing in addition to bioprinting tissue. Current testing in skin models is limited by the manual approaches necessary both to fabricate the tissue and to apply a test material to that tissue, limiting the application to topical administration. The flexibility of the printing platform allows for a variety of methods for application, deposition, and incorporation into tissues not possible with a manual approach. For example, test articles could be sprayed in a fine mist using the inkjet technology, or injected into the dermal layer utilizing the continuous deposition module. A third major advantage of bioprinting in a skin toxicology model is the time frame in which a layered structure can be generated and tested. Current 3D skin models often require a minimum of 4 weeks to obtain a layered skin-like structure. Bioprinting approaches can overlay sheets of cells simultaneously or with a delay to create dermal and epidermal layers which can then be allowed to mature and differentiate for a defined period of time. The bioprinting platform allows for longitudinal studies nor possible with manual approaches because test substances can be exposed to or incorporated into tissues during printing or administered to mature tissues at later time points The skin tissue testing method presented in this disclosure allows for application and analysis of a potentially toxic test substance to a tissue exhibiting layered architecture.

In some embodiments, the three-dimensional, engineered, biological skin tissues described herein include one or more compartments or cellular layers. In some embodiments, the engineered skin tissues consist essentially of a dermal layer or dermal compartment. In other embodiments, the engineered skin tissues consist essentially of an epidermal layer or epidermal compartment. In yet other embodiments, the engineered skin tissues are full-thickness skin tissues compared a dermal layer or dermal compartment and an epidermal layer or epidermal compartment. In yet other embodiments, the engineered skin tissues are full-thickness skin tissues consisting essentially of a dermal layer or dermal compartment and an epidermal layer or epidermal compartment. In further embodiments, the epidermal layer or compartment is stratified. In some embodiments, the engineered skin tissues comprise a hypodermal layer or compartment.

In some embodiments, the engineered .skin tissues comprise a basal layer or compartment. In yet another embodiment the skin tissue consists essentially of an epidermal layer, a dermal layer and a hypodermal layer.

In some embodiments, the tissues, arrays, and methods described herein include one or more adherent cell types, or use of the same. Many cell types are suitable for inclusion in the engineered skin tissues. By way of example, in some embodiments, the engineered skin tissues include dermal fibroblasts and keratinocytes. By way of further example, in some embodiments, the engineered skin tissues include melanocytes. By way of further example, in some embodiments, the engineered skin tissues include secretory cells and or immune cells. In a particular embodiment, the engineered skin tissues include cancer cells. In a particular embodiment, the engineered skin tissues include cells derived from induced pluripotent stem (iPS) cells or embryonic stem (ES) cells. In some embodiments, the cells are human cells. In some embodiments, the cells are primary cells. In some embodiments, the cells are primary human cells.

In some embodiments, the cells are bioprinted. In further embodiments, the bioprinted cells are cohered to form the engineered skin tissues. In still further embodiments, the engineered skin tissues are free or substantially free of preformed scaffold at the time of fabrication or the time of use. In some cases, bioprinting allows fabrication of tissues that mimic the appropriate cellularity of native tissue. In some embodiments, the cells are bioprinted by an extrusion method. In some embodiments, the cells are bioprinted by an aerosol spray method.

In some embodiments, the three-dimensional, engineered skin tissues described herein are distinguished from tissues fabricated by prior technologies by virtue of the fact that they are three-dimensional, free of pre-formed scaffolds, consist essentially of cells, and/or have a high cell density (e.g., greater than 30% cellular, greater than 40% cellular, greater than 50% cellular, greater than 60% cellular, greater than 70% cellular, greater than 80% cellular, or greater than 90% cellular).

Distinguished from Native Tissue

In some embodiments, the three-dimensional, engineered skin tissues described herein are distinguished from native (e.g., non-engineered or fabricated) tissues by virtue of the fact that they are non-innervated (e.g., substantially free of nervous tissue), substantially free of mature vasculature, and/or substantially free of blood components. In certain embodiments, the tissues lack perfusable vasculature. For example, in various embodiments, the three-dimensional, engineered skin tissues are free of plasma, red blood cells, platelets, and the like and/or endogenously-generated plasma, red blood cells, platelets, and the like. In certain embodiments, the tissues lack hemoglobin. In some embodiments. the tissues lack innervation or neurons. In some embodiments, the tissue lack cells expressing neuronal markers such as any of: Beta III tubulin, MAP2, NeuN and neuron specific enolase. In certain embodiments, the tissues are free of lymphatics. In certain embodiments, the tissues are free of immune cells. In certain embodiments, the tissues are free of Langerhans cells. In certain embodiments, the tissues are free of T-cells. In certain embodiments. the cells are substantially free of any of the immune cells marked by the following proteins: CD11c, DC-SIGN, CD11b, CD4, CD8, CD28, CD3, CD19, CD80, and/or CD86.

The tissues of the current disclosure are marked by extended viability in culture. Traditional tissue explants exhibit low viability in in vitro culture. In certain embodiments, the three-dimensional, engineered skin tissues described herein are viable after 7 days or more in culture. In certain embodiments, the three-dimensional, engineered skin tissues described herein are viable after 10 days or more in culture. In certain embodiments, the three-dimensional, engineered skin tissues described herein are viable after 14 days or more in culture. In certain embodiments, the three-dimensional, engineered skin tissues described herein are viable after 21 days or more in culture. In certain embodiments, bioprinted tissues possess a higher basal metabolic rate than tissues directly ex vivo. In certain embodiments, bioprinted tissues possess a higher proliferative rate than tissues directly ex vivo or tissues in vivo.

In certain embodiments, greater than 50% of the cells of the three-dimensional, engineered skin tissue are live after 7 days post bioprinting. In certain embodiments, greater than 70% of the cells of the three-dimensional, engineered skin tissue are live after 7 days post bioprinting. In certain embodiments, greater than 90% of the cells of the three-dimensional, engineered skin tissue are live after 7 days post bioprinting. In certain embodiments, greater than 50% of the cells of the three-dimensional, engineered skin tissue are live after 14 days post bioprinting. In certain embodiments, greater than 70% of the cells of the three-dimensional, engineered skin tissue are live after 14 days post bioprinting. In certain embodiments, greater titan 90% of the cells of the three-dimensional, engineered skin tissue are live after 14 days post bioprinting. In certain embodiments, greater than 50% of the cells of the three-dimensional, engineered skin tissue are live after 21 days post bioprinting. In certain embodiments, greater than 70% of the cells of the three-dimensional, engineered skin tissue are live after 21 days post bioprinting. In certain embodiments, greater than 90% of the cells of the three-dimensional, engineered skin tissue are live after 21 days post bioprinting.

One advantage of the tissues fabricated by the methods of this disclosure is the ability to form novel and advantageous chimeras. In some embodiments, the engineered skin tissues are species chimeras, wherein at least one cell or cell-type of the tissue is from a different mammalian species than another cell or cell-type of the tissue. For example, the dermal bio-ink contains a cell of mouse, rat, or primate origin and the epidermal bio-ink contains a cell of human origin. In some embodiments, the engineered skin tissues are genetic chimeras, wherein at least one cell or cell-type is from a different genetic background (e.g., different genotype, etc. ) than the genetic background of any other cell or cell-type of the tissue. For example, the dermal fibroblasts of the dermal bio-ink may be from a certain donor and the keratinocytes or melanocytes of the epidermal bio-ink may be from a different donor, creating a genetic chimera. In some embodiments, the engineered skin tissues are chimeras of other types. For example, the dermal bio-ink may comprise a transformed dermal fibroblast, and the epidermal bio-ink may comprise a primary untransformed keratinocyte or melanocyte. In certain embodiments. the dermal bio-ink may contain fibroblasts of non-dermal origin. In certain embodiments, the hypodermal bio-ink may contain endothelial cells of non-dermal origin.

Figure 1:
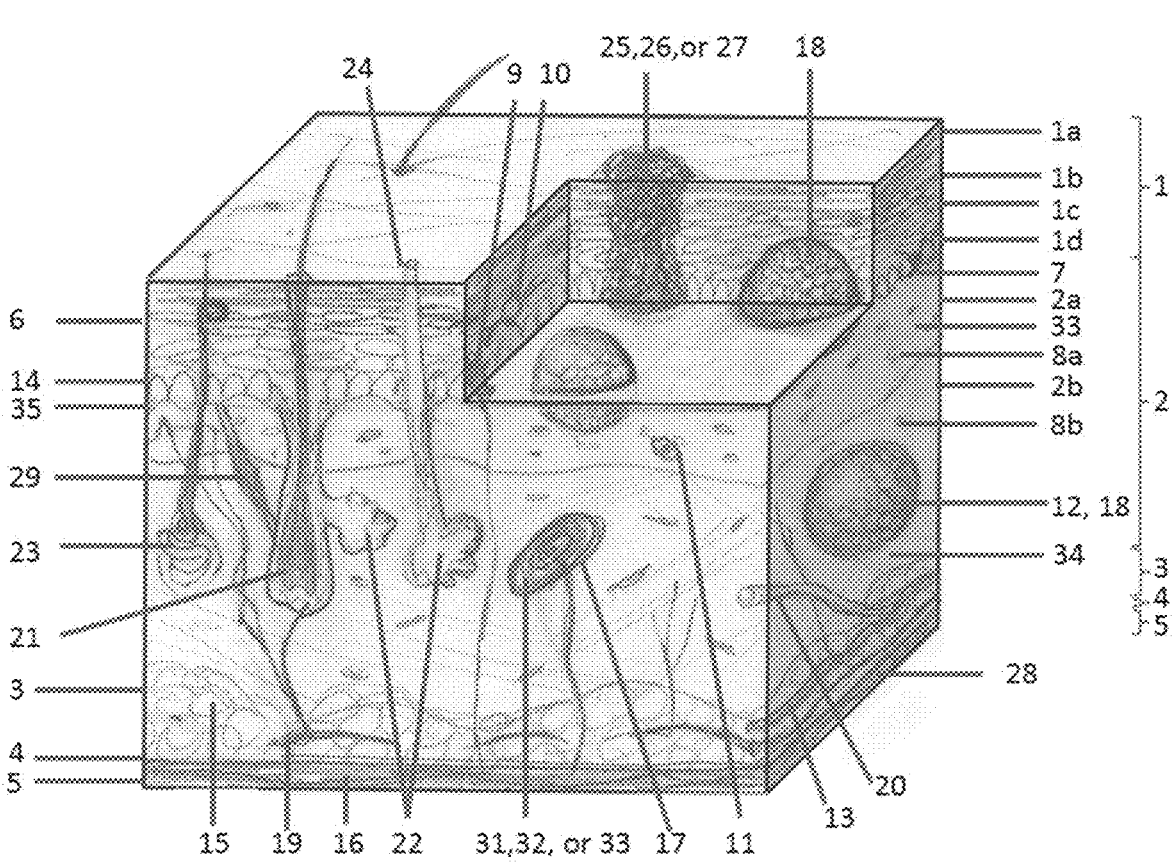
FIG. 1 shows a non-limiting example of a schematic structure diagram depicting optional features of the engineered skin tissues described herein.

FIG. 1 illustrates a cross-section of native skin tissue. As illustrated in FIG. 1 native human skin includes an epidermal layer (keratinocytes) 1 (further comprising a stratum corneum 1a, stratum granulosum 1b, stratum spinosum 1c, and stratum basale 1d), a dermal layer 2 (further comprising a papillary dermal layer 2a and peticular dermal layer 2b), a subcutaneous fatty tissue layer 3, a connective tissue layer 4, and a muscle layer 5.

Further, as illustrated in FIG. 1, native human skin includes keratinocytes 6, melanocytes 7, fibroblasts 8 (including papillary dermal fibroblasts 8a and reticular dermal fibroblasts 8b), Merkel cells 9, Langerhans cells 10, macrophages 11, stem cells 12, endothelial cells 13, epithelial cells 14, adipocytes 15, muscle cells 16, and sensory neurons 17.

Further, as illustrated in FIG. 1, native human skin includes organoids 18, blood vessels 19, lymphatic vessels 20, hair follicles 21, sebaceous glands 22, sweat glands 23, pores 24. muscle 28, arrector pili muscle 29, Meissner's corpuscle 30, Pacinian corpuscle 31, Ruffini corpuscle 32, loose connective tissue 33, dense connective tissue 34, and basement membrane 35.

Further, as illustrated in FIG. 1, native human skin, in some cases, includes basal cell carcinoma 25, squamous cell carcinoma 26, and melanoma 27.

In some embodiments, one or more components of the engineered skin tissue described herein are bioprinted, which comprises an additive fabrication process. Therefore, in such embodiments, through the methods of fabrication, the fabricator exerts significant control over the composition of the resulting engineered skin tissues described herein. As such, the engineered skin tissues described herein optionally comprise any of the layers, structures, compartments, and or cells of native tissue. Conversely, the engineered skin tissues described herein optionally lack any of the layers, structures, compartments, and or cells of native tissue.

Referring to FIG. 1, in some embodiments, an engineered skin tissue described herein does not comprise (e.g., lacks) layers or compartments selected from any of the following: a stratum corneum 1a, stratum granulosum 1b, stratum spinosum 1c, and stratum basale 1d; a papillary dermal layer 2a and peticular dermal layer 2b, a subcutancous fatty tissue layer 3, a connective tissue layer 4, and a muscle layer 5. Further, in certain embodiments, an engineered skin tissue described herein does not comprise cells selected from: keratinocytes 6, melanocytes 7, fibroblasts 8 (including papillary dermal fibroblasts 8a and reticular dermal fibroblasts 8b), Merkel cells 9, Langerhans cells 10, macrophages 11, stem cells 12, endothelial cells 13, epithelial cells 14, adipocytes 15, muscle cells 16, and sensory neurons 17. Further, in certain embodiments, an engineered skin tissue described herein does not comprise structures selected from: organoids 18, blood vessels 19, lymphatic vessels 20, hair follicles 21, sebaceous glands 22, sweat glands 23, pores 24. basal cell carcinoma 25, squamous cell carcinoma 26, melanoma 27, muscle 28, arrector pili muscle 29, Meissner's corpuscle 30, Pacinian corpuscle 31, Ruffini corpuscle 32, loose connective tissue 33, dense connective tissue 34, and basement membrane 35.

Figure 2:
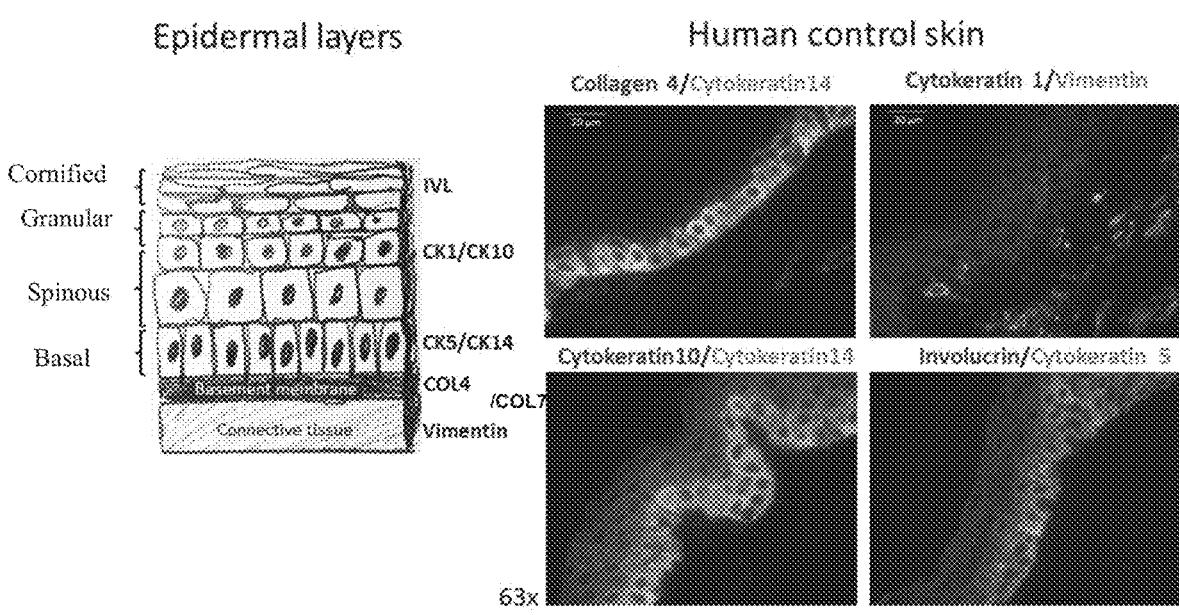
FIG. 2 shows a non-limiting example of a diagram illustrating the stratified epidermal layers seen in normal skin tissues and exemplary biomarkers suitable to visualize specific layers.

Referring to FIG. 2, normal human skin tissue includes an epidermal layer stratified into basal, spinous, granular, and cornified layers, atop a basement membrane, which in turn rests upon a layer of connective tissue. A variety of biomarkers are optionally utilized to visualize these layers.

Bio-Ink

The tissues, arrays, and methods described herein involve bio-ink formulations and bioprinting methods to create 3D skin tissue structures. In certain embodiments, the bio-ink is dermal, epidermal, hypodermal, basal non-cellular bio-ink, or arty combination thereof.

The tissues, arrays, and methods described herein involve bio-ink formulations and bioprinting methods to create 3D skin tissue structures containing compositions of keratinocytes. fibroblasts, and/or melanocytes or endothelial cells. The printing methods utilize bio-ink to create geometries which produce layers or compartments to mimic native skin. Bioprinted tissues optionally model the dermis, epidermis, or a combination of both. In various embodiments the bio-ink contains a cellular mixture of some proportion of keratinocytes, fibroblasts, and/or melanocytes and optionally contains a biomaterial support. In other embodiments, the bio-ink contains some portion of keratinocytes, melanocytes, fibroblasts (including papillary dermal fibroblasts and reticular dermal fibroblasts), Merkel cells, Langerhans cells, macrophages, stem cells, endothelial cells, epithelial cells, adipocytes, muscle cells, and sensory neuronal cells and optionally contains a biomaterial support. In various embodiments, the printing methods utilize a variety of printing surfaces with a variety of pore sizes that are optionally coated with matrix support material such as collagen. In some embodiments, hydrogels are optionally added to support biomaterials or constitute space-saving regions in which there are no cells. In various embodiments, the skin tissue comprises epidermal bio-inks, dermal bio-inks or both. In certain embodiments, bio-inks consist essentially of a certain cell type.

Consisting essentially means that the specified coll type is the only cell type present, but the bio-ink may contain other non-cellular material including but not limited to extrusion compounds, hydrogels, extracellular matrix components, nutritive and media components, inorganic and organic salts, acids and bases, buffer compounds and other non-cellular components that promote cell survival, adhesion, growth, or facilitate printing.

In some embodiments, the bio-ink further comprises an extrusion compound (i.e., a compound that modifies the extrusion properties of the bio-ink). Examples of extrusion compounds include, but are not limited to gels, hydrogels, peptide hydrogels, amino acid-based gels, surfactant polyols (e.g., Pluronic F-127 or PF-127), thermo-responsive polymers, hyaluronates, alginates, extracellular matrix components (and derivatives thereof), collagens, gelatin, other biocompatible natural or synthetic polymers, nanofibers, and self-assembling nanofibers. In some embodiments, extrusion compounds are removed after bioprinting by physical, chemical, or enzymatic means.

Suitable hydrogels include those derived from collagen, hyaluronate, hyaluronan, fibrin, alginate, agarose, chitosan, chitin, cellulose, pectin, starch, polysaccharides, fibrinogen/thrombin, fibrillin, elastin, gum, cellulose, agar, gluten, casein, albumin, vitronectin, tenascin, entactin/nidogen, glycoproteins, glycosaminoglycans (GAGs) and proteoglycans which may contain for example chrondroitin sulfate, fibronectin. keratin sulfate, laminin, heparan sulfate proteoglycan, decorin, aggrecan, perlecan or any combination thereof. In other embodiments, suitable hydrogels are synthetic polymers. In further embodiments, suitable hydrogels include those derived from poly(acrylic acid) and derivatives thereof, polyethylene oxide) and copolymers thereof, poly(vinyl alcohol), polyphosphazcne, and combinations thereof. In various specific embodiments, the confinement material is selected from: hydrogel, NovoGel™, agarose, alginate, gelatin, Matrigel™, hyaluronan, poloxamer, peptide hydrogel, poly(isopropyl n-polyacrylamide), polyethylene glycol diacrylate (PEG-DA), hydroxyethyl methacrylate, polydimethylsiloxane, polyacrylamide, poly(lactic acid), silicon, silk, or combinations thereof.

In certain embodiments, the bio-ink is a viscous liquid. In certain embodiments, the bio-ink is a semi-solid. In certain embodiments, the bio-ink is a solid. In certain embodiments, the bio-ink is a semi-solid or a solid. In certain embodiments, the viscosity of the bio-ink is greater than 100 centipoise. In certain embodiments, the viscosity of the bio-ink is greater than 200 centipoise. In certain embodiments, the viscosity of the bio-ink is greater than 500 centipoise. In certain embodiments, the viscosity of the bio-ink is greater than 1,000 centipoise. In certain embodiments, the viscosity of the bio-ink is greater than 2,000 centipoise. In certain embodiments, the viscosity of the bio-ink is greater than 5,000 centipoise. In certain embodiments, the viscosity of the bio-ink is greater than 10,000 centipoise. In certain embodiments, the viscosity of the bio-ink is greater than 20,000 centipoise. In certain embodiments, the viscosity of the bio-ink is greater than 50,000 centipoise. In certain embodiments, the viscosity of the bio-ink is greater than 100,000 centipoise. In certain embodiments, the viscosity of the bio-ink is less than 100 centipoise. In certain embodiments, the viscosity of the bio-ink is less than 200 centipoise. In certain embodiments, the viscosity of the bio-ink is less than 500 centipoise. In certain embodiments, the viscosity of the bio-ink is less than 1,000 centipoise. In certain embodiments, the viscosity of the bio-ink is less than 2,000 centipoise. In certain embodiments, the viscosity of the bio-ink is less than 5,000 centipoise. In certain embodiments, the viscosity of the bio-ink is less than 10,000 centipoise. In certain embodiments, the viscosity of the bio-ink is less than 20,000 centipoise. In certain embodiments, the viscosity of the bio-ink is less than 50,000 centipoise. In certain embodiments, the viscosity of the bio-ink is leas than 100,000 centipoise.

Dermal Bio-Ink

In some embodiments, the three-dimensional, engineered skin tissues comprise a dermal bio-ink. In certain embodiments, the dermal bio-ink comprises fibroblasts, in certain embodiments, the dermal bio-ink comprises dermal fibroblasts. In certain embodiments, the dermal bio-ink comprises human dermal fibroblasts. In certain embodiments, the dermal bio-ink comprises primary human dermal fibroblasts. In certain embodiments, the dermal bio-ink comprises non-dermal fibroblasts. In certain embodiments, the dermal bio-ink consists essentially of fibroblasts. In certain embodiments, the dermal bio-ink consists essentially of dermal fibroblasts. In certain embodiments, the dermal bio-ink consists essentially of human dermal fibroblasts. In certain embodiments, the dermal bio-ink consists essentially of primary human dermal fibroblasts. In certain embodiments, the dermal bio-ink consists essentially of non-dermal fibroblasts.

In certain embodiments, the dermal bio-ink comprises greater than 50% live cells by volume. In certain embodiments, the dermal bio-ink comprises greater than 60% live cells by volume. In certain embodiments, the dermal bio-ink comprises greater than 70% live cells by volume. In certain embodiments, the dermal bio-ink comprises greater than 80% live cells by volume. In certain embodiments, the dermal bio-ink comprises greater than 90% live cells by volume. In certain embodiments, the dermal bio-ink comprises greater than 95% live cells by volume.

In certain embodiments, the dermal bio-ink can be applied as a layer or an individual compartment by an aerosol spray method. In certain embodiments, the dermal bio-ink comprises between 0.05 million and 50 million cells per milliliter. In certain embodiments, the dermal bio-ink comprises between 0.1 million and 50 million cells per milliliter. In certain embodiments, the dermal bio-ink comprises between 0.1 million and 40 million cells per milliliter. In certain embodiments, the dermal bio-ink comprises between 0.1 million and 30 million cells per milliliter. In certain embodiments, the dermal bio-ink comprises between 0.5 million and 50 million cells per milliliter. In certain embodiments, the dermal bio-ink comprises between 0.5 million and 40 million cells per milliliter. In certain embodiments, the dermal bio-ink comprises between 0.5 million and 30 million cells per milliliter. In certain embodiments, the dermal bio-ink comprises between 1 million and 50 million cells per milliliter. In certain embodiments, the dermal bio-ink comprises between 1 million and 40 million cells per milliliter. In certain embodiments, the dermal bio-ink comprises between 1 million and 30 million cells per milliliter. In certain embodiments, the dermal bio-ink comprises between 10 million and 50 million cells per milliliter. In certain embodiments, the dermal bio-ink comprises between 10 million and 40 million cells per milliliter. In certain embodiments, the dermal bio-ink comprises between 10 million and 30 million cells per milliliter. In certain embodiments, the dermal bio-ink comprises between 2 million and 50 million cells per milliliter. In certain embodiments, the dermal bio-ink comprises between 3 million and 50 million cells per milliliter. In certain embodiments, the dermal bio-ink comprises between 4 million and 50 million cells per milliliter. In certain embodiments, the dermal bio-ink comprises between 5 million and 50 million cells per milliliter. In certain embodiments, the dermal bio-ink comprises less than 50 million cells per milliliter. In certain embodiments, the dermal bio-ink comprises less than 40 million cells per milliliter. In certain embodiments, the dermal bio-ink comprises less than 30 million cells per milliliter. In certain embodiments, the dermal bio-ink comprises less than 25 million cells per milliliter. In certain embodiments, the dermal bio-ink comprises less than 10 million cells per milliliter.

In certain embodiments, the dermal bio-ink can be applied as a layer or an individual compartment by an extrusion method. In certain embodiments, the dermal bio-ink comprises between 5.0 million and 500 million cells per milliliter. In certain embodiments, the dermal bio-ink comprises between 5.0 million and 400 million cells per milliliter. In certain embodiments, the dermal bio-ink comprises between 5.0 million and 300 million cells per milliliter. In certain embodiments, the dermal bio-ink comprises between 10 million and 500 million cells per milliliter. In certain embodiments, the dermal bio-ink comprises between 10 million and 400 million cells per milliliter. In certain embodiments, the dermal bio-ink comprises between 10 million and 300 million cells per milliliter. In certain embodiments, the dermal bio-ink comprises between 10 million and 200 million cells per milliliter. In certain embodiments, the dermal bio-ink comprises between 10 million and 100 million cells per milliliter. In certain embodiments, the dermal bio-ink comprises between 10 million and 50 million cells per milliliter. In certain embodiments, the dermal bio-ink comprises between 100 million and 500 million cells per milliliter. In certain embodiments, the dermal bio-ink comprises between 100 million and 400 million cells per milliliter. In certain embodiments, the dermal bio-ink comprises between 100 million and 300 million cells per milliliter. In certain embodiments, the dermal bio-ink comprises between 100 million and 200 million cells per milliliter. In certain embodiments, the dermal bio-ink comprises between 25 million and 200 million cells per milliliter. In certain embodiments, the dermal bio-ink comprises greater than 50 million cells per milliliter. In certain embodiments, the dermal bio-ink comprises greater than 100 million cells per milliliter. In certain embodiments, the dermal bio-ink comprises greater than 200 million cells per milliliter.

Epidermal Bio-Ink

In some embodiments, the three-dimensional engineered skin tissues comprise an epidermal bio-ink. In certain embodiments, the epidermal bio-ink comprises keratinocytes. In certain embodiments, the epidermal bio-ink comprises melanocytes. In certain embodiments, the epidermal bio-ink comprises keratinocytes and melanocytes. In certain embodiments, the epidermal bio-ink comprises primary keratinocytes. In certain embodiments, the epidermal bio-ink comprises primary melanocytes. In certain embodiments, the epidermal bio-ink comprises primary keratinocytes and primary melanocytes. In some embodiments, the three-dimensional, engineered skin tissue consists essentially of an epidermal bio-ink. In certain embodiments, the epidermal bio-ink consists essentially of keratinocytes. In certain embodiments, the epidermal bio-ink consists essentially of melanocytes. In certain embodiments, the epidermal bio-ink consists essentially of keratinocytes and melanocytes. In certain embodiments. the epidermal bio-ink consists essentially of primary keratinocytes. In certain embodiments, the epidermal bio-ink consists essentially of primary melanocytes. In certain embodiments, the epidermal bio-ink comprises consists essentially of keratinocytes and primary melanocytes. In certain embodiments, the epidermal bio-ink comprises human keratinocytes. In certain embodiments, the epidermal bio-ink comprises human melanocytes. In certain embodiments, the epidermal bio-ink comprises human keratinocytes and human melanocytes In certain embodiments, the epidermal bio-ink comprises human primary keratinocytes. In certain embodiments, the epidermal bio-ink comprises human primary melanocytes. In certain embodiments, the epidermal bio-ink comprises human primary keratinocytes and human primary melanocytes. In certain embodiments, the epidermal bio-ink consists essentially of human keratinocytes. In certain embodiments, the epidermal bio-ink consists essentially of human melanocytes. In certain embodiments. the epidermal bio-ink consists essentially of human keratinocytes and human melanocytes. In certain embodiments, the epidermal bio-ink consists essentially of human primary keratinocytes. In certain embodiments, the epidermal bio-ink consists essentially of human primary melanocytes. In certain embodiments, the epidermal bio-ink comprises consists essentially of human keratinocytes and human primary melanocytes.

In certain embodiments, the epidermal bio-ink comprises, consists essentially of, or consists of keratinocytes and melanocytes, primary or non-primary, at specified ratios. In certain embodiments, the ratio of keratinocytes to melanocytes is from about 75:25 to about 99:1. In certain embodiments, the ratio of keratinocytes to melanocytes is from about 80:20 to about 99:1. In certain embodiments, the ratio of keratinocytes to melanocytes is from about 85:15 to about 99:1. In certain embodiments, the ratio of keratinocytes to melanocytes is from about 88:12 to about 99:1. In certain embodiments, the ratio of keratinocytes to melanocytes is from about 89:11 to about 99:1. In certain embodiments, the ratio of keratinocytes to melanocytes is from about 90:10 to about 99:1. In certain embodiments, the ratio of keratinocytes to melanocytes is from about 91:9 to about 99:1. In certain embodiments, the ratio of keratinocytes to melanocytes is from about 94:6 to about 99:1. In certain embodiments, the ratio of keratinocytes to melanocytes is from about 95:5 to about 99:1. In certain embodiments, the ratio of keratinocytes to melanocytes is from about 96:4 to about 99:1.

In certain embodiments, the epidermal bio-ink comprises greater than 50% live cells by volume. In certain embodiments, the epidermal bio-ink comprises greater than 60% live cells by volume. In certain embodiments, the epidermal bio-ink comprises greater than 70% live cells by volume. In certain embodiments, the epidermal bio-ink comprises greater than 80% live cells by volume. In certain embodiments, the epidermal bio-ink comprises greater than 90% live cells by volume. In certain embodiments, the epidermal bio-ink comprises greater than 95% live cells by volume.

In certain embodiments, the epidermal bio-ink can be applied as a layer or an individual com part mom by an aerosol spray method. In certain embodiments, the epidermal bio-ink comprises between 0.05 million and 50 million cells per milliliter. In certain embodiments, the epidermal bio-ink comprises between 0.1 million and 50 million cells per milliliter. In certain embodiments, the epidermal bio-ink comprises between 0.1 million and 40 million cells per milliliter. In certain embodiments, the epidermal bio-ink comprises between 0.1 million, and 30 million cells per milliliter. In certain embodiments, the epidermal bio-ink comprises between 0.5 million and 50 million cells per milliliter. In certain embodiments, the epidermal bio-ink comprises between 0.5 million and 40 million cells per milliliter. In certain embodiments, the epidermal bio-ink comprises between 0.5 million and 30 million cells per milliliter. In certain embodiments, the epidermal bio-ink comprises between 1 million and 50 million cells per milliliter. In certain embodiments, the epidermal bio-ink comprises between 1 million and 40 million cells per milliliter. In certain embodiments, the epidermal bio-ink comprises between 1 million and 30 million cells per milliliter. In certain embodiments, the epidermal bio-ink comprises between 10 million and 50 million cells per milliliter. In certain embodiments, the epidermal bio-ink comprises between 10 million and 40 million cells per milliliter. In certain embodiments, the epidermal bio-ink comprises between 10 million and 30 million cells per milliliter. In certain embodiments, the epidermal bio-ink comprises between 2 million and 50 million cells per milliliter. In certain embodiments. the epidermal bio-ink comprises between 3 million and 50 million cells per milliliter. In certain embodiments, the epidermal bio-ink comprises between 4 million and 50 million cells per milliliter. In certain embodiments, the epidermal bio-ink comprises between 5 million and 50 million cells per milliliter. In certain embodiments, the epidermal bio-ink comprises less than 50 million cells per milliliter. In certain embodiments, the epidermal bio-ink comprises less than 40 million cells per milliliter. In certain embodiments, the epidermal bio-ink comprises less than 30 million cells per milliliter. In certain embodiments, the epidermal bio-ink comprises less than 25 million cells per milliliter. In certain embodiments, the epidermal bio-ink comprises less than 10 million cells per milliliter.

In certain embodiments, the epidermal bio-ink can be applied as a layer or an individual compartment by an extrusion method. In certain embodiments, the epidermal bio-ink comprises between 5.0 million and 500 million cells per milliliter. In certain embodiments, the epidermal bio-ink comprises between 5.0 million and 400 million cells per milliliter. In certain embodiments, the epidermal bio-ink comprises between 5.0 million and 300 million cells per milliliter. In certain embodiments, the epidermal bio-ink comprises between 10 million and 500 million cells per milliliter. In certain embodiments, the epidermal bio-ink comprises between 10 million and 400 million cells per milliliter. In certain embodiments, the epidermal bio-ink comprises between 10 million and 300 million cells per milliliter. In certain embodiments, the epidermal bio-ink comprises between 10 million and 200 million cells per milliliter. In certain embodiments, the epidermal bio-ink comprises between 10 million and 100 million cells per milliliter. In certain embodiments, the epidermal bio-ink comprises between 10 million and 50 million cells per milliliter. In certain embodiments, the epidermal bio-ink comprises between 100 million and 500 million cells per milliliter. In certain embodiments, the epidermal bio-ink comprises between 100 million and 400 million cells per milliliter. In certain embodiments, the epidermal bio-ink comprises between 100 million and 300 million cells per milliliter. In certain embodiments, the epidermal bio-ink comprises between 100 million and 200 million cells per milliliter. In certain embodiments, the epidermal bio-ink comprises between 25 million and 200 million cells per milliliter. In certain embodiments, the epidermal bio-ink comprises greater than 50 million cells per milliliter. In certain embodiments, the epidermal bio-ink comprises greater than 100 million cells per milliliter. In certain embodiments, the epidermal bio-ink comprises greater than 200 million cells per milliliter.

Hypodermal Bio-Ink

In certain embodiments, the hypodermal bio-ink comprises endothelial cells. In certain embodiments, the hypodermal bio-ink comprises fibroblasts. In certain embodiments, the hypodermal bio-ink comprises endothelial cells and fibroblasts. In certain embodiments, the hypodermal bio-ink comprises human endothelial cells. In certain embodiments, the hypodermal bio-ink comprises human fibroblasts. In certain embodiments, the hypodermal bio-ink comprises human endothelial cells and human fibroblasts. In certain embodiments, the hypodermal bio-ink comprises human primary endothelial cells. In certain embodiments, the hypodermal bio-ink comprises human primary fibroblasts. In certain embodiments, the hypodermal bio-ink comprises human primary endothelial cells and human primary fibroblasts. In certain embodiments, the hypodermal bio-ink consists essentially of endothelial cells. In certain embodiments, the hypodermal bio-ink consists essentially of fibroblasts. In certain embodiments, the hypodermal bio-ink consists essentially of endothelial cells and fibroblasts. In certain embodiments, the hypodermal bio-ink consists essentially of human endothelial cells. In certain embodiments, the hypodermal bio-ink consists essentially of human fibroblasts. In certain embodiments, the hypodermal bio-ink consists essentially of human endothelial cells and human fibroblasts. In certain embodiments, the hypodermal bio-ink consists essentially of human primary endothelial cells. In certain embodiments, the hypodermal bio-ink consists essentially of human primary fibroblasts. In certain embodiments, the hypodermal bio-ink consists essentially of human primary endothelial cells and human primary fibroblasts.

In certain embodiments, the hypodermal bio-ink comprises greater than 50% live cells by volume. In certain embodiments, the hypodermal bio-ink comprises greater than 60% live cells by volume. In certain embodiments, the hypodermal bio-ink comprises greater than 70% live cells by volume. In certain embodiments, the hypodermal bio-ink comprises greater than 80% live cells by volume. In certain embodiments, the hypodermal bio-ink comprises greater than live cells by volume. In certain embodiments, the hypodermal bio-ink comprises greater than 95% live cells by volume.

In certain embodiments, the hypodermal bio-ink can be applied as a layer or an individual compartment by an aerosol spray method. In certain embodiments, the hypodermal bio-ink comprises between 0.05 million and 50 million cells per milliliter. In certain embodiments, the hypodermal bio-ink comprises between 0.1 million and 50 million cells per milliliter. In certain embodiments, the hypodermal bio-ink comprises between 0.1 million and 40 million cells per milliliter. In certain embodiments, the hypodermal bio-ink comprises between 0.1 million and 30 million cells per milliliter. In certain embodiments, the hypodermal bio-ink comprises between 0.5 million and 50 million cells per milliliter. In certain embodiments, the hypodermal bio-ink comprises between 0.5 million and 40 million cells per milliliter. In certain embodiments, the hypodermal bio-ink comprises between 0.5 million and 30 million cells per milliliter. In certain embodiments, the hypodermal bio-ink comprises between 1 million and 50 million cells per milliliter. In certain embodiments, the hypodermal bio-ink comprises between 1 million and 40 million cells per milliliter. In certain embodiments, the hypodermal bio-ink comprises between 1 million and 30 million cells per milliliter. In certain embodiments, the hypodermal bio-ink comprises between 10 million and 50 million cells per milliliter. In certain embodiments, the hypodermal bio-ink comprises between 10 million and 40 million cells per milliliter. In certain embodiments, the hypodermal bio-ink comprises between 10 million and 30 million cells per milliliter. In certain embodiments, the hypodermal bio -ink comprises between 2 million and 50 million cells per milliliter. In certain embodiments, the hypodermal bio-ink comprises between 3 million and 50 million cells per milliliter. In certain embodiments, the hypodermal bio-ink comprises between 4 million and 50 million cells per milliliter. In certain embodiments, the hypodermal bio-ink comprises between 5 million and 50 million cells per milliliter. In certain embodiments, the hypodermal bio-ink comprises less than 50 million cells per milliliter. In certain embodiments, the hypodermal bio-ink comprises less than 40 million cells per milliliter. In certain embodiments, the hypodermal bio-ink comprises less than 30 million cells per milliliter. In certain embodiments, the hypodermal bio-ink comprises less than 25 million cells per milliliter. In certain embodiments, the hypodermal bio-ink comprises less than 10 million cells per milliliter.

In certain embodiments, the hypodermal bio-ink can be applied as a layer or an individual compartment by an extrusion method. In certain embodiments, the hypodermal bio-ink comprises between 5.0 million and 500 million cells per milliliter. In certain embodiments, the hypodermal bio-ink comprises between 5.0 million and 400 million cells per milliliter. In certain embodiments, the hypodermal bio-ink comprises between 5.0 million and 300 million cells per milliliter. In certain embodiments, the hypodermal bio-ink comprises between 10 million and 500 million cells per milliliter. In certain embodiments, the hypodermal bio-ink comprises between 10 million and 400 million cells per milliliter. In certain embodiments, the hypodermal bio-ink comprises between 10 million and 300 million cells per milliliter. In certain embodiments, the hypodermal bio-ink, comprises between 10 million and 200 million cells per milliliter. In certain embodiments, the hypodermal bio-ink comprises between 10 million and 100 million cells per milliliter. In certain embodiments, the hypodermal bio-ink comprises between 10 million and 50 million cells per milliliter. In certain embodiments, the hypodermal bio-ink comprises between 100 million and 500 million cells per milliliter. In certain embodiments, the hypodermal bio-ink comprises between 100 million and 400 million cells per milliliter. In certain embodiments, the hypodermal bio-ink comprises between 100 million and 300 million cells per milliliter. In certain embodiments, the hypodermal bio-ink comprises between 100 million and 200 million cells per milliliter. In certain embodiments, the hypodermal bio-ink comprises between 25 million and 200 million cells per milliliter. In certain embodiments, the hypodermal bio-ink comprises greater than 50 million cells per milliliter. In certain embodiments, the hypodermal bio-ink comprises greater than 100 million cells per milliliter. In certain embodiments, the hypodermal bio-ink comprises greater than 200 million cells per milliliter.

Non-Cellular Bio-Inks

In some embodiments, the three-dimensional, engineered skin tissues comprise a non-cellular bio-ink. In some embodiments, the non-cellular bio-ink comprises extracellular matrix proteins or peptides such as collagen or fibrinogen, hyaluronate, hyaluronan, fibrin, alginate, agarose, chitosan, chitin, cellulose, pectin, starch, polysaccharides, fibrinogen/thrombin, fibrillin, elastin, gum, cellulose, agar, gluten, casein, albumin, vitronectin, tenascin, entactin nidogen, glycoproteins, glycosaminoglycans (GAGs) and proteoglycans which may contain tor example chrondroitin sulfate, fibronectin, keratin sulfate, laminin, heparan sulfate proteoglycan, decorin, aggrecan, perlecan or any combinations thereof. In other embodiments, suitable hydrogels are synthetic polymers. In further embodiments, suitable hydrogels include those derived from poly(acrylic acid) and derivatives thereof, polyethylene oxide) and copolymers thereof, poly(vinyl alcohol), polyphosphazene, and combinations thereof. In various specific embodiments, the confinement material is selected from: hydrogel, NovoGel™, agarose, alginate, gelatin, Matrigel™, hyaluronan, poloxamer, peptide hydrogel, poly(isopropyl n-polyacrylamide), polyethylene glycol diacrylate (PEG-DA), hydroxyethyl methacrylate, polydimethylsiloxane, polyacrylamide, poly (lactic acid), silicon, silk, or combinations thereof. In some embodiments, the non-cellular bio-ink comprises hydrogels or other support materials, cushion materials or confinement materials. In some embodiments, the non-cellular bio-ink does not comprise inorganic or synthetic polymer. In some embodiments, the non-cellular bio-ink does not comprise dead-cell debris.

In some embodiments, the engineered tissues, arrays, and methods described herein incorporate continuous deposition printing into a 3D skin model. Continuous deposition is optionally utilized to produce single or multiple layers mimicking the dermis and/or epidermis. In one embodiment, a bio-ink comprised of fibroblasts is printed to produce a tissue mimicking the dermis. In another embodiment bio-ink comprised of keratinocytes or a mixture of keratinocytes and melanocytes is printed to produce a tissue lo mimic the epidermis. A third embodiment combines bio-inks to simultaneously deposit the epidermal bio-ink on top of the dermal bio-ink. Continuous deposition printing provides an advantage to current 3D skin models in that it enables cells to be placed within a precise geometry and enables the use of multiple bio-ink formulations including, but not limited to, Novogel® 2.0, Novogel® 3.0, and cell paste. Continuous deposition allows optional incorporation of various biomaterials into the Novogel® formulation and various printing surfaces to promote extracellular matrix production and differentiation.

Tissue Architectures

The three-dimensional, engineered skin tissues, arrays, and methods described herein, allow for the generation of multi layered, compartmentalized engineered constructs. The layers are formed by bio-inks disposed upon a surface.

The bio-inks then cohere to form a single tissue with a plurality of layers and-or discrete compartments. In certain embodiments, the tissue layers or compartments are architecturally distinct. In certain embodiments, the skin tissues comprise an epidermal layer. In certain embodiments, the skin tissues comprise a dermal layer. In certain embodiments, the skin tissues comprise a hypodermal layer. In certain embodiments, the skin tissues comprise an epidermal layer disposed on top of a dermal layer. In certain embodiments, the skin tissues comprise an epidermal layer disposed on top of a dermal layer, disposed on top of a hypodermal layer. In certain embodiments, the skin tissues comprise an epidermal layer disposed on top of non-cellular layer, disposed on top of a dermal layer. In certain embodiments, the skin tissues comprise an epidermal layer disposed on top of a non-cellular layer disposed on top of a dermal layer, deposed on top of a hypodermal layer. In certain embodiments, the tissue layers are architecturally distinct. In certain embodiments, the skin tissues consist of an epidermal layer. In certain embodiments, the skin tissues consist of a dermal layer. In certain embodiments, the skin tissues consist of a hypodermal layer, in certain embodiments, the skin tissues consist of an epidermal layer disposed on top of a dermal layer. In certain embodiments, the skin tissues consist of art epidermal layer disposed on top of a dermal layer, disposed on top of a hypodermal layer. In certain embodiments, the skin tissues consist of an epidermal layer disposed on top of non-cellular layer, disposed on top of a dermal layer. In certain embodiments, the skin tissues consist of an epidermal layer disposed on top of a non-cellular layer disposed on top of a dermal layer, deposed on top of a hypodermal layer.

The three-dimensional, engineered skin tissues, arrays, and methods described herein, allow for the generation of multi layered, compartmentalized engineered constructs. In certain embodiments, a compartment is a discrete structure embedded within the tissue or layer of the tissue that extends in the x, y and z plane. In certain embodiments, a single compartment is embedded within a single of layer. In certain embodiments, a single compartments is embedded within a plurality of layers. In certain embodiments, a plurality of compartments is embedded within a plurality of layers. In certain embodiments, the skin tissues comprise a plurality of compartments. In certain embodiments, the compartments are in contact with each other. In certain embodiments, the skin tissues comprise a plurality of compartments disposed with separation of 10 μm or more between the compartments. In certain embodiments, the compartments comprise epidermal, dermal, hypodermal or non-cellular bio-inks. In certain embodiments, the compartment or plurality of compartments comprise a specialized cell type such as sebaceous cells, follicular cells, endothelial cells, muscle cells, smooth muscle cells, lymph nodes. In certain embodiments, the compartment is embedded in the epidermal layer. In certain embodiments, the compartment is embedded in the dermal layer. In certain embodiments, the compartment is embedded in the hypodermal layer. A compartment may be spherical, cuboidal, rectangular, rhomboidal or any irregular shape. In certain embodiments, the compartment extends through one or more layers forming a tube that is open at the surface.

In certain embodiments, a compartment is a conglomeration of a plurality of cells. In certain embodiments, a compartment is a conglomeration of greater than 10 cells. In certain embodiments, a compartment is a conglomeration of greater than 100 cells. In certain embodiments, a compartment is a conglomeration of greater than 500 cells. In certain embodiments, a compartment is a conglomeration of greater than 1,000 cells. In certain embodiments, a compartment is a conglomeration of greater than 5,000 cells. In certain embodiments, a compartment is a conglomeration of greater than 10,000 cells. In certain embodiments, a compartment is a conglomeration of greater than 50,000 cells.

In certain embodiments, a compartment is greater than 1 cell thick in its smallest dimension. In certain embodiments, a compartment is greater than 10 cells thick in its smallest dimension. In certain embodiments, a compartment is greater than 20 cells thick in its smallest dimension. In certain embodiments, a compartment is greater than 50 cells thick in its smallest dimension. In certain embodiments, a compartment is greater than 100 cells thick in its smallest dimension. In certain embodiments, a compartment is greater than 500 cells thick in its smallest dimension. In certain embodiments, a compartment is greater than 5000 cells thick in its smallest dimension.

In certain embodiments a compartment is greater than 5 μm thick in its smallest dimension. In certain embodiments, a compartment is greater than 10 μm thick in its smallest dimension. In certain embodiments, a compartment is greater than 20 μm thick in its smallest dimension. In certain embodiments, a compartment is greater than 50 μm thick in its smallest dimension. In certain embodiments, a compartment is greater than 100 μm thick in its smallest dimension. In certain embodiments, a compartment is greater than 500 cells thick in its smallest dimension.

In certain embodiments, the three-dimensional, engineered skin tissues, arrays, and methods described herein comprise a basal layer in contact with the dermal layer and the epidermal layer. In certain embodiments, the basal layer is between the epidermal and dermal layers. In certain embodiments, the basal layer comprises basal keratinocytes. In certain embodiments, the basal layer is a separate architecturally distinct layer. In certain embodiments, the basal keratinocytes display increased expression of KRT14 (CK14) compared to non-basal keratinocytes. In certain embodiments, the basal keratinocytes display increased expression of KRT5 (CK5) compared to non-basal keratinocytes. In certain embodiments, the basal layer is 1 cell thick. In certain embodiments, the basal layer is greater than 2 cells thick. In certain embodiments, the basal layer is greater than 3 cells thick. In certain embodiments, the basal layer is greater than 5 cells thick. In certain embodiments, the basal layer is greater than 10 cells thick. In certain embodiments, the basal layer is greater than 50 cells thick. In certain embodiments, the basal layer is less titan 100 cells thick. In certain embodiments, the basal layer is less than 50 cells thick. In certain embodiments, the basal layer is less than 10 cells thick.

In certain embodiments, the epidermal layer is a monolayer. In certain embodiments, the epidermal layer is greater than 1 cell thick. In certain embodiments, the epidermal layer is greater than 2 cells thick. In certain embodiments, the epidermal layer is greater than 3 cells thick. In certain embodiments, the epidermal layer is greater than 10 cells thick. In certain embodiments, the epidermal layer is greater than 50 cells thick. In certain embodiments, the epidermal layer is greater than 100 cells thick.

Its certain embodiments, the dermal layer is a monolayer. In certain embodiments, the dermal layer is greater than 1 cell thick. In certain embodiments, the dermal layer is greater titan 2 cells thick. In certain embodiments, the dermal layer is greater than 3 cells thick. In certain embodiments, the dermal layer is greater than 10 cells thick. In certain embodiments, the dermal layer is greater than 50 cells thick. In certain embodiments, the dermal layer is greater than 100 cells thick.

In certain embodiments, the hypodermal layer is a monolayer. In certain embodiments, the hypodermal layer is greater than 1 cell thick. In certain embodiments, the hypodermal layer is greater than 2 cells thick. In certain embodiments, the hypodermal layer is greater than 3 cells thick. In certain embodiments, the hypodermal layer is greater than 10 cells thick. In certain embodiments, the hypodermal layer is greater than 50 cells thick. In certain embodiments, the hypodermal layer is greater than 100 cells thick.

In some embodiments, the three-dimensional, engineered skin tissues, arrays, and methods described herein, allow for unique tissue architectures. Bio-inks are deposited to form layers or discrete compartments. In certain embodiments, the epidermal tissue and dermal tissue layers are separate, architecturally distinct layers that are in direct contact or separated by 1,2,3, 4. 5, 6, 7, 8, 9, 10, 15, 20 μm or more, including increments therein. In certain embodiments, the separation is due to the secretion and deposition of extracellular matrix between the two layers, which for the purposes of this disclosure is considered contact. In certain embodiments, a layer of non-cellular bio-ink is situated between the epidermal and dermal layers. In certain embodiments, the layer of non-cellular bio-ink is 10, 20, 30, 40, 50, 60, 70, 80, 90, or 100 μm or more thick. In certain embodiments, the epidermal cell layer is in contact with the dermal layer.

In certain embodiments, the epidermal cell layer or compartment is in continuous contact with the dermal layer or compartment. In certain embodiments, greater than 99% of the epidermal cell layer or compartment is in contact with the dermal layer or compartment . In certain embodiments, greater than 98% of the epidermal cell layer or compartment is in contact with the dermal layer or compartment. In certain embodiments, greater than 95% of the epidermal cell layer or compartment is in contact with the dermal layer or compartment. In certain embodiments, greater than 90% of the epidermal cell layer or compartment is in contact with the dermal layer or compartment. In certain embodiments, greater than 80% of the epidermal cell layer or compartment is in contact with the dermal layer or compartment. In certain embodiments, greater than 70% of the epidermal cell layer or compartment is in contact with the dermal layer or compartment. In certain embodiments, greater than 60% of the epidermal cell layer or compartment is in contact with the dermal layer or compartment. In certain embodiments, the epidermal cell layer is a monolayer. In certain embodiments, the epidermal cell layer is greater than 1, 2, 3, 4, 5, 6, 7, 8, 9, 10 or more layers thick. In certain embodiments, the epidermal cell layer is greater than 10, 20, 30, 40, 50, 60, 70, 80, 90, 100 or more layers thick. In certain embodiments, the epidermal cell layer is a monolayer. In certain embodiments, the dermal cell layer is greater than 1, 2, 3, 4, 5, 6, 7, 8, 9, 10 or more layers thick. In certain embodiments, the dermal cell layer is greater than 10, 20, 30, 40, 50, 60, 70, 80, 90, 100 or more cells thick. In certain embodiments, the epidermal cell layer is less than 1, 2, 3, 4, 5, 6, 7, 8, 9, 10 or more layers thick. In certain embodiments, the epidermal cell layer is less than 10, 20, 30, 40, 50, 60, 70, 80, 90, 100 or more layers thick. In certain embodiments, the dermal cell layer is less than 1, 2, 3, 4, 5, 6, 7, 8, 9, 10 or more layers thick. In certain embodiments, the dermal cell layer is less than 10, 20, 30, 40, 50, 60, 70, 80, 90, 100 or more cells thick.

In certain embodiments, the dermal cell layer or compartment is in contact with the hypodermal cell layer or compartment. In certain embodiments, the dermal cell layer or compartment is in continuous contact with the hypodermal cell layer or compartment. In certain embodiments, greater than 99% of the dermal cell layer or compartment is in contact with the hypodermal layer or compartment. In certain embodiments, greater than 98% of the dermal cell layer or compartment is in contact with the hypodermal layer or compartment. In certain embodiments, greater than 95% of the dermal cell layer or compartment is in contact with the hypodermal layer or compartment. In certain embodiments, greater than 90% of the dermal cell layer or compartment is in contact with the hypodermal layer or compartment. In certain embodiments, greater than 80% of the dermal cell layer or compartment is in contact with the hypodermal layer or compartment. In certain embodiments, greater than 70% of the dermal cell layer or compartment is in contact with the hypodermal layer or compartment. In certain embodiments, greater than 60% of the dermal cell layer or compartment is in contact with the hypodermal layer or compartment. In certain embodiments, the hypodermal cell layer is a monolayer. In certain embodiments, the hypodermal cell layer is greater than 1, 2, 3, 4, 5, 6, 7, 8, 9, 10 or more layers thick. In certain embodiments, the hypodermal cell layer is greater than 10, 20, 30, 40, 50, 60, 70, 80, 90, 100 or more layers thick. In certain embodiments, the hypodermal cell layer is a monolayer. In certain embodiments, the hypodermal cell layer is greater than 1, 2, 3, 4, 5, 6, 7, 8, 9, 10 or more layers thick. In certain embodiments, the dermal cell layer is greater than 10, 20, 30, 40, 50, 60, 70, 80, 90, 100 or more cells thick. In certain embodiments, the hypodermal cell layer is less than 1, 2, 3, 4, 5, 6, 7, 8, 9, 10 or more layers thick. In certain embodiments, the hypodermal cell layer is less than 10, 20, 30, 40, 50, 60, 70, 80, 90, 100 or more layers thick.

In certain embodiments, the thickness of the epidermal layer of the three-dimensional, engineered skin tissues can be varied. In certain embodiments, the thickness of the epidermal layer is between about 20 and about 500 μm. In certain embodiments, the thickness of the epidermal layer is between about 20 and about 400 μm. In certain embodiments, the thickness of the epidermal layer is between about 20 and about 300 μm. In certain embodiments, the thickness of the epidermal layer is between about 20 and about 200 pm. In certain embodiments, the thickness of the epidermal layer is between about 50 and about 500 μm. In certain embodiments, the thickness of the epidermal layer is between about 100 and about 500 μm. in certain embodiments, the thickness of the epidermal layer is between about 100 and about 200 μm. In certain embodiments, the thickness of the epidermal layer is greater than about 20 μm. In certain embodiments, the thickness of the epidermal layer is greater than about 30 μm. In certain embodiments, the thickness of the epidermal layer is greater than about 40 μm. In certain embodiments, the thickness of the epidermal layer is greater than about 50 μm. In certain embodiments, the thickness of the epidermal layer is greater than about 75 μm. In certain embodiments, the thickness of the epidermal layer is greater than about 100 μm. In certain embodiments, the thickness of the epidermal layer is greater than about 125 μm. In certain embodiments, the thickness of the epidermal layer is less than about 500 μm. In certain embodiments, the thickness of the epidermal layer is less than about 400 μm. In certain embodiments, the thickness of the epidermal layer is less than about 300 μm. In certain embodiments, the thickness of the epidermal layer is less than about 200 μm. In certain embodiments, the thickness of the epidermal layer is about 150 μm.

In certain embodiments, the thickness of the dermal layer of the three-dimensional, engineered skin tissues can be varied. In certain embodiments, the thickness of the dermal layer is between about 10 and about 1000 μm. In certain embodiments, the thickness of the dermal layer is between about 100 and about 1000 μm. In certain embodiments, the thickness of the dermal layer is between about 200 and about 1000 μm. In certain embodiments, the thickness of the dermal layer is between about 300 and about 1000 μm. In certain embodiments, the thickness of the dermal layer is between about 400 and about 1000 μm. In certain embodiments, the thickness of the dermal layer is between about 100 and about 900 μm. In certain embodiments, the thickness of the dermal layer is between about 100 and about 800 μm. In certain embodiments, the thickness of the dermal layer is between about 100 and about 700 μm. In certain embodiments, the thickness of the dermal layer is between about 100 and about 600 μm. In certain embodiments, the thickness of the dermal layer is at least about 100 μm. In certain embodiments, the thickness of the dermal layer is at least about 200 μm. In certain embodiments, the thickness of the dermal layer is at least about 300 μm. In certain embodiments, the thickness of the dermal layer is at least about 400 μm. In certain embodiments, the thickness of the dermal layer is less than about 2000 μm. In certain embodiments, the thickness of the dermal layer is less than about 1500 μm. In certain embodiments, the thickness of the dermal layer is less than about 1000 μm. In certain embodiments, the thickness of the dermal layer is less than about 900 μm. In certain embodiments, the thickness of the dermal layer is less than about 800 μm. In certain embodiments, the thickness of the dermal layer is less than about 700 μm. In certain embodiments, the thickness of the dermal layer is less than about 600 μm. In certain embodiments, the thickness of the dermal layer is about 500 μm.

In certain embodiments, the thickness of the hypodermal layer of the three-dimensional. engineered skin tissues can be varied hi certain embodiments, the thickness of the hypodermal layer is greater than about 20 μm. In certain embodiments, the thickness of the hypodermal layer is greater than about 50 μm. In certain embodiments, the thickness of the hypodermal layer is greater than about 40 μm. In certain embodiments, the thickness of the hypodermal layer is greater than about 50 μm. In certain embodiments, the thickness of the hypodermal layer is greater than about 75 μm. In certain embodiments, the thickness of the hypodermal layer is greater than about 100 μm. In certain embodiments, the thickness of the hypodermal layer is greater than about 200 μm. In certain embodiments, the thickness of the hypodermal layer is greater than about 300 μm. In certain embodiments, the thickness of the hypodermal layer is greater than about 400 μm. In certain embodiments, the thickness of the hypodermal layer is greater than about 500 μm. In certain embodiments, the thickness of the hypodermal layer is greater than about 125 μm. In certain embodiments, the thickness of the hypodermal layer is less than about 500 μm. In certain embodiments, the thickness of the hypodermal layer is less than about 400 μm. In certain embodiments, the thickness of the hypodermal layer is less than about 300 μm. In certain embodiments, the thickness of the hypodermal layer is less than about 200 μm. In certain embodiments, the thickness of the hypodermal layer is about 150 μm.

In certain embodiments, the dermal layer is attached to a biocompatible surface, and the epidermal layer is disposed on top of the dermal layer. In certain embodiments, the epidermal layer completely covers the dermal layer. In certain embodiments, the epidermal layer covers greater than 95% of the dermal layer. In certain embodiments, the epidermal layer or compartment covers greater than 90% of the hernial layer or compartment. In certain embodiments, the epidermal layer or compartment covers greater than 90% of the dermal layer or compartment. In certain embodiments, the epidermal layer or compartment covers greater than 70% of the dermal layer or compartment. In certain embodiments, the epidermal layer or compartment covers greater than 60% of the dermal layer or compartment. In certain embodiments, the epidermal layer or compartment covers greater than 50% of the dermal layer or compartment. In certain embodiments the epidermal layer or compartment covers greater than 40% of the dermal layer or compartment. In certain embodiments, the epidermal layer or compartment covers greater than 30% of the dermal layer or compartment. In certain embodiments, the epidermal layer or compartment covers greater than 20% of the dermal layer or compartment. In certain embodiments, the epidermal layer or compartment covers greater than 10% of the dermal layer or compartment.

In certain embodiments, the hypodermal layer is attached to a biocompatible surface, and the dermal layer is disposed on top of the dermal layer. In certain embodiments, the dermal layer completely covers the hypodermal layer. In certain embodiment, the dermal layer covers greater than 95% of the hypodermal layer. In certain embodiments, the dermal layer covers greater than 90% of the hypodermal layer. In certain embodiments, the dermal layer covers greater than 90% of the dermal layer. In certain embodiments, the dermal layer covers greater than 70% of the hypodermal layer. In certain embodiments, the dermal layer covers greater than 60% of the hypodermal layer. In certain embodiments, the dermal layer covers greater than 50% of the hypodermal layer.

In some aspects the three-dimensional, engineered skin tissues are substantially flat. In some aspects the skin tissues are flat with less than 10% curvature. In some aspects the skirt tissues are substantially flat with less than 20% curvature. In some embodiments, the surface area of the skin tissues is at least 0.01 cm². In some embodiments, the surface area of the skin tissues is at least 0.02 cm². In some embodiments, the surface area of the skin tissues is at least 0.03 cm². In some embodiments, the surface area of tire skirt tissues is at least 0.04 cm². In some embodiments, the surface area of the skin tissues is at least 0.05 cm². In some embodiments, the surface area of the skin tissues is at least 0.06 cm². In some embodiments, the surface area of skin tissues is at least 0.07 cm². In some embodiments. the surface area of the skin tissues is at least 0.08 cm². In some embodiments, the surface area of the skin tissues is at least 0.09 cm². In some embodiments, the surface area of the skin tissues is at least 0.10 cm². In some embodiments, the surface area of the renal tubule model is at least 0.11 cm². In some embodiments the surface area of the skin tissues is at least 0.12 cm². In some embodiments, the surface area of the skin tissues is less than 0.2 cm². In some embodiments, the surface area of the skin tissues is less than 0.4 cm². In some embodiments, the surface area of the skin tissues is less than 0.5 cm². In some embodiments. the surface area of the skin tissues is less than 0.8 cm². In some embodiments, the surface area of skin tissues is less than 1.0 cm². In some embodiments, the surface area of skin tissues is less than 2.0 cm². In some embodiments, the surface area of skin tissues is less than 3.0 cm². In some embodiments, the surface area of skin tissues is less than 4.0 cm². In some embodiments. the surface area of skin tissues is less than 5.0 cm².

In certain embodiments, the tissue can be any suitable shape such as square, oval, ellipsoid, circular, trapezoidal, rhomboidal, spherical, cuboid al, and the like.

Methods of Manufacture

Referring to FIG. 3, for example, in a particular embodiment, continuous deposition bioprinting techniques are used to print a layered tissue onto a collagen-coated printing surface. In this embodiment, dermal cells are bioprinted onto a transwell surface to form a dermal layer. Subsequently, epidermal cells are bioprinted on top of the dermal cells to form an epidermal layer. Finally, the layered tissue is allowed to mature in a cell culture environment.

Referring to FIG. 4. in a particular embodiment, an engineered skin tissue containing dermal and epidermal layers bioprinted using continuous deposition techniques was allowed to mature for 48 hours post-printing.

An advantage of the engineered tissues and methodologies described herein is that they allow retention of the shape of the structure without compromising the functionality of the original cell types. The shape of the bioprinted structure, is advantageously maintained by multiple approaches. In Example 1, the printed bio-ink structure utilizes Novogel® 3.0, which is cross-linked at the time of the printing to maintain shape and lyase treated at a later time point while maturing at 37° C. Because the cross-linking step involves exposure to high concentrations of calcium ions, which could impact keratinocyte biology, we sought to separate this cross-linking step from the deposition of the epidermal layer. The invention also incorporates a novel aerosol spray printing method into a 3D tissue model. The aerosol spray approach provides a unique method compared to the continuous deposition method in that it allows the creation of a thinner layer, and allows you to readily deposit material onto an existing tissue layer after a period of maturation. This is advantageous because it may produce a tissue that better mimics native tissue in vivo. This can also be advantageous because it can reduce the number of cells required and allow for bioprinting with limited cell populations. This aerosol spray method can be applied to create multiple layers at multiple time points. For example, this method could be used for spraying first with undifferentiated keratinocytes followed by spraying with differentiated keratinocytes to better mimic native skin (FIG. 5).

The aerosol spray bioprinting techniques described herein allow for the spray of materials that include, for example, a cell suspension, media, bio-ink, biosupport material, or a combination thereof. In Ex ample 1, the aerosol spray approach is utilized to spray a thin layer of epidermal cells. In some embodiments, the engineered tissues and method-ologics described herein highlight the ability to spray single cells at a resolution of one cell layer thickness and the ability to spray cell aggregates. The sprayed layer could, however, also be modified by changing parameters including but not limited to spray material velocity, distance, time, volume, and viscosity. For the creation of the epidermal layer, cells are optionally sprayed onto other bioprinted layers to result in a full-thickness model, or directly onto transwell or other matrix coated surfaces to specifically generate an epidermal model. The spray method is optionally utilized to embed sprayed material into a soft surface such as biosupport material or Novogel®. For example, a dermal layer could be created by spraying fibroblasts into a collagen gel (FIG. 6). In some embodiments, this approach generates a dermal layer that more closely resembles native dermis, where a more sparse cellular density is observed than is usually achieved by continuous deposition methods.

The aerosol spray method is unique when compared to continuous deposition printing in that it does not require a flat printing surface, such as a transwell membrane, to zero the initial printing position in the x, y, and z-axes. The aerosol spray method is optionally used to apply a layer to an uneven surface such as a structure previously printed by continuous deposition. For example, in Example 2 the aerosol spray bioprinting methodologies described herein are utilized to spray a thin layer of epidermal cells onto previously primed layer of dermal cells. In some embodiments, this temporal spacing allows the initial layer to express certain proteins that enable adherence and proper stratification of the subsequent epidermal layer.

Regardless of the printing method used, a variety of factors are optionally modified to promote proliferation and/or differentiation of printed tissue cells. In some cases, dermal media, epidermal media, or a combination of dermal and epidermal media is added to the skin tissue constructs. In addition, the media composition is optionally changed at different points in the tissue lifetime to promote the desired biology. The tissue constructs are optionally moved to an air liquid interface or subjected to atmospheric changes such as modification of humidity or $CO_2$. A hypothetical experimental design combining both printing approaches is shown in FIG. 7.

In certain embodiments, the three-dimensional, engineered, biological skin tissues disclosed herein are produced by an additive manufacturing process. The additive manufacturing process for three-dimensional, engineered, biological skin tissues herein allows customized fabrication of three-dimensional, engineered, biological skin tissues for in vitro and therapeutic purposes. This is significant in that the tissues are fabricated due to a user specified design. In certain embodiments, the three-dimensional, engineered, biological skin tissues contain only the cells that the user specifies (e.g., uses as inputs to the additive manufacturing process). In certain embodiments, three-dimensional, engineered, biological skin tissues contain only the cell types that the user specifies. In certain embodiments, the three-dimensional, engineered, biological skin tissues contain only the number of cells or concentration of cells that the user specifics. In certain embodiments, the three-dimensional, engineered, biological skin tissues contain cells that have been treated with a small molecule, therapeutic molecule, or therapeutic substance before or during fabrication. In certain embodiments, the three-dimensional, engineered, biological skin tissues contain biocompatible or tissue culture plastics, biocompatible synthetic polymers cross linkable gels, reversibly cross-linked gels and other non-cellular constituents.

Bioprinting

In some embodiments, at least one component of the engineered skin tissues/constructs, and arrays thereof is bioprinted. In further embodiments, bioprinted constructs are made with a method that utilizes a rapid prototyping technology based on three-dimensional, automated, computer-aided deposition of cells, including cell solutions, cell suspensions, cell-comprising gels or pastes, cell concentrations, multicellular bodies (e.g., cylinders, spheroids, ribbons, etc.), and optionally, confinement material onto a biocompatible support surface (e.g., composed of hydrogel and/or a porous membrane) by a three-dimensional delivery device (e.g., a bioprinter). As used herein, in some embodiments, the term "engineered," when used to refer to tissues and/or organs means that cells, cell solutions, cell suspensions, cell-comprising gels or pastes, cell concentrates, multicellular aggregates, and layers thereof are positioned to form three-dimensional structures by a computer-aided device (e.g., a bioprinter) according to a computer script. In further embodiments, the computer script is, for example, one or more computer programs, computer applications, or computer modules. In still further embodiments, three-dimensional tissue structures form through the post-printing adhesion of cells or multicellular bodies which, in some cases, is similar to self-assembly phenomena in early morphogenesis.

While a number of methods are available to arrange cells, multicellular aggregates, and/or layers thereof on a biocompatible surface to produce a three-dimensional structure including manual placement, positioning by an automated, computer-aided machine such as a bioprinter is advantageous. Advantages of delivery of cells or multicellular bodies with this technology include rapid, accurate, and reproducible placement of cells or multicellular bodies to produce constructs exhibiting planned or pre-determined orientations or patterns of cells, multicellular aggregates and/or layers thereof with various compositions. Advantages also include assured high cell density, while minimizing cell damage.

In some embodiments, the method of bioprinting is continuous and/or substantially continuous. A non-limiting example of a continuous bioprinting method is to dispense bio-ink (i.e., cells, cells combined with an excipient or extrusion compound, or aggregates of cells) from a bioprinter via a dispense tip (e.g., a syringe, needle, capillary tube, etc.) connected to a reservoir of bio-ink. In further non-limiting embodiments, a continuous bioprinting method is to dispense bio-ink in a repeating pattern of functional units. In various embodiments, a repeating functional unit has any suitable geometry, including, for example, circles, squares, rectangles, triangles, polygons, and irregular geometries, thereby resulting in one or more tissue layers with planar geometry achieved via spatial patterning of distinct bio-inks and/or void spaces. In further embodiments, a repeating pattern of bioprinted function units comprises a layer and a plurality of layers are bioprinted adjacently (e.g., stacked) to form an engineered tissue or organ with laminar geometry. In various embodiments, 2, 3, 4, 5, 6, 7, 8, 9, 10, 11, 12, 13, 14, 15, or more layers are bioprinted adjacently (e.g., stacked) to form an engineered tissue or organ. In further embodiments, one or more layers of a tissue with laminar geometry also has planar geometry.

In some embodiments, the method of bioprinting is discontinuous. A non-limiting example of discontinuous bioprinting is when bio-ink or cells are dispensed, and then the flow of bio-ink or cells is stopped, paused for a certain amount of time, and then started again. This can allow for different bio-inks or cells, or the same bio-inks or cells to be layered with a delay in printing of the layers. In some embodiments, the discontinuous bioprinting is achieved using an aerosol spray type of bioprinting, wherein cells are applied to an existing tissue layer or surface using an aerosol spray technology. In some embodiments, a single layer or plurality of layers of dermal cells or bio-inks are deposited, followed by a temporal delay in deposition of a single layer or plurality of layers epidermal cells or bio-inks. In some embodiments, the deposition of the epidermal cells is by an aerosol spray.

Any of the different bio-inks of this disclosure can be deposited by various techniques to form layers of the three-dimensional, engineered, biological skin tissue. Any of the layers can be deposited by extrusion (continues or discontinuous), spraying (ink-jetting or aerosol spraying). In certain embodiments, the hypodermal bio-ink is deposited by extrusion onto a surface In certain embodiments, the hypodermal bio-ink is deposited by extrusion onto a surface. In certain embodiments, the dermal bio-ink is deposited by extrusion onto a surface. In certain embodiments, the epidermal bio-ink is deposited by extrusion onto a surface. In certain embodiments, a non-cellular matrix bio-ink is deposited by extrusion onto a surface. In certain embodiments, the hypodermal bio-ink is deposited by spraying onto a surface. In certain embodiments, the hypodermal bio-ink is deposited by spraying onto a surface. In certain embodiments, the dermal bio-ink is deposited by spraying onto a surface. In certain embodiments, the epidermal bio-ink is deposited by spraying onto a surface. In certain embodiments, the non-cellular matrix bio-ink is deposited by spraying onto a surface. In certain embodiments, the hypodermal bio-ink is not deposited by extrusion onto a surface. In certain embodiments, the hypodermal bio-ink is not deposited by extrusion onto a surface. In certain embodiments, the dermal bio-ink is not deposited by extrusion onto a surface. In certain embodiments, the epidermal bio-ink is not deposited by extrusion onto a surface. In certain embodiments, a non-cellular matrix bio-ink is not deposited by extrusion onto a surface. In certain embodiments, the hypodermal bio-ink is not deposited by spraying onto a surface. In certain embodiments, the hypodermal bio-ink is not deposited by spraying onto a surface. In certain embodiments, the dermal bio-ink is not deposited by spraying onto a surface. In certain embodiments, the epidermal bio-ink is not deposited by spraying onto a surface. In certain embodiments, the non-cellular matrix bio-ink is not deposited by spraying onto a surface.

In certain embodiments, deposition of the epidermal bio-ink occurs after deposition of the dermal bio-ink. In certain embodiments, deposition of the epidermal bio-ink occurs before maturation of the deposited dermal bio-ink. In certain embodiments, deposition of the epidermal layer is temporally delayed before it is deposited on the dermal bio-ink. In certain embodiments, the delay is greater than 1, 2, 3, 4, 5, 6, 7, 8, 9. milliseconds. In certain embodiments, the delay is greater than 10 milliseconds. In certain embodiments, the delay is greater than 20, 30, 40, 50, 60, 70, 80, 90 or 100, milliseconds. In certain embodiments, the delay is greater than 200, 300, 400, 500, 600, 700, 800, 900 or 1000, milliseconds. In certain embodiments, the delay is greater than 1, 2, 3, 4, 5, 6, 7, 8, 9, 10 seconds. In certain embodiments, the delay is greater than 10, 20, 30, 40, 50, or 60 seconds. In certain embodiments, the delay is greater than 1, 2, 3, 4, 5, 6, 7, 8, 9, or 10 minutes. In certain embodiments, the delay is greater than 10, 20, 30, 40, 50, or 60 minutes. In certain embodiments, the delay is greater than 1, 2, 3, 4, 5, 6, 7, 8, 9, 10, 11, 12, 13, 14, 15, 16, 17, 18, 19, 20, 21, 22, 23, or 24 hours. In certain embodiments, the delay is greater than 1, 2, 3, 4, 5, 6, or 7 days. In certain embodiments, the delay is greater than 1, 2, 3, or 4 weeks. In certain embodiments, the delay is less than 1, 2, 3, 4, 5, 6, 7, 8, 9, milliseconds. In certain embodiments, the delay is less than 10 milliseconds. In certain embodiments, the delay is less than 20, 30, 40, 50, 60, 70, 80, 90 or 100, milliseconds. In certain embodiments, the delay is less than 200, 300, 400, 500, 600, 700, 800, 900 or 1000, milliseconds. In certain embodiments, the delay is less than 1, 2, 3, 4, 5, 6, 7, 8, 9, 10 seconds. In certain embodiments, the delay is less than 10, 20, 30, 40, 50, or 60 seconds. In certain embodiments, the delay is less than 1, 2, 3, 4, 5, 6, 7, 8, 9, or 10 minutes. In certain embodiments, the delay is less than 10, 20, 30, 40, 50, or 60 minutes. In certain embodiments, the delay is less than 1, 2, 3, 4, 5, 6, 7, 8, 9, 10, 11, 12, 13, 14, 15, 16, 17, 18, 19, 20, 21, 22, 23, or 24 hours. In certain embodiments, the delay is less than 1, 2, 3, 4, 5, 6, or 7 days. In certain embodiments, the delay is less than 1, 2, 3, or 4 weeks.

In certain embodiments, the skin tissue also comprises a test substance or agent, and can be administered to the tissue in many ways as shown in FIG. 26, the test substance can be applied to the apical, ventral, basal, or lateral surface of any single layer or any plurality of layers bioprinted. The test substance can be applied to the entirety of the surface or a portion of the surface. The test substance can fee added between two layers that are the same cell type or a different cell type, embedded within a single layer or plurality of layers, or mixed homogenously or heterogeneously throughout a single layer or a plurality of layers. The test substance can be applied via an aerosol spray type mechanism, an extrusion mechanism, a syringe a pipette tip, or a blunted object.

This invention discloses the automated administration of substances for toxicology testing through utilization of a bioprinting platform including but not limited to ink jet aerosolized spray, dispense nozzle, and continuous deposition. Bioprinting allows for spatially defined, precise deposition of predetermined volumes and geometries onto printing surfaces. In one embodiment, tissues are printed onto surfaces containing printed test substances. In a second embodiment, substances are administered by printing onto printed tissues. In some instances test substances can be applied topically to a tissue simultaneously during printing, in other instances immediately following printing, and in yet other instances at a later time point to mature tissue. For example, a test substance can be added to a mature tissue to model transdermal administration in which the substance must pass through fully formed stratum corneum with barrier function. In a third embodiment, substances can be incorporated into a tissue. In some cases, a test substance can be added as a layer between printed tissues. In other cases, substances are printed as a homogenous mixture within any layer of the skin tissue, or within all layers of the skin tissue In vet other cases, a substance can be embedded within a tissue layer. For example, a test substance can be embedded into the dermal layer of a full thickness skin tissue by syringe deposition to model a parenteral subcutaneous injection.

Test substances may be applied directly to the apical surface of the tissue to model transdermal delivery and lest barrier function, or administered to ventral or lateral sides of the tissue to model permeation or distribution as a gradient. In other applications, tissues are completely immersed in the substance. In some instances, a bioprinted matrix or membrane may act as an adhesive or aid to administer, dispense or disperse a test substance similar to a transdermal patch. In other instances addition or adherence can be aided in combination or separately by a patch of a non-bioprinted material such as gauze or nylon mesh. Substances can be also administered manually, for example, as dispensed by pipet tip, swabbed, or applied by a blunted object.

Test substances can be liquid, including solutions, suspensions, and emulsions. Substances can also be solids, such as powders and granules, or semi solids such as pastes. Substances tested can be hydrous or anhydrous with varying levels of viscosity and administered in the form of but not limited to a liquid, oil, gel, loam, ointment, or cream. Substances may be applied aerosolized into a liquid aerosol such as a spray or fog. Substances may also be administered as a solid aerosol such as a smoke or dust. Substances may also be administered combined with a Novogel®. Any of these test substances may be applied in an automated way, by bioprinting or manually.

In some embodiments, the test substance is any substance requiring toxicology, pharmaceutical or cosmetic testing. The test substance is a composition containing any whole, part, active or inactive ingredient of a chemical mixture, irritant, chemical, pharmaceutical, alcohol, lipid, phospholipid, acid, base, peroxide, oxidizing agent, reducing agent, detergent, surfactant, nutracentical, vitamin, pro-vitamin, mineral, amino acid, DNA, RNA, protein, enzyme, allergen, pet allergen, plant based allergen, mold, dust insect venom, virus, bacteria, fungus, immunological adjuvant, antibiotic, anti fungal, sunscreen, insect repellant, cosmetic, botanical, chap stick, lipstick, mascara, eye shadow, foundation, powder, make up remover, soap, body wash, face wash, hand soap, dishwashing soap, shampoo, cologne, perfume, aftershave, shaving lotion, shaving gel, shaving cream, lubricant, conditioner, hair-dye, hair remover, moisturizer, antiwrinkle cream, laundry detergent, fabric softener or latex. In certain embodiments, the test substance is not chemical in nature, examples include, but are not limited to, light sunlight, ultraviolet light, X-rays, electromagnetic radiation, electrical impulses applied to or in the vicinity of the tissue, lasers, heat, cold, acoustic waves, or mechanical stress. In certain embodiments, the test substance is a plurality of substances applied simultaneously or in sequence. The composition applied can be any pharmaceutically, dermatologically or cosmetically acceptable substance. The substance can be a lotion, ointment, aqueous solution, aerosol, mist, suspension, colloid, tincture, alcohol based or lipid based solution. In certain embodiments, the composition contains DMSO.

Pre-Formed Scaffold

In some embodiments, disclosed herein are engineered, engraftable skin tissues that are free or substantially free of any pre-formed scaffold. In further embodiments, "scaffold" refers to synthetic scaffolds such as polymer scaffolds and porous hydrogels, non-synthetic scaffolds such as preformed extracellular matrix layers, dead cell layers, and decellularized tissues, and any other type of pro-formed scaffold that is integral to the physical structure of the engineered tissue and or organ and not removed from the tissue and/or organ. In still further embodiments, decellularized tissue scaffolds include decellularized native tissues or decellularized cellular material generated by cultured cells in any manner; for example, cell layers that are allowed to die or are decellularized, leaving behind the ECM they produced while living.

In some embodiments, the engineered skin tissues constructs and arrays thereof do not utilize any pro-formed scaffold, e.g., for the formation of the tissue, any layer of the tissue, or formation of the tissue's shape. As a non-limiting example, the engineered skin tissues of the present invention do not utilize any pro-formed, synthetic scaffolds such as polymer scaffolds, pre-formed extracellular matrix layers, or any other type of pro-formed scaffold at the time of manufacture or at the time of use. In some embodiments, the engineered skin tissues are substantially free of any preformed scaffolds. In further embodiments, the cellular components of the tissues contain a detectable, but trace or trivial amount of scaffold, e.g., less than 2.0%, less than 1.0%, or less than 0.5% of the total composition. In still further embodiments, trace or trivial amounts of scaffold are insufficient to affect long-term behavior of the tissue, or array thereof, or interfere with its primary biological function. In additional embodiments, scaffold components are removed post-printing, by physical, chemical, or enzymatic methods, yielding an engineered tissue that is free or substantially-free of scaffold components.

In some embodiments, the engineered skin tissues free, or substantially free, of pre-formed scaffold disclosed herein are in stark contrast to those developed with certain other methods of tissue engineering in which a scaffolding material is first formed, and then cells are seeded onto the scaffold, and subsequently the cells proliferate to fill and take the shape of the scaffold for example. In one aspect, the methods of bioprinting described herein allow production of viable and useful tissues that are free or substantially free of pre-formed scaffold. In another aspect, the cells of the invention are, in some embodiments, held in a desired three-dimensional shape using a confinement material. The confinement material is distinct from a scaffold at least in the fact that the confinement material is temporary and/or removable from the cells and/or tissue.

Biocompatible Surfaces

In some embodiments, the engineered skin tissues construct ate secured to a biocompatible surface on one or more sides. In some embodiments, the engineered skin tissues/constructs are secured to a biocompatible surface 1, 2, 3, 4 or more sides. Many methods are suitable to secure a tissue to a biocompatible surface. In various embodiments, a tissue is suitably secured to a biocompatible surface, for example, along one or more entire sides, only at the edges of one or more sides, or only at the center of one or more sides. In various further embodiments, a tissue is suitably secured to a biocompatible surface with a holder or carrier integrated into the surface or associated with the surface. In various further embodiments, a tissue is suitably secured to a biocompatible surface with one or more pinch-clamps or plastic nubs integrated into the surface or associated with the surface. In some embodiments, a tissue is suitably secured to a biocompatible surface by cell-attachment to a porous surface. In some embodiments, the pore size of the surface can be greater than 0.2 ρm. In some embodiments, the pore size of the surface can be greater than 1 μm. In some embodiments, a tissue is suitably secured to a biocompatible surface by cell-attachment to a porous membrane. In some embodiments, the engineered skin tissues constructs are held in an array configuration by affixation to a biocompatible surface on one or more sides. In further embodiments, the tissue is affixed to a biocompatible surface on 1, 2, 3, 4, or more sides. In some embodiments, the biocompatible surface any surface that docs not pose a significant risk of injury or toxicity to the tissue or an organism contacting the tissue. In farther embodiments, the biocompatible surface is any surface suitable for traditional tissue culture methods. Suitable biocompatible surfaces include, by way of non-limiting examples, treated plastics, membranes, porous membranes, coated membranes, coated plastics, metals, coated metals, glass, treated glass, and coated glass, wherein suitable coatings include hydrogels, ECM components, chemicals, proteins, etc., and coatings or treatments provide a means to stimulate or prevent cell and tissue adhesion to the biocompatible surface. In certain embodiments, the biocompatible surface is flexible. In certain embodiments, the biocompatible surface is non-static fin motion) at the rime of bioprinting. In certain embodiments, the biocompatible surface is not flat. The biocompatible surface could be a mold or form shaped like a human or other mammalian body part, or is curved.

In some embodiments, securing of an engineered tissue to a biocompatible surface on one or more sides facilitates subjecting the tissue to shear force, caused by fluid flow. In further embodiments, the engineered skin tissues constructs are subjected to shear force, caused by fluid flow. In various embodiments, the engineered skin tissues are subjected to shear force on 1, 2, 3, 4, or more sides. In further embodiments, the engineered skin tissues constructs are subjected to recirculation, perfusion, or agitation of the liquid nutrients that contact the tissues on one or more exposed surfaces.

Arrays

In some embodiments, disclosed herein are arrays of engineered skin tissues/constructs. In some embodiments. an "array" is a scientific tool including an association of multiple elements spatially arranged to allow a plurality of tests to be performed on a sample, one or more tests to be performed on a plurality of samples, or both. In some embodiments, the arrays are adapted for. or compatible with, screening methods and devices, including those associated with medium- or high-throughput screening In further embodiments, an array allows a plurality of tests to be performed simultaneously. In further embodiments, an array allows a plurality of samples to be tested simultaneously. In some embodiments, the arrays are cellular microarrays. In farther embodiments, a cellular microarray is a laboratory tool that allows for the multiplex interrogation of living cells on the surface of a solid support. In other embodiments, the arrays are tissue microarrays. In further embodiments, tissue microarrays include a plurality of separate tissues or tissue samples assembled in an array to allow the performance of multiple biochemical, metabolic, molecular, or histological analyses.

In some embodiments, the engineered skin tissues/constructs each exist in a well of a biocompatible multi-well container. In some embodiments, each tissue is placed into a well. In other embodiments, each tissue is bioprinted into a well. In further embodiments, the wells are coated. In various further embodiments, the wells are coated with one or more of: a biocompatible hydrogel, one or more proteins, one or more chemicals, one or more peptides, one or more antibodies, and one or more growth factors, including combinations thereof. In some embodiments, the wells are coated with NovoGel®. In other embodiments, the wells are coated with agarose. In some embodiments, each tissue exists on a porous, biocompatible membrane within a well of a biocompatible multi-well container. In some embodiments, each well of a multi-well container contains two or more tissues.

In some embodiments, the arrays of engineered tissues, including skin tissues, constructs, comprise an association of two or more elements. In various embodiments, the arrays comprise an association of 2, 3, 4, 5,6, 7, 8, 8, 10,11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or 1,000 elements, including increments therein. In further embodiments, each element comprises one or more cells, multicellular aggregates, tissues, organs, or combinations thereof.

In some embodiments, the arrays of engineered tissues, including skin tissues/constructs, comprise multiple elements spatially arranged in a pre-determined pattern. In further embodiments, the pattern is any suitable spatial arrangement of elements. In various embodiments, patterns of arrangement include, by way of non-limiting examples, a two-dimensional grid, a three-dimensional grid, one or more lines, arcs, or circles, a series of rows or columns, and the like. In further embodiments, the pattern is chosen for compatibility with medium- or high-throughput biological assay or screening methods or devices.

In various embodiments, the cell types and/or source of the cells used to fabricate one or more tissues in an array are selected based on a specific research goal or objective. In further various embodiments, the specific tissues in an array are selected based on a specific research goal or objective. In some embodiments, one or more specific engineered skin tissues are included in an array to facilitate investigation of a particular disease or condition. In some embodiments, one or more specific engineered skin tissues are included in an array to facilitate investigation of a disease or a condition of a particular subject. In further embodiments, one or more specific engineered skin tissues within the array are generated with one or more cell types derived front two or more distinct human donors. In some embodiments, each tissue within the array is substantially similar with regard to cell types, sources of cells, layers of cells, ratios of cells, and methods of construction, size, shape, and the like. In other embodiments, one or more of the tissues within the array is unique with regard to cell types, sources of cells, layers of cells, ratios of cells, methods of construction, size, shape, and the like. In various embodiments, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, or more of the tissues within the array, including increments therein, is/are unique, in other various embodiments, 1, 2, 3, 4, 5, 6, 7, 8, 9. 10, 15, 20, 25, 30, 35, 40, 45, 50, 55, 60, 65, 70, 75, 80, 85, 90, 91, 92, 93, 94, 95, 96, 97, 98, 99, or 100% of the tissues within the array, including increments therein, is/are unique.

In some embodiments, each tissue within the array is maintained independently in culture. In further embodiments, the culture conditions of each tissue within the array are such that they are isolated from the other tissues and cannot exchange media or factors soluble in the media. In other embodiments, two or more individual tissues within the array exchange soluble factors. In further embodiments, the culture conditions of two or mote individual tissues within the array are such that they exchange media and factors soluble in the media with other tissues. In various embodiments, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, or more of the tissues within the array, including increments therein, exchange media and or soluble factors. In other various embodiments, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of the tissues within the array, including increments therein, exchange media and/or soluble factors.

In certain embodiments, tissues within the array are spaced at regular intervals in a repealing pattern. In certain embodiments, tissues within the array are spaced at least 10 μm but no more than 1000 μm apart. In certain embodiments, tissues within the array are spaced at least 10 μm but no more than 500 μm apart. In certain embodiments, tissues within the array are spaced at least 10 μm but no more than 200 μm apart. In certain embodiments, tissues within the array are spaced at least 20 μm but no more than 1000 μm apart. In certain embodiments, tissues within the array are spaced at least 50 μm but no more than 1000 μm apart. In certain embodiments, tissues within the array are spaced at least 100 μm but no more than 1000 μm apart. In certain embodiments, tissues within the array are spaced at least 20 μm apart. In certain embodiments, tissues within the array are spaced at least 50 μm apart. In certain embodiments, tissues within the array are spaced at least 100 μm apart.

In Vitro Assays

In some embodiments, the engineered skin tissues and arrays disclosed herein are for use in in vitro assays. In some embodiments, an "assay" is a procedure for testing or measuring the presence or activity of a substance (e.g., a chemical, molecule, biochemical, drug, etc.) in an organic or biologic sample (e.g., cell aggregate, tissue, organ, organism, etc.). In further embodiments, assays include qualitative assays and quantitative assays. In still further embodiments, a quantitative assay measures the amount of a substance in a sample.

In various embodiments, the engineered skin tissues and arrays are for use in, by way of non-limiting examples, image-based assays, measurement of secreted proteins, expression of markers, and production of lipids, proteins or mRNAs. In various further embodiments, the engineered skin tissue and arrays are for use in assays to detect or measure one or more of; barrier function, molecular binding (including radio ligand binding), molecular uptake, activity (e.g., enzymatic activity and receptor activity, etc.), gene expression, protein expression, protein modifications (non-limiting examples include: phosphorylation, ubiquitinahon, acetylation, glycosylation, lipidation, etc.), receptor agonism, receptor antagonism, cell signaling, apoptosis, DNA damage, stress response, cohesion, permeability, inflammation, pigmentation, chemosensitivity, transfection, cell migration, chemotaxis, cell viability, cell proliferation, safety, efficacy, metabolism, toxicity, infectivity, and abuse liability. In various embodiments, the skin tissue are for toxicology, pharmaceutical or cosmetic testing.

In some embodiments, the engineered skin tissues and arrays are for use in immunoassays. Immunoassays include, for example, flow cytometry, high throughput or low throughput image analysis, immunoprecipitation. radio-immunoassay (RIA), ELISA, western blot, homogenous assays, such as AlphaLISA™ and related technologies that rely on time resolved fluorescence or fluorescence resonance energy transfer (FRET). In further embodiments, immunoassays are competitive immunoassays or noncompetitive immunoassays. In a competitive immunoassay, for example, the antigen in a sample competes with labeled antigen to bind with antibodies and the amount of labeled antigen bound to the antibody site is then measured. In a noncompetitive immunoassay (also referred to as a "sandwich assay"), for example, antigen in a sample is bound to an antibody site; subsequently, labeled antibody is bound to the antigen and the amount of labeled antibody on the site is then measured.

In some embodiments, the engineered skin tissues and arrays are for use in metabolic conversion or permeability assays. Assays include, for example, 3-[4,5-dimethylthiazol-2-yl]-2,5 diphenyl tetrazolium bromide (MTT), resazurin, lactate dehydrogenase (LDH), calcein AM substrates, related dyes, and technologies that rely on fluorescence or absorbance.

In some embodiments, the engineered skin tissue and arrays are for use in enzyme-linked immunosorbent assays (ELISA). In further embodiments, an ELISA is a biochemical technique used to detect the presence of an antibody or an antigen in a sample. In ELISA, for example, at least one antibody with specificity for a particular antigen is utilized. By way of further example, a sample with an unknown amount of antigen is immobilized on a solid support (e.g., a polystyrene microtiter plate) either non-specifically (via adsorption to the surface) or specifically (via capture by another antibody specific to the same antigen, in a "sandwich" ELISA). By way of still further example, after the antigen is immobilized, the detection antibody is added, forming a complex with the antigen. The detection antibody is, for example, covalently linked to un enzyme, or is itself detected by a secondary antibody that is linked to an enzyme through bioconjugarion.

For example, in some embodiments, an array, microarray, or chip of cells, multicellular aggregates, or tissues is used for drug screening or drug discovery. In further embodiments, an array, microarray, or chip of tissues is used as part of a kit for drug screening or drug discovery. In some embodiments, each engineered skin tissue/construct exists within a well of a biocompatible multi-well container, wherein the container is compatible with one or more automated drug screening procedures and/or devices. In further embodiments, automated drug screening procedures and/or devices include any suitable procedure or device that is computer or robot-assisted.

In further embodiments, arrays for drug screening assays or drug discovery assays are used to research or develop drugs potentially useful in any therapeutic area. In still further embodiments, suitable therapeutic areas include, by way of non-limiting examples, infectious disease, hematology, oncology, pediatrics, cardiology, central nervous system disease, neurology, gastroenterology, hepatology, urology, infertility, ophthalmology, nephrology, orthopedics, pain control, psychiatry, pulmonology, vaccines, wound healing, physiology, pharmacology, dermatology, gene therapy, toxicology, and immunology.

In some embodiments, the engineered skin tissue and arrays are for use in cell-based screening In bather embodiments, the cell-based screening is for one or more infectious diseases such as viral, fungal, bacterial or parasitic infection. In further embodiments, the cell-based screening is for skin cancer, including melanoma, basal cell carcinoma, and squamous cell carcinoma. In further embodiments, the cell-based screening is for dermatitis, including, atopic dermatitis, contact dermatitis, dermatitis herpetiformis, neurodermatitis and seborrheic dermatitis. In further embodiments, the cell-based screening is for psoriasis. In further embodiments, the cell-based screening is for one eczema, including xerotic eczema, discoid eczema, venous eczema, and autoeczematization. In further embodiments, the cell-based screening is for keratosis including actinic keratosis (also known as solar keratosis), hydrocarbon keratosis, keratosis pilaris (KP, also known as follicular keratosis), and seborrheic keratosis. In further embodiments, the cell-based screening is for acne. In other embodiments, the engineered skin tissues and arrays are for use in the study of cancer initiation, progression, or metastasis. In still further embodiments, the engineered skin tissues and arrays are for use in the study of the interaction of other cell types, such as cancer cells, pathogen-bearing cells, pathogenic cells, immune cells, blood-derived cells, or stem/progenitor cells.

In some embodiments, the constructs or arrays thereof are for use in assessing the performance of biologies, including antibodies, mammalian cells, bacteria, biologically-active proteins, hormones, etc. In some embodiments, the construct or arrays thereof are for use to detect, quantify, and study immunologic sampling by Langerhans cells, including the effects of gram-negative or gram-positive antigen-stimulated signaling from Langerhans cells, macrophages, T cell or B-cells to bordering skin cells. In other embodiments, the skin constructs or arrays thereof are useful in the study of cancer initiation, progression, or metastasis. In other embodiments, the skin constructs or arrays thereof are useful in the study of cell-cell and cell-tissue interactions between the mammalian skin cells/tissue comprising the construct and one or more additional cell types, including but not limited to pathogen-bearing cells, living pathogenic cells, cancer cells, immune cells, blood cells, stem progenitor cells, or genetically-manipulated cells.

In some embodiments, the array comprises engineered skin tissue constructs and additional tissue constructs. In further embodiments, the skin tissue construct is in direct contact with an additional tissue construct on one or more surfaces. In still further embodiments, the skin tissue is connected to one or more additional tissues constructs or cells via a fluid path or common fluid reservoir. In still further embodiments, the liquid media that contacts the engineered skin tissue construct contains living mammalian cells such as immune cells, blood-derived cells, or tumor-derived cells. In other embodiments, the liquid media that contacts the engineered skin tissue construct contains bacteria, fungi, viruses, parasites, or other pathogens.

Therapeutic Applications

In certain embodiments, the skin tissue of the current application is for use in treating a subject with a skin condition. In certain embodiments, the three-dimensional skin tissue is tor engraftment to a subject. The skin condition could be any condition for which skin grafts are utilized. The condition could be due to trauma such as burns caused by heat or chemicals. The condition could be caused by trauma that results in an open wound or the reopening of a previously closed wound. The condition could be caused by trauma that results in the removal of skin. The condition could be a skin cancer. The condition could be due to infection such as necrotizing fasciitis or purpura fulminans. The condition could be caused by skin necrosis. The condition could be cosmetic. The condition could be a cosmetic defect. The condition could be due to aging. In certain embodiments, the three-dimensional skin tissues are for use in procedures that aid wound healing.

In certain embodiments, the skin cells used in the three-dimensional engineered skin tissue are derived front the subject being treated (e.g., autologous). In certain embodiments, the skin cells used in the three-dimensional engineered skin tissue are from a donor considered to be histocompatible. In certain embodiments, the skin cells used in the three-dimensional engineered skin tissue are from a donor considered to be non-histocompatible. In certain embodiments, the three-dimensional engineered skin tissue is considered to be isogeneic, allogeneic or xenogeneic to the recipient. In certain embodiments, the cells used in the three-dimensional engineered skin tissue are pluripotent cells including, stem cells, induced pluripotent stem cells, embryonic stem cells, mesenchymal stem cells, or adult stem cells.

In some embodiments, the cells utilized in the three-dimensional engineered skin tissue are modified. In some embodiments, the cells utilized in the three-dimensional engineered skin tissue are modified to reduce rejection of the grab by the immune system. In some embodiments, the cells utilized in the three-dimensional engineered skin tissue are modified to promote histocompatibility between the three-dimensional engineered skin tissue and the recipient subject. In some embodiments, the cells utilized in the three-dimensional engineered skin tissue are modified to correct a congenital defect. In some embodiments, the modification of the cells utilized in the three-dimensional engineered skin tissue is biological, chemical or physical. In some embodiments, the modification of the cells utilized in the three-dimensional engineered skin tissue is genetic. In some embodiments, the genetic modification is the result of expression of a transgene, open reading frame, short hairpin RNA (shRNA), small interfering RNA (siRNA) or micro RNA (miRNA).

In some embodiments, a therapeutic substance is used to treat the cells before bioprinting. In some embodiments, the therapeutic substance is bioprinted with the cells, and included in the three dimensional engineered skin tissue, in some embodiments, the three-dimensional skin tissue is treated with a therapeutic substance sometime after bioprinting. In some embodiments, the therapeutic substance is an antibiotic, an antiviral, an antifungal, an anti-inflammatory. an immunosuppressant, an analgesic, an opiate, a vasoconstrictor, a vasodilator, a steroid, or a vitamin mixture. In certain embodiments, the therapeutic substance can also be any substance used to protect skin or promote its attachment or ability to thrive at a site of engraftment. These include but are not limited to skin protectants, moisturizers, adhesives, (biodegradable or non-biodegradable), physical barriers, porous membranes, or non-porous membranes, gels or scaffolds.

In certain embodiments, the skin tissue also comprises a therapeutic substance, and can be administered to the tissue in many ways as shown in FIG. 27, the therapeutic substance can be applied to the apical, ventral, basal, or lateral surface of any single layer or any plurality of layers bioprinted. The therapeutic substance can be applied to the entirety of the surface, or a portion of the surface. The therapeutic substance can be added between two layers that are the same cell type or a different cell type, embedded within a single layer or plurality of layers, or mixed homogenously or heterogeneously throughout a single layer or a plurality of layers. The therapeutic substance can be applied via art aerosol spray type mechanism or art extrusion mechanism. In other applications, tissues are completely or partially immersed in the therapeutic substance. In some embodiments, the tissue can be applied by suturing, stapling or the use of adhesives or films. In some instances, a bioprinted matrix or membrane may act as an adhesive or aid to administer, dispense or disperse a therapeutic substance similar to a transdermal patch. In other instances addition or adherence can be aided in combination or separately by a patch of a non-bioprinted material such as gauze or nylon mesh. Substances can be also administered manually, for example, as dispensed by pipet tip, swabbed, or applied by a blunted object. Therapeutic substances can be liquid, including solutions, suspensions, and emulsion. Therapeutic substances can also be solids, such as powders and granules, or semi-solids such as pastes. Therapeutic substances can be hydrous or anhydrous with varying levels of viscosity and administered in the form of but not limited to a liquid, oil, gel, foam, ointment, or cream. Substances may be applied aerosolized into a liquid aerosol such as a spray or fog. Substances may also be administered as a solid aerosol such as a smoke or dust. Substances may also be administered combined with a hydrogel such as Novogel®.

The disclosure herein includes systems for in vitro screening. The disclosure herein includes business methods. In some embodiments, the speed and scalability of the techniques and methods disclosed herein are utilized to design, build, and operate industrial and/or commercial facilities for production of engineered skin tissues and or organs for engraftment or use in generation of cell-based tools for research and development, such as in vitro assays. In further embodiments, the engineered skin tissues and or organs and arrays thereof are produced, stored, distributed, marketed, advertised, and sold as. for example, cellular arrays (e.g., micro arrays or chips), tissue arrays (e.g., microarrays or chips), and kits for biological assays and high-throughput drug screening. In other embodiments, the engineered skin tissues and/or organs and arrays thereof are produced and utilized to conduct biological assays and/or drug screening as a service.

EXAMPLES

The following illustrative examples are representative of embodiments of the software applications, systems, and methods described herein and are not meant to be limiting in any way.

Example 1—Bioprinting Full Thickness Skin Tissue by Continuous Deposition Using Dermal Bio-Ink Containing Alginate and Epidermal Bio-Ink Deposition by Aerosol Spray Method Procedures Bio-ink was generated by a cellular mixture of 100% primary adult human dermal fibroblasts (HDFa) in 6% gelatin and 1% alginate (Novogel® 3.0) in a concentration of 150 million cells per milliliter. Three-dimensional bio-ink constructs were printed by continuous deposition using the Novogen Bioprinter® platform in a 4 mm×4 mm×0.5 mm base sheet with a 1 mm wall bordering the top to create a dermal structure resembling a cup. One tissue construct was printed per transwell in a 6 well plate. The transwell printing surface contained a polytetrafluoroethylene (PTFE) membrane coated with equimolar mixture of types I and III collagen (bovine) with pores 3 μm in size. Following printing, constructs were immediately cross-linked by submerging in 5 ml of 50 mM calcium chloride for 2-5 minutes Calcium chloride was then aspirated and constructs were submerged in 5 ml of fibroblast growth media (DMEM containing 10% FBS and P/S/A). Constructs were allowed to mature for 24 hours in a non-humidified 37° C. incubator. After 24 hours, dermal tissue constructs were removed from the incubator and placed in a BSC hood. Media was aspirated immediately before aerosol spray application. Epidermal bio-ink. was generated by a cell suspension mixture of 90% primary adult human epidermal keratinocyies (HEKa) and 10% primary adult human epidermal melanocytes (HEMa) in a concentration of 1 million cells per milliliter media. Media used contained 90% keratinocyte growth media and 10% melanocyte media. Cells were dispensed into a sterile glass vial in a BSC hood in an aseptic manner and agitated manually to maintain suspension. The vial containing the cell suspension was attached to two tubes running through a tightly sealed lid. One set of tubing connected the volume of cell suspension to a spray nozzle inside the hood. Another set of tubing running from the inside of the vial lid connected to a compressed air tank outside the hood adjusted to 23-25 psi. The diameter of the spray was control led by the height of the spray nozzle. The height of the spray nozzle wits adjusted manually by attaching the tubing to an adjustable stand. The height was set at approximately 3 cm to allow for the height of a 6 well plate. The spray diameter was approximately 2.5 cm, or the width of one well in the plate. The rate of flow of the spray nozzle was controlled digitally by pulsed dispenses of 100 ms or 200 ms per spray. Well plates containing bioprinted dermal fibroblast tissue constructs were removed from the 37° C. incubator after 24 hours. Construct media was aspirated. Each well containing a dermal construct was individually placed directly under the spray nozzle. Applications of single, double, or multiple pulses at 100 ms or 200 ms were sprayed onto the surface of the construct. As a control spray was also administered to the transwell membrane alone. After aerosol spray, 2 mls of media was added to the outer area of the transwell basket. The media used for subsequent growth and maintenance of the skin tissue was a 50:40:10 ratio of HDFa:HEKa:HEMa media. The volume added was sufficient to collect at the base of the printed structure but not to submerge the structure. The spray volume was measured post print by collecting the dispensed volume into a 1.5 ml tube. Spray volume averaged 23 μl per spray pulse at 200 ms and 8.7 μl per spray at 100 ms. Viability was measured at 90% by trypan blue exclusion assay. Cell numbers averaged 1.4 million cells per ml which were back calculated to 32,200 cells per spray at 200 ms and 12,180 cells per spray at 100 ms. Tissues were treated with 0.34 mg/ml alginate lyase for 4 hours on day 3 (48 hours post aerosol spray application) in a volume of 3 ml per well. Media was added to the outer area of the transwell. The meniscus of the volume of lyase media was sufficient reach the top of the construct side without submerging the construct. Following lyase treatment, media was aspirated and 1 ml of fresh media was added to the outer area of each well bringing the tissue constructs to an air liquid interface. Media was changed daily at 1 ml per well subsequently for up to 12 days. After incubation, the constructs were fixed in 2% paraformaldehyde (PFA) for histology.

Results

Bioprinted dermal constructs were grown in fibroblast media maintained cohesive structure after incubation in media. Constructs were imaged immediately following crosslinking step on day 0 and before aerosol spray application on day 1 (FIG. 8). A bio-ink comprised of fibroblasts is printed by continuous deposition to create a dermal layer which is subsequently sprayed after a maturation period of 24 hours by a cellular mixture of keratinocytes and melanocytes to create an epidermal layer on top. All constructs maintained a cohesive structure post printing with continuous deposition anti aerosol spray application. Constructs contracted over time (FIG. 9). Skin tissues were cross sectioned perpendicular to the plane of the transwell to show the base and walls of the dermal cup structure. Sections were stained by H&E (FIG. 10). Keratinocytes in the epidermal layer deposited by aerosol spray were visualized by immunohistochemistry using keratinocyte-specific marker cytokeratin 14 (CK14)(FIG. 10). CK14 is a marker for basal layer keratinocytes in normal human epidermal skin and does not stain fibroblasts or melanocytes. Image shows positive CK14 staining (keratinocytes) in red and dapi counter staining nuclei in blue (fibroblasts). Positive staining can be seen only on the apical surface of the construct where the aerosol spray was applied. Staining shows an aerosol spray can successfully apply a thin layer of cells to a surface. Current application shows cells one layer thick. Positive CK14 staining is seen in constructs at day 2, 4, and 6 (FIG. 11). Fibroblast tissue becomes flatter over time as keratinocytes appear more rounded and potentially in clusters (arrows). Differences in keratinocyte morphology suggest potential differentiation over time. Keratinocytes were also sprayed onto the surface of transwell membranes (FIG. 12). Cells form similar groupings on transwell surface when compared to morphology of keratinocytes sprayed onto dermal tissue constructs day 8.

Example 2—Bioprinting Full Thickness Skin Tissue by Continuous Deposition Using Dermal Bio-Ink Containing Gelatin and Epidermal Bio-Ink Containing Cell Paste Procedures Bio-ink was generated by a cellular mixture of 100% primary adult human dermal fibroblasts (HDFa) in 6% gelatin (Novogel®) in a concentration of 150 million cells per milliliter. Three-dimensional bio-ink constructs were printed by continuous deposition using the Novogen Bioprinter® platform in a 4 mm×4 mm×0.5 mm base sheet with a 1 mm wall bordering the top to create a dermal structure resembling a cup. One tissue construct was printed per transwell m a 6 well plate. The transwell printing surface contained a polytetrafluoroethylene (PTFE) membrane coated with equimolar mixture of types I and III collagen (bovine) with pores 3 μm in size. Epidermal cell paste containing a mixture of 95% primary adult human epidermal keratinocytes (HEKa) and 5% primary adult human epidermal melanocytes (HEMa) was then printed on top of the dermal bio-ink. Cell paste was measured post print at 90.5% viable by trypan exclusion assay. Cell number in deposited epidermal layer was estimated at 160,000 cells by cell counting on a Cell-O-Meter. Media was then added to the outer well of the transwell in a volume of 2 ml. The media used for subsequent growth and maintenance of the skin tissue was a 50:40:10 ratio of HDFa:HEKa:HEMa media. The volume added was sufficient to collect at the base of the printed structure but not to submerge the structure. Media was changed 48 hours later and subsequently changed daily after that. At days 2, 9, and 12, constructs were either lysed for RNA analysis or fixed in 2% PFA for histological analysis.

Results

H&E staining of skin tissues at day 12 shows a distinct layered architecture (FIGS. 13, arrows, and 14). Fibroblasts m a dermal layer are observed at the base (purple) and differentiated keratinocytes in an epidermal layer (pink) on top. An unexpected finding with this approach is the extent of the layered architecture observed. In particular, there is a layer of cells with distinct morphology can be observed at the interface (arrows). This layer stains specifically for CK14, indicating that the keratinocyte cells in the deposited paste have arranged into a basal layer. Distinct layers of differentiated keratinocytes are visualized by simultaneously staining for a basal cell marker CK5 and involucrin (IVL), a later stage differentiation marker of granular and cornified keratinocytes Similar to normal human skirt, differences in morphology are seen as basal cells appear to have a distinct cuboidal morphology, while differentiated keratinocytes on top appear flatter. The layered architecture also includes CK10-positive spinous and granular keratinocytes in mid stages differentiation (FIG. 15). Although previous print methods have resulted in CK14 positive staining of the epidermal layer, the observed pat tern is widespread throughout the layer and non-specific to a basal region at day 10. In the current approach, what is unexpected is that the staining is limited to a defined region at the base of the epidermal layer similar to native human skin at day 12 (FIG. 16). Gene expression analysis supports histological findings. Data shows an increase in epidermal differentiation markers CK1, CK10, and especially late marker FLG over time. Gene expression also shows that collagen 4 levels increase over time, suggesting formation of a basement membrane. Collagen 1 levels are maintained over the time course of the experiment suggesting dermal layer remains viable (FIG. 17).

Example 3—Additional Example of Bioprinting Full Thickness Skin Tissue by Continuous Deposition Using Dermal Bio-Ink Containing Gelatin and Epidermal Bio-Ink Containing Cell Paste Procedures Bio-ink was generated by a cellular mixture of 100% primary adult human dermal fibroblasts (HDFa) in 8% gelatin (Novogel®) in a concentration of 100 million cells per milliliter. The cell:gelatin ratio was altered to reduce the cellular density of the dermal sheet to better mimic dermal tissue in native skin. Three-dimensional bio-ink constructs were printed by continuous deposition using the Novogen Bioprinter® platform in a 4 mm×4 mm×0.5 mm base sheet to create a dermal structure resembling a sheet. One tissue construct was printed per transwell in a 6 well plate. The transwell printing surface contained a polytetrafluoroethylene (PTFE)-membrane coated with equimolar mixture of types I and III collagen (bovine) with pores 3 μm in-size. Epidermal cell paste containing a mixture of 100% primary neonatal human epidermal keratinocytes (HEKn) was then printed on top of the dermal bio-ink. A separate but identical epidermal paste structure was simultaneously deposited next to the dermal sheet directly onto the transwell printing surface. This structure was only comprised of epidermal keratinocyte paste and contained no dermal tissue. Cell paste was measured post print at 87.1% viable by trypan exclusion assay. Cell number in deposited epidermal layer was estimated at 60,000 cells by cell counting on a Cell-O-Meter. Immediately following the print, constructs were placed in 4° C. for 10 minutes. This is a key step to harden the Novogel®, which helps to maintain the printed shape and improve construct to construct uniformity. Cold media was then added to the outer well of the transwell in a volume of 3 ml. The media used for subsequent growth and maintenance of the skin tissue was a 50:50 ratio of HDFa:HEKn media. The initial volume added was sufficient to submerge the structure. All subsequent media changes used warmed media (37° C.) added to the outer well of the transwell and not to the inner basket. Media was changed 48 hours later and reduced to a volume of 1.5 ml per well to bring the structure to an air-liquid interface (ALI). Media arid subsequently changed 48 hours after that (day 4) at a volume of 1.5 ml. On day 5, media was changed and further reduced to 1 ml per well and subsequently changed daily. At days 0 and 12, constructs were either lysed for RNA analysis or fixed in 2% PFA for histological analysis.

Results

Subsequent histological analysis to compare epidermal layer patterning of paste that had been printed on top of a dermal sheet versus directly onto the transwell surface yielded unexpected findings (FIGS. 18A and B). H&E staining of skin tissues at day 12 shows a distinct layered architecture only in structures with epidermal paste printed on top of a dermal layer (FIGS. 18C and D versus F and G, FIG. 19A). Fibroblasts in a dermal layer are observed at the base (purple) and differentiated keratinocytes in an epidermal layer (pink) on top. In particular, there iv a layer of cells with distinct morphology that can be observed at the interface. Distinct layers of differentiated keratinocytes are visualized by simultaneously staining for a basal cell marker CK5 (green) and involucrin (IVL, red), a later stage differentiation marker of granular and cornified keratinocytes (FIG. 18F versus H, FIG. 19B). The distinct green layer indicates that the keratinocytes cells in the deposited paste have arranged into a basal layer with a layer of more differentiated IVL positive cells on top. Similar to normal human skin, differences in morphology are seen as basal cells that appear to have a distinct cuboidal morphology, while differentiated keratinocytes on top appear flatter. Staining for the proliferation marker PCNA (FIG. 19E, green) indicates that proliferation is high in both dermal fibroblasts and basal layer keratinocytes but not in differentiating keratinocytes. This pattern is similar to that which is found in native skin. Staining for apoptosis by TUNEL (FIG. 19F) also low showing very few positive staining cells in either dermal or epidermal layer. Collectively PCNA and TUNEL staining demonstrate that both dermal and epidermal compartments of the full thickness tissue are viable at day 12. Gene expression analysis supports histological findings. Data shows an increase in mid epidermal differentiation markers CK1, CK10, and later markers IVL, Loricrin, and at day 12 compared to day 0. Gene expression also shows that collagen 1 and 4 levels are maintained over the time course of the experiment, while collagen 3 levels increase suggesting the dermal layer remains viable and functional (FIG. 20). A number of surprising results were determined from this: for example, that epidermal paste can stratify into a distinct layered architecture. Current 3D skin models rely on differentiation of a single keratinocyte monolayer over an extended period of time to achieve this. Here we show that stratification, is possible to achieve with a paste. The thickness of the paste is greater than a monolayer and shows that cells can self-organize within the paste and differentiate as layers. Also, we show that the keratinocyte paste printed directly onto the transwell surface without the presence of dermal tissue did not organize into stratified layers. Staining for the same differentiation markers shows mixed expression with no defined layers or distinct cell morphology. This unexpected finding indicates that the dermal layer directs differentiation and/or stratification of the epidermal keratinocytes, and that there is a uniqueness to the combination of dermal and epidermal cells that is not present in the epidermal cells alone. 3) The extent of the layered architecture observed in the tissues comprised of both epidermal and dermal cells including the staining of the CR5-positive basal layer which is limited to a defined region at the base of the epidermal layer similar to native human skin. The layered architecture also includes a CK10 positive (FIG. 19C) spinous and granular keratinocytes in mid stages differentiation and with a morphologically distinct cornified layer of keratinocytes visible by H&E and Trichrome staining above that (FIGS. 19A and D respectively). A noteworthy advantage to this approach is the appearance of the dermal layer. H&E staining shows that the dermal fibroblasts do not form a thin sheet as in earlier examples 1 and 2, but a thicker structure. Collagen deposition, which is a key indicator of normal fibroblast function in the dermis can be seen by both trichrome staining (blue color) and by immunofluorescent staining for collagen 3 (red) in between dermal cells (FIG. 19).

Example 4—Utilizing Bioprinted Full Thickness Skin Tissue in a Toxicology Model with 1 Hour Exposure to Known Irritant 1% Triton X-100™

Procedures

Bio-ink was generated by a cellular mixture of 100% primary adult human dermal fibroblasts (HDFa) in 8% gelatin (Novogel® 2.0) at a concentration of 100 million cells per milliliter. The cell:gelatin ratio was altered to reduce the cellular density of the dermal sheet to better mimic dermal tissue in native skin. Three-dimensional bio-ink constructs were printed by continuous deposition using the Novogen Bioprinter® platform in a 4 mm×4 mm×0.5 mm base to create a dermal structure resembling a sheet. One tissue construct was printed per transwell in a 6-well plate. The transwell printing surface contained a polytetrafluoroethylene (PTFE) membrane coated with equimolar mixture of types I and II collagen (bovine) with pores 3 μm in size. Epidermal cell paste containing a mixture of 100% primary neonatal human epidermal keratinocytes (HEKn) was then primed on top of the dermal bio-ink. Cell paste was measured post print at 87.1% viable by trypan exclusion assay. Cell numbers in the deposited epidermal layer was estimated at 60,000 cells by cell counting on a Cell-O-Meter. Immediately following the print, constructs were placed at 4° C. for 10 minutes. Cold media was then added to the outer well of the transwell in a volume of 3 ml. The media used for subsequent growth and maintenance of the skin tissue was a 50:50 ratio of HDFa:HEKn media. The initial volume added was sufficient to submerge the structure. All subsequent media changes used warmed media (37° C.) added to the outer well of the transwell and not to the inner basket. Media was changed 48 hours later and reduced to a volume of 1.5 ml per well to bring the structure to an air-liquid interface (ALI). Media and subsequently changed 48 hours after that (day 4) at a volume of 1.5 ml. On day 5, media was changed and further reduced to 1 ml per well and subsequently changed daily. On day 10, skin tissues were subject to a skin irritation test method using 1% Triton X 100. 1% Triton X-100™ is a known irritant and reference chemical currently used in other 3D skin models. Methods were based on OECD guidelines 439 and 431 for applying human skin models to in vitro skin irritation or corrosion, respectively. On day 10, conditioned media was saved (designated time=0) and 1 ml of fresh media was added to the outer well of the transwell. The printed skin tissue was then treated with 20 μl of PBS as a negative control or with 20 μl of 1% Triton X-100™ as a positive control and known irritant. Test substances were pipetted manually to the apical surface of the tissue. Triton X-100™ was diluted to a 1% aqueous solution in deionized water and sterile filtered through a 20 micron filter before use. Samples were incubated for 30 minutes at 37° C. followed by 30 minutes at room temperature for a total of 60 minutes. Media was saved (designated time=1 hour). Samples were then washed extensively by PBS rinsing. Transwells were then placed in a new 6-well plate with fresh media (1 ml) added to the outer well then placed back into 37° C. overnight. The media was then changed at 24 hours and at 48 hours post treatment. Total media collected included time points=–48, 0, 1, 24, and 48 hours. IL-1α production (R&D Systems) was analysed in a colorimetric assays per manufacturer's protocol. Media was analysed for lactate dehydrogenase as a marker for cytotoxicity. IL-1α production was assessed as a complementary endpoint to classic cytotoxicity testing to improve predictability of irritants. Keratinocytes normally produce and release inflammatory cytokine IL-1α in response to chemical or physical stress. At 48 hours post treatment (day 12), tissues were either lysed for RNA extraction and subsequent qPCR analysis, or tested for viability by alamar blue assay then rinsed in PBS and fixed with 2% PFA for histological analysis. Alamar blue (Life Technologies) was added per manufacturer's instructions to media and incubated with tissue constructs (1 ml) at 37° C. for 3 hours. Viability was measured as fluorescence in the media by conversion of resazurin to resorufin.

Results

The effect of Triton X-100 treatment on viability/cytotoxicity was quantified by alamar blue assay, lactate dehydrogenase (LDH) activity, and IL-1α production. Skin tissues treated with 1% Triton X 100 for 1 hour exhibited a roughly 2-fold induction in LDH activity compared to PBS control at 1 hour, 24 hours, and 48 hours point tested post treatment. In contrast, PBS control is similar to initial baseline at 0 hours (FIG. 21A). IL-1α activity also increased in response to Triton X treatment in comparison to PBS control with the greatest difference observed 1 hour post treatment. IL-1α levels remained high at 24 hours post treatment but returned to baseline at 48 hours (FIG. 21B). Comparison of tissues 48 hours post treatment shows an 80% reduction in viability as compared to the PBS control (FIG. 18C). H&E staining of skin tissues in the PBS control group at day 12 shows a distinct layered architecture (FIG. 22A). Fibroblasts in a dermal layer are observed at the base (purple) and differentiated keratinocytes in an epidermal layer (pink) on top. In particular, there is a layer of cells with distinct morphology that can be observed at the interface. Distinct layers of differentiated keratinocytes are visualized by simultaneously staining for a basal cell marker CK5 (green) and involuerin (IVL, red), a later stage differentiation marker of granular and cornified keratinocytes (FIG. 22B). The distinct green layer indicates that the keratinocyte cells in the deposited paste have arranged into a basal layer with a layer of more differentiated IVL positive cells on top, Similar to normal human skin, differences in morphology are seen as basal cells that appear to have a distinct cuboidal morphology, while differentiated keratinocytes on top appear flatter. The layered architecture also includes CK10-positive spinous and granular keratinocytes in mid stages differentiation (FIG. 22C). Collagen deposition, which is a key indicator of normal fibroblast function in the dermis can be seen by both trichrome staining (FIG. 22D) (blue color) and by immunofluorescent staining for collagen 3 (red) in between dermal cells (FIG. 22E). Staining for the proliferation marker PCNA (green) indicates that proliferation is high in both dermal fibroblasts and basal layer keratinocytes but not in differentiating keratinocytes. This pattern is similar to that which is found in native skin. Staining for apoptosis by TUNEL also low showing very few positive staining cells in either dermal or epidermal layer (FIG. 22F). Collectively PCNA and TUNEL staining demonstrate that both dermal and epidermal compartments of the full thickness tissue are viable at day 12. Tissues treated with Triton X appeared similar to PBS control tissues macroscopically. Histological analysis, however revealed a separation of the epidermal and dermal layers by H&E (FIG. 22G), suggesting a possible necrosis of the basement membrane and/or basal keratinocyte layer. Although keratinocyte differentiation markers CK5, IVL and CK10 can be seen (FIGS. 22H and I), the CK5 positive basal keratinocyte layer is fragmented. Collagen 3 startling is also compared to the PBS control indicating a reduction in dermal fibroblast function (FIG. 22K). Viability is also reduced and is consistent with biochemical data. This is demonstrated by a reduction in proliferation evident by a less PCNA positive staining in the dermal fibroblasts and lack of staining in the basal layer. Combined with an increase in apoptosis as demonstrated by TUNEL positive staining in the dermal layer (FIG. 22L), histology suggests 1% Triton X is an irritant to bioprinted skin. Gene expression analysis supports histological and biochemical findings. Data shows an increase in epidermal differentiation markers CK1, CK10, and late markers IVL, Loricrin, and FLG over time in the PBS control group in comparison to tissue at day 0. Gene expression also shows that collagen 1 and 4 levels are maintained over the time course of the experiment, while collagen 3 levels increase suggesting the dermal layer remains viable (FIG. 23). Treatment with 1% Triton X dramatically reduces expression of both epidermal and dermal markers 48 hours post exposure (FIG. 23). CK1 and CK10 are reduced, suggesting a possible effect to the spinous/granular layer of the epidermis. Collagen production of types 1, 3, and 4 collagen is reduced, suggesting a negative impact on the function of the dermal fibroblasts as well. Inflammatory cytokine IL1a gene expression was also analyzed and found to increase about 3 fold in comparison to the PBS control, suggesting that 48 hours post treatment, keratinocytes are still stressed by the exposure to Triton X (FIG. 24).

Example 5—Utilizing Bioprinted Full Thickness Skin Tissue in a Toxicology Model with a 15 Minute Exposure to Known Irritants 5% SDS and 1% Triton X When Miniaturized into a 24 Well Plate Format Procedures Bio-ink was generated by a cellular mixture of 100% primary adult human dermal fibroblasts (HDFa) in 8% gelatin (Novogel® 2.0) in a concentration of 50 million cells pet milliliter. The cell:gelatin ratio was altered to further reduce the cellular density of the dermal sheet to better mimic dermal tissue in native skin. Three-dimensional bio-ink constructs were printed by continuous deposition using the Novogen Bioprinter® platform in a 2 mm×2 mm×0.5 mm base sheet to create a dermal structure resembling a sheet. A smaller syringe needle was used to achieve greater resolution at the reduced size. Instead of printing one 0.5 mm sheet with a 500 um diameter syringe needle, two layers of 0.25 mm sheets printed with a 250 um diameter needle. One tissue construct was printed per transwell-in a 24 well plate. The transwell printing surface contained a polytetrafluoroethylene (PTFE)-membrane coated with equimolar mixture of types I and III collagen (bovine) with pores 3 μm in-size. Epidermal cell paste containing a mixture of 100% primary neonatal human epidermal keratinocytes (HEKn) was then printed on ton of the dermal bio-ink. Cell paste was measured post print at 96.0% viable by trypan exclusion assay. Cell number in deposited epidermal layer was estimated at 11,000 cells by cell counting on a Cell-O-Meter. Immediately following the print, constructs were placed in 4° C. for 10 minutes. This is a key step to harden the Novogel®, which helps to maintain the printed shape and improve construct to construct uniformity. Cold media was then added to the outer well of the transwell in a volume of 1 ml. The media used for subsequent growth and maintenance of the skin tissue was a 50:50 ratio of HDFa:HEKn media. The initial volume added was sufficient to submerge the structure. All subsequent media changes used warmed media (37° C.) added to the outer well of the transwell and not to the inner basket. Media was changed 48 hours later and reduced to a volume of 0.25 ml per well to bring the structure to an air-liquid interface (ALI). Media and subsequently changed daily. Skin tissues were subject to a skin irritation test method using 1% Triton X 100 and 5% SDS. 1% Triton X 100 and 5% SDS are known irritants and reference chemicals currently used in other 3D skin models. Methods were based on OECD guidelines 439 and 431 for applying human skin models to in vitro skin irritation or corrosion, respectively. On day 13, the media was changed. The conditioned media was saved (designated time=0) and 1 ml of fresh media was added to the outer well of the transwell. The printed skin tissue was then treated with 5 μl of PBS as a negative control or with 5 μl of 1% Triton X 100 or with 5 μl of %% SDS as a positive controls and known irritants. Test substances were pipetted manually to the apical surface of the tissue. Both Triton X 100 and SDS were diluted in an aqueous solution in deionized water and sterile filtered through a 20 micron filter before use. Samples were incubated for 13 minutes at room temperature. Media was saved (designated time=15 minutes). Samples were then washed extensively by PBS rinsing. Transwells were then placed in a new 6 well plate with fresh media (0.25 ml) added to the outer well then placed back into 37° C. overnight The media was then changed again at 24 hours and 42 hours post treatment. Total media collected included time points=0, 15 minutes, 24 hours, and 42 hours. IL-1α production (R&D Systems) was analyzed in a colorimetric assays per manufacturer's protocol. Media was analyzed for lactate dehydrogenase as a marker for cytotoxicity IL-1α production was assessed as a complementary endpoint to classic cytotoxicity testing to improve predictability of irritants. Keratinocytes produce and release inflammatory cytokine IL-1α in response to chemical or physical stress. At 42 hours post treatment (day 15), tissues were either lysed for RNA extraction and subsequent qPCR analysis or tested for viability by alamar blue assay then rinsed in PBS and fixed with 2% PFA for histological analysis. Alamar blue (Life Technologies) was added per manufacturer's instructions to media and incubated with tissue constructs (0.25 ml) at 37° C. for 3 hours. Viability was measured as fluorescence in the media by conversion of resazurin to resorufin.

Results

Skin tissues exhibited an elevated LDH response to both SDS and Triton X compared to PBS control tissues 42 hours post exposure (FIG. 25A). The LDH activity in the SDS treated group was about 1.7 fold higher than PBS, while Triton X was about 1.4 fold higher suggesting that 15 minute exposure with 5% SDS had a more pronounced effect on construct viability than 1% Triton X. IL-1α production was also induced by both irritants, however the SDS treatment produced a much stronger response (FIG. 25B) consistent with LDH activity. Tissues treated with both SDS and Triton X exhibited a reduction in viability by alamar blue assay (FIG. 25C). Tissues treated with SDS were only 2.45% viable compared to the PBS control, while tissues treated with Triton X were 68.73% viable. This data is consistent with the LDH activity and IL1a production suggesting that 5% SDS is a much stronger irritant than 1% Triton X under these testing conditions. The difference in response to Triton X in Example 4 compared to Example 5 may be due to the shorter incubation time with the irritant.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Example 6—Additional Example of Bioprinting Full Thickness Skin Tissue by Continuous Deposition Using Dermal Bio-Ink Containing Gelatin, Extracellular Matrix, and Epidermal Bio-Ink Containing Cell Paste Procedures Bio-ink was generated by a cellular mixture of 100% primary adult human dermal fibroblasts (HDFa) in 8% gelatin (Novogel®) in a concentration of 100 million cells per milliliter. Three-dimensional bio-ink constructs were printed by continuous deposition using the Novogen Bioprinter® platform in a 3 mm×3 mm×0.5 mm base sheet. One tissue construct was printed per transwell in a 12 well plate. The transwell printing surface contained a polytetrafluoroethylene (PTFE) membrane coated with equimolar mixture of types I and III collagen (bovine) with pores 3 μm in size. Intracellular matrix (ECM) containing a mixture of type IV collagen, laminin, and heparin sulfate proteoglycan was then printed on top of the dermal bio-ink at a concentration of 120 micrograms per milliliter. Epidermal cell paste containing 100% primary adult human epidermal keratinocytes (HEKa) was then printed on top of the ECM. Cell paste was measured post print at 94.4% viable by trypan exclusion assay. Cell number in deposited epidermal layer w as estimated at 14,000 cells by cell counting on a Cell-O-Meter. Immediately following the print, constructs were placed in 4° C. for 10 minutes. Cold media was then added to the outer well of the transwell in a volume of 0.5 ml. The media used for subsequent growth and maintenance of the skin tissue was a 50:50 ratio of HDFa:HEKa media. The volume added was sufficient to collect at the base of the printed structure but not to submerge the structure. Media was again added after 90 minutes at a volume of 0.5 ml for a total of 1 ml in the well. Media was changed 48 hours later at a volume of 1 ml. Media was again changed after additional 24 hours (Day 3) at a volume of 0.5 ml to bring the structure to an air-liquid interface (ALI). Media was subsequently changed at a volume of 0.5 ml every other day after that. At day 10 constructs were fixed in 2% PFA for histological analysis.

Results

H&E staining of skin tissues at day 10 shows a distinct layered architecture (FIGS. 28A and B). Fibroblasts in a dermal layer are observed at the base and differentiated keratinocytes in an epidermal layer on top. The distinct layered architecture of differentiated keratinocytes is visualized by simultaneously staining for a basal cell marker CK5 and differentiated marker involucrin (IVL). Similar to normal human skin, differences in morphology are seen as basal cells appear to have a distinct cuboidal morphology, while differentiated keratinocytes on top appear flatter (FIGS. 28A and B). Although previous print methods have resulted in CK5 positive staining of the basal keratinocyte layer, the interface between the epidermal and dermal layers or dermal-epidermal junction was not clearly demarcated. At the interface between the basal layer of epidermal keratinocytes and the dermal layer is the basement membrane. Types IV and VII collagen are both specific markers of basement membrane formation. In the current approach, what is unexpected is the expression and extent of the organization of basement membrane markers types IV and VII collagen. What is unexpected is that the staining patterns of both markers is limited to a defined region, or line, precisely at the base of the basal layer of epidermal keratinocytes at the dermal-epidermal junction similar to native human skin (FIG. 28E-H).

What is claimed is:

1. A three-dimensional, engineered, biological skin tissue that is capable of being cultured for at least 12 days, comprising:
   a. a dermal layer in contact with a surface that is not a scaffold, wherein the dermal layer comprises dermal fibroblasts, and
   b. an epidermal layer in contact with the dermal layer, wherein the epidermal layer comprises keratinocytes, wherein the skin tissue comprises a plurality of layers of differentiated keratinocytes within 12 days of culture.

2. The skin tissue of claim 1, wherein the dermal fibroblasts in the dermal layer comprise primary human fibroblasts.

3. The skin tissue of claim 2, wherein the dermal fibroblasts in the dermal layer consist essentially of primary human fibroblasts.

4. The skin tissue of claim 1, wherein the keratinocytes in the epidermal layer comprise primary human keratinocytes.

5. The skin tissue of claim 4, wherein the keratinocytes in the epidermal layer consist essentially of primary human keratinocytes.

6. The skin tissue of claim 1, wherein the epidermal layer further comprises melanocytes.

7. The skin tissue of claim 6, wherein the cells in the epidermal layer consist essentially of keratinocytes and melanocytes.

8. The skin tissue of claim 7, wherein the keratinocytes and melanocytes are present in the epidermal layer at a ratio of 90:10 to 99:1 keratinocytes to melanocytes.

9. The skin tissue of claim 1, wherein the dermal layer and/or the epidermal further comprises a plurality of organoids, wherein the organoids comprise sebocytes, glandular cells, or follicle cells.

10. The skin tissue of claim 1, wherein the dermal layer and/or the epidermal further comprises cancer cells.

11. The skin tissue of claim 1, which does not comprise mature tissue innervation, perfusable lymphatic tissue, or perfusable vasculature.

12. The skin tissue of claim 1, which is free of pre-formed scaffold.

13. The skin tissue of claim 1, wherein the epidermal layer is in continuous contact with the dermal layer.

14. The skin tissue of claim 1, wherein the epidermal layer is about 20 μm to about 500 μm thick.

15. The skin tissue of claim 14, wherein the epidermal layer is about 150 μm thick.

16. The skin tissue of claim 1, wherein the dermal layer is about 10 μm to about 1000 μm thick.

17. The skin tissue of claim 16, wherein the epidermal layer is about 500 μm thick.

18. An array comprising a plurality of three-dimensional, engineered, biological skin tissues configured to facilitate an in vitro assay, a drug-screening assay, or a cosmetic assay, wherein each of the plurality of skin tissues is the skin tissue of claim 1.

19. A three-dimensional, engineered, biological skin tissue that is capable of being cultured for at least 12 days, comprising:

a. a hypodermal layer in contact with a surface that is not a scaffold, wherein the hypodermal layer comprises endothelial cells, b. a dermal layer in contact with the hypodermal layer, wherein the dermal layer comprises dermal fibroblasts, and c. an epidermal layer in contact with the dermal layer, wherein the epidermal layer comprises keratinocytes, wherein the skin tissue comprises a plurality of layers of differentiated keratinocytes within 12 days of culture.

20. A three-dimensional, engineered, biological skin tissue that is capable of being cultured for at least 12 days, comprising:

a. a dermal layer in contact with a surface that is not a scaffold, wherein the dermal layer comprises dermal fibroblasts, b. an epidermal layer comprising keratinocytes, and c. a basal layer in contact with the dermal layer and the epidermal layer, wherein the basal layer comprises basal keratinocytes, wherein the skin tissue comprises a plurality of layers of differentiated keratinocytes within 12 days of culture.

* * * * *